(12) United States Patent
Ericksen et al.

(10) Patent No.: US 12,330,734 B2
(45) Date of Patent: Jun. 17, 2025

(54) ACTIVE SUSPENSION AND BODY WEARABLE DEVICE INTEGRATION

(71) Applicant: Fox Factory, Inc., Duluth, GA (US)

(72) Inventors: Everet Owen Ericksen, Woodland, CA (US); Wesley E. Allinger, Santa Cruz, CA (US); Evan Peterson, Santa Cruz, CA (US)

(73) Assignee: Fox Factory, Inc., Duluth, GA (US)

( * ) Notice: Subject to any disclaimer, the term of this patent is extended or adjusted under 35 U.S.C. 154(b) by 0 days.

(21) Appl. No.: 18/134,777

(22) Filed: Apr. 14, 2023

(65) Prior Publication Data

US 2023/0331333 A1    Oct. 19, 2023

Related U.S. Application Data

(60) Provisional application No. 63/331,745, filed on Apr. 15, 2022.

(51) Int. Cl.
*B62J 45/416* (2020.01)
*A61F 2/50* (2006.01)
(Continued)

(52) U.S. Cl.
CPC ........... *B62J 45/416* (2020.02); *A61F 2/70* (2013.01); *A61F 2/748* (2021.08); *A61F 5/0102* (2013.01);
(Continued)

(58) Field of Classification Search
CPC . B62K 2025/044; B62K 25/04; F16F 9/3292; F16F 9/5126; F16F 9/50; F16F 2222/12; F16F 2228/066; F16F 2230/08; F16F 2230/18; F16F 9/466; B62J 45/416; B62J 45/20; B62J 45/41; B62J 45/42;
(Continued)

(56) References Cited

U.S. PATENT DOCUMENTS 3,986,118 A    10/1976  Madigan
5,952,823 A    9/1999   Sprecher et al.
(Continued)

FOREIGN PATENT DOCUMENTS

CN    111938991 A  *  11/2020
DE    102019214614 A1  *  3/2021
(Continued)

OTHER PUBLICATIONS

Abeysuriya, et al., "A low-profile orthosis for tremor attenuation: A CDF design optimization of the damping system", "https://www.medicaldesignandoutsourcing.com/a-low-profile-orthosis-for-tremor-attenuation-a-cdf-design-optimization-of-the-damping-system/", Aug. 12, 2015.
(Continued)

*Primary Examiner* — Drew J Brown

(57) ABSTRACT

An active suspension system with body wearable device integration is disclosed. The system includes a prosthetic having a shock assembly with at least one active valve and a controller communicatively coupled with the at least one active valve of the shock assembly, the controller configured to communicate damping adjustment information to the at least one active valve of the shock assembly, the damping adjustment information used by said at least one active valve to modify a damping characteristic of the shock assembly.

37 Claims, 26 Drawing Sheets

(51) Int. Cl.

| | | |
|---|---|---|
| *A61F 2/70* | (2006.01) | |
| *A61F 2/74* | (2006.01) | |
| *A61F 5/01* | (2006.01) | |
| *A61H 3/00* | (2006.01) | |
| *B62J 45/20* | (2020.01) | |
| *B62K 25/04* | (2006.01) | |
| *F16F 9/32* | (2006.01) | |
| *F16F 9/50* | (2006.01) | |

(52) U.S. Cl.
CPC ............... *A61H 3/00* (2013.01); *B62J 45/20* (2020.02); *B62K 25/04* (2013.01); *F16F 9/3292* (2013.01); *F16F 9/50* (2013.01); *A61F 2002/5006* (2013.01); *A61F 2002/705* (2013.01); *A61F 2005/0169* (2013.01); *A61H 2201/0165* (2013.01); *B62K 2025/044* (2013.01); *F16F 2222/12* (2013.01); *F16F 2228/066* (2013.01); *F16F 2230/08* (2013.01); *F16F 2230/18* (2013.01)

(58) Field of Classification Search
CPC .......... A61F 2/70; A61F 2/748; A61F 5/0102; A61F 2002/5006; A61F 2002/705; A61F 2005/0169; A61H 3/00; A61H 2201/0165
See application file for complete search history.

(56) References Cited

U.S. PATENT DOCUMENTS

| | | | | |
|---|---|---|---|---|
| 6,863,291 | B2 * | 3/2005 | Miyoshi | B62K 25/04 280/283 |
| 7,374,028 | B2 | 5/2008 | Fox | |
| 7,484,603 | B2 | 2/2009 | Fox | |
| 8,627,932 | B2 | 1/2014 | Marking | |
| 8,838,335 | B2 | 9/2014 | Bass et al. | |
| 8,857,580 | B2 | 10/2014 | Marking | |
| 8,955,653 | B2 | 2/2015 | Marking | |
| 9,033,122 | B2 | 5/2015 | Ericksen et al. | |
| 9,120,362 | B2 | 9/2015 | Marking | |
| 9,239,090 | B2 | 1/2016 | Marking et al. | |
| 9,278,598 | B2 * | 3/2016 | Galasso | B60G 17/018 |
| 9,303,712 | B2 | 4/2016 | Cox | |
| 9,353,818 | B2 | 5/2016 | Marking | |
| 9,682,604 | B2 | 6/2017 | Cox et al. | |
| 9,797,467 | B2 | 10/2017 | Wootten et al. | |
| 10,036,443 | B2 | 7/2018 | Galasso et al. | |
| 10,060,499 | B2 | 8/2018 | Ericksen et al. | |
| 10,086,670 | B2 * | 10/2018 | Galasso | B60G 17/019 |
| 10,415,662 | B2 | 9/2019 | Marking | |
| 10,443,671 | B2 | 10/2019 | Marking | |
| 10,737,546 | B2 | 8/2020 | Tong | |
| 11,337,817 | B2 * | 5/2022 | Staton | A61F 2/68 |
| 2004/0088057 | A1 * | 5/2004 | Bedard | A61F 2/72 623/25 |
| 2010/0276906 | A1 * | 11/2010 | Galasso | F16F 9/065 188/266.2 |
| 2011/0202236 | A1 * | 8/2011 | Galasso | B62K 25/286 701/37 |
| 2013/0144489 | A1 * | 6/2013 | Galasso | B60G 17/0424 701/37 |
| 2015/0073657 | A1 * | 3/2015 | Galasso | B60G 17/018 701/37 |
| 2018/0328442 | A1 * | 11/2018 | Galasso | B62K 25/04 |
| 2018/0339566 | A1 * | 11/2018 | Ericksen | B60G 17/08 |
| 2020/0309229 | A1 * | 10/2020 | Galasso | B62K 25/286 188/266 |
| 2021/0061405 | A1 * | 3/2021 | Ericksen | B62K 3/00 |
| 2021/0300140 | A1 * | 9/2021 | Ericksen | B62J 45/20 |
| 2022/0204121 | A1 * | 6/2022 | Ericksen | B62K 25/04 |
| 2022/0210650 | A1 | 6/2022 | Ericksen et al. | |
| 2022/0242190 | A1 | 8/2022 | Stanford et al. | |
| 2024/0092135 | A1 * | 3/2024 | Randall | B60G 17/018 |

FOREIGN PATENT DOCUMENTS

| | | | | |
|---|---|---|---|---|
| DE | 102020133551 A1 * | 6/2021 | ............. | B62J 45/00 |
| EP | 2905157 A1 * | 8/2015 | ........... | B60G 17/018 |
| EP | 3354496 A1 * | 8/2018 | ......... | B60G 17/0152 |
| EP | 3895966 A1 * | 10/2021 | ........... | B60G 17/018 |
| EP | 4019304 A1 * | 6/2022 | ........... | B60G 17/019 |
| EP | 4021029 A1 * | 6/2022 | ................ | B62J 1/08 |
| WO | WO-2004017871 A2 * | 3/2004 | ........... | A61B 5/1038 |
| WO | WO-2016197068 A1 * | 12/2016 | ........... | A61B 5/4023 |

OTHER PUBLICATIONS

Alvarado-Rivera, et al., "Semiactive Knee Orthotic Using a MR Damper and a Smart Insole to Control the Damping Force Sensing the Plantar Pressure", May 2022, 19 Pages.

Shiozaki, et al., "SP-861-Vehicle Dynamics and Electronic Controlled Suspensions SAE Technical Paper Series No. 910661", International Congress and Exposition, Detroit, Mich., Feb. 25-Mar. 1, 1991.

\* cited by examiner

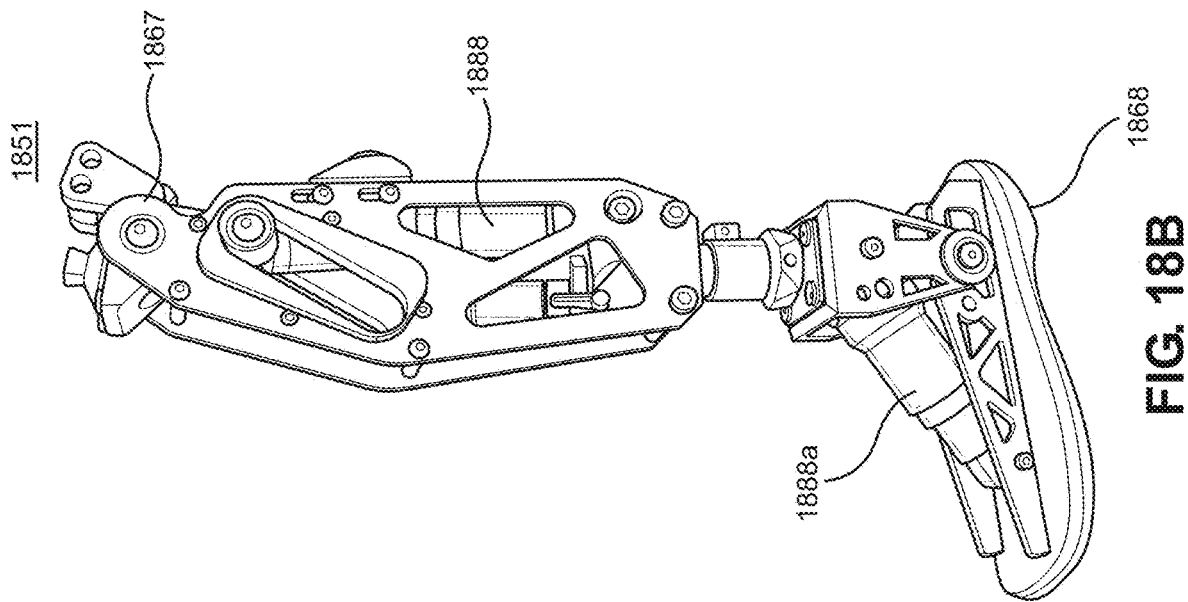
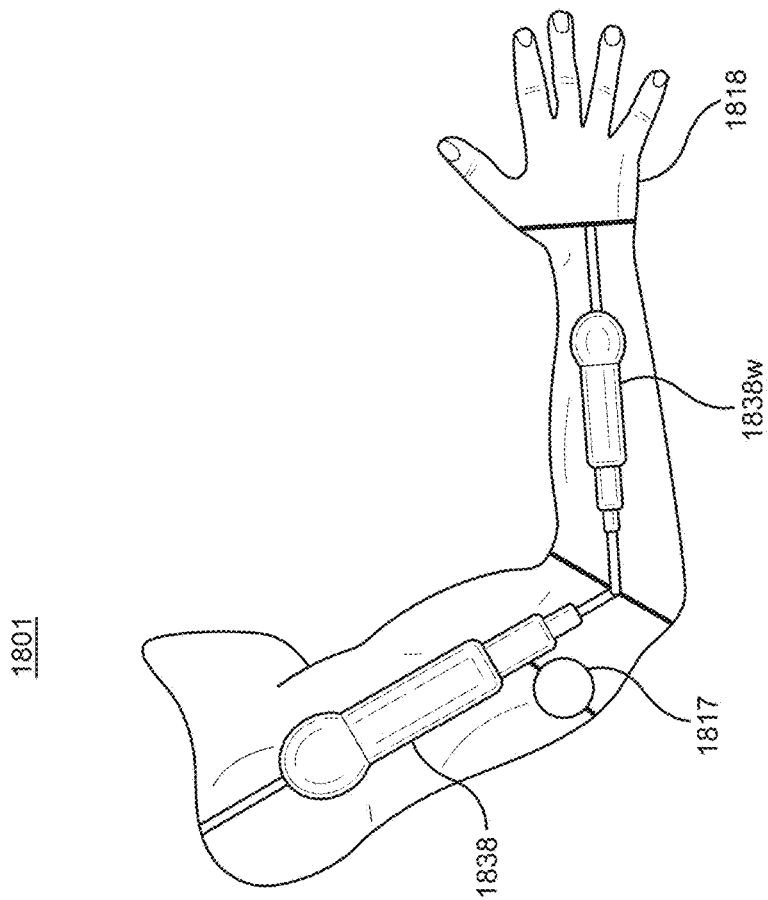
FIG. 18B
FIG. 18A

ACTIVE SUSPENSION AND BODY WEARABLE DEVICE INTEGRATION

CROSS-REFERENCE TO RELATED APPLICATIONS (PROVISIONAL)

This application claims priority to and benefit of co-pending U.S. Provisional Patent Application No. 63/331,745 filed on Apr. 15, 2022, entitled "WIRELESS ACTIVE SUSPENSION PROSTHETIC INTEGRATION" by Ericksen et al., and assigned to the assignee of the present application, the disclosure of which is hereby incorporated by reference in its entirety.

FIELD OF THE INVENTION

Embodiments of the invention generally relate to an active suspension system.

BACKGROUND OF THE INVENTION

Vehicle suspension systems typically include a spring component or components and a damping component or components that form a suspension to provide for a comfortable ride, enhance performance of a vehicle, and the like. Active and semi-active vehicle suspension systems include an active valve in the shock assembly that allows a characteristic (compression adjustment, rebound adjustment, stiffness, and the like) of the shock assembly to be modified while the vehicle is in motion.

When initially developed, a prosthetic was used to replace a missing body part. Often, the prosthetic was extremely basic and provided a simple solution, e.g., a peg for a leg, a hook for a hand, etc. As technology has advanced, so have prosthetics. Presently, for example, a shock assembly can be used in conjunction with an articulating joint of a prosthetics to provide enhanced/increased/new performance characteristics and more natural prosthetic operation.

BRIEF DESCRIPTION OF THE DRAWINGS

FIG. 14 is a screenshot of a ride settings management page, in accordance with an embodiment.

FIG. 17B is a screenshot of tune page of the application, shown in accordance with an embodiment.

FIG. 18A is a perspective view of a prosthetic arm with an active valve shock assembly, in accordance with an embodiment.

FIG. 18B is a perspective view of a prosthetic leg with an active valve shock assembly, in accordance with an embodiment.

Figure 1:
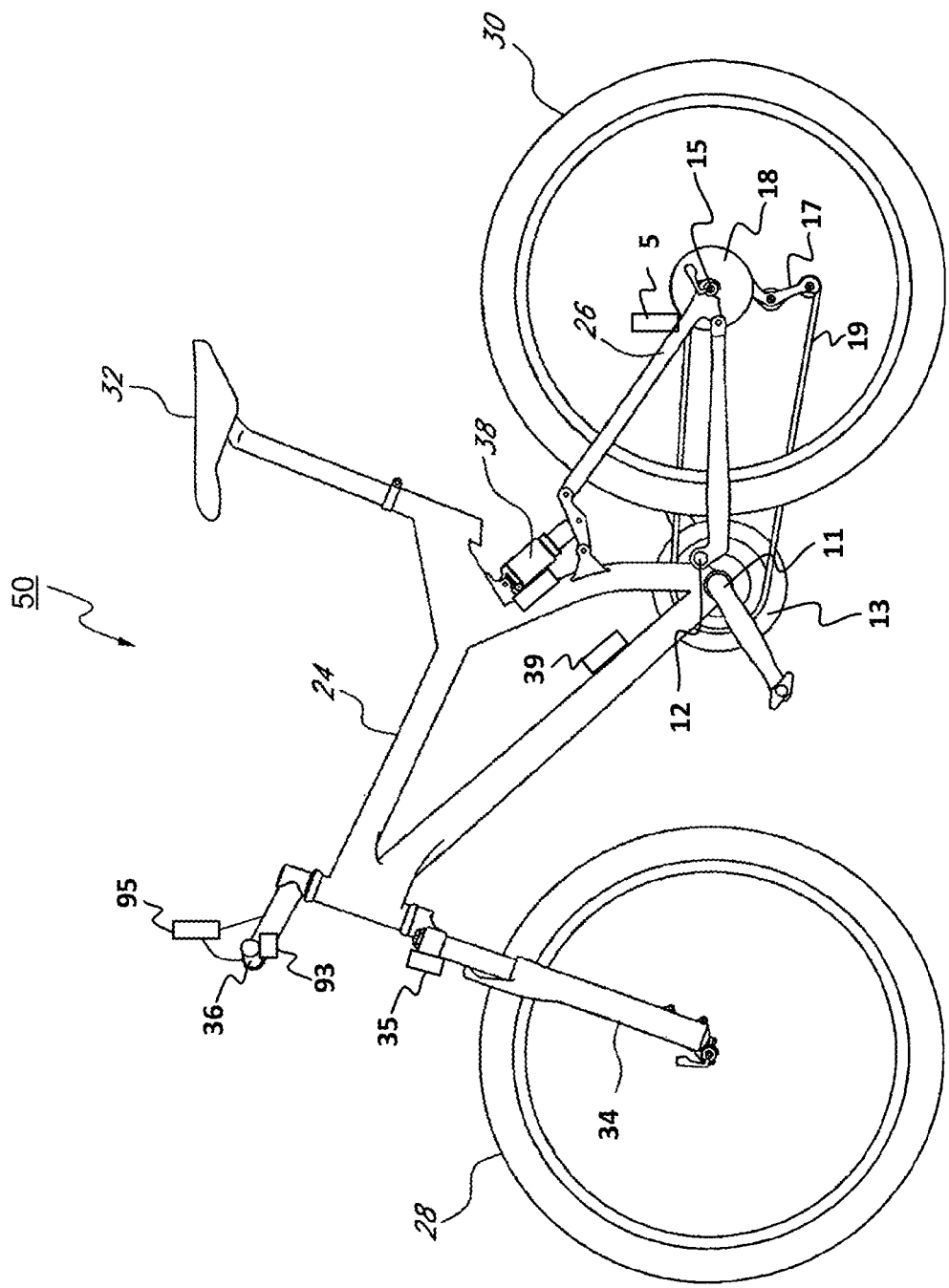
FIG. 1 is a perspective view of a bicycle, in accordance with an embodiment.

The drawings referred to in this description should be understood as not being drawn to scale except if specifically noted.

DESCRIPTION OF EMBODIMENTS

The detailed description set forth below in connection with the appended drawings is intended as a description of various embodiments of the present invention and is not intended to represent the only embodiments in which the present invention may be practiced. Each embodiment described in this disclosure is provided merely as an example or illustration of the present invention, and should not necessarily be construed as preferred or advantageous over other embodiments. In some instances, well known methods, procedures, objects, and circuits have not been described in detail as not to unnecessarily obscure aspects of the present disclosure.

In the following discussion, the term "body wearable device" refers to a prosthetic, orthotic, and/or exoskeleton. The term "active body wearable device" refers to a prosthetic, orthotic, and/or exoskeleton that includes an active adjustment capability.

A "prosthetic" is a device used as a replacement for a missing body part. For example, a person lacking a limb or portion of a limb, e.g., leg for example, would use a prosthetic to replace the missing portion of the leg.

An "orthotic" is a device to enhance or correct a body part that doesn't function properly. For example, a person with an injured joint, e.g., elbow for example, would use an orthotic elbow brace (splint, or the like) to reduce the stress on the elbow joint.

An "exoskeleton" is a user wearable device that supports and assists movement and/or augments the capabilities of the user's body. The exoskeleton is able to provide support, assist movement, and/or augment the capabilities of a limb, a joint, a plurality of limbs, a plurality of joints, or entire body. In one embodiment, the exoskeleton is an orthotic. For example, in one embodiment, a user wears an orthotic exoskeleton boot (or pair or boots) to provide support, assistance, and/or augmentation of the ankle, foot, calf, and the like.

In one embodiment, the exoskeleton is both an orthotic and a prosthetic. For example, in one embodiment, a user missing a foot would wear an orthotic exoskeleton boot (or pair of boots) to provide support, assistance, and/or augmentation of the ankle, calf, and the like, and also provide a replacement foot.

The term "active", as used when referring to a valve or damping component, means adjustable, manipulatable, etc., during typical operation of the valve. For example, an active valve can have its operation changed to thereby alter a corresponding damping characteristic from a "soft" damping setting to a "firm" damping setting by, for example, adjusting a switch in a passenger compartment of a vehicle. Additionally, it will be understood that in some embodiments, an active valve may also be configured to automatically adjust its operation, and corresponding damping characteristics, based upon, for example, operational information pertaining to the vehicle and/or the suspension with which the valve is used. Similarly, it will be understood that in some embodiments, an active valve may be configured to automatically adjust its operation, and corresponding damping characteristics, to provide damping based upon received user input settings (e.g., a user-selected "comfort" setting, a user-selected "sport" setting, and the like). Additionally, in many instances, an "active" valve is adjusted or manipulated electronically (e.g., using a powered solenoid, or the like) to alter the operation or characteristics of a valve and/or other component. As a result, in the field of suspension components and valves, the terms "active", "electronic", "electronically controlled", and the like, are often used interchangeably.

In the following discussion, the term "manual" as used when referring to a valve or damping component means manually adjustable, physically manipulatable, etc., without requiring disassembly of the valve, damping component, or suspension damper which includes the valve or damping component. In some instances, the manual adjustment or physical manipulation of the valve, damping component, or suspension damper, which includes the valve or damping component, occurs when the valve is in use. For example, a manual valve may be adjusted to change its operation to alter a corresponding damping characteristic from a "soft" damping setting to a "firm" damping setting by, for example, manually rotating a knob, pushing or pulling a lever, physically manipulating an air pressure control feature, manually operating a cable assembly, physically engaging a hydraulic unit, and the like. For purposes of the present discussion, such instances of manual adjustment/physical manipulation of the valve or component can occur before, during, and/or after "typical operation of the vehicle".

It should further be understood that a vehicle suspension may also be referred to using one or more of the terms "passive", "active", "semi-active" or "adaptive". As is typically used in the suspension art, the term "active suspension" refers to a vehicle suspension which controls the vertical movement of the wheels relative to vehicle. Moreover, "active suspensions" are conventionally defined as either a "pure active suspension" or a "semi-active suspension" (a "semi-active suspension" is also sometimes referred to as an "adaptive suspension").

In a conventional "fully active suspension", a motive source such as, for example, an actuator, is used to move (e.g. raise or lower) a wheel with respect to the vehicle. In a "semi-active suspension", no motive force/actuator is employed to move (e.g. raise or lower) a wheel with respect to the vehicle. Rather, in a "semi-active suspension", the characteristics of the suspension (e.g. the firmness of the suspension) are altered during typical use to accommodate conditions of the terrain and/or the vehicle. Additionally, the term "passive suspension", refers to a vehicle suspension in which the characteristics of the suspension are not changeable during typical use, and no motive force/actuator is employed to move (e.g. raise or lower) a wheel with respect to the vehicle. As such, it will be understood that an "active valve", as defined above, is well suited for use in a "fully active suspension" or a "semi-active suspension".

In general, a suspension system for a vehicle provides a motion modifiable connection between a portion of the vehicle that is in contact with a surface (e.g., an unsprung portion) and some or all of the rest of the vehicle that is not in contact with the surface (e.g., a suspended portion). For example, the unsprung portion of the vehicle that is in contact with the surface can include one or more wheel(s), skis, tracks, hulls, etc., while some or all of the rest of the vehicle that is not in contact with the surface include suspended portions such as a frame, a seat, handlebars, engines, cranks, etc.

The suspension system will include one or numerous components which are used to couple the unsprung portion of the vehicle (e.g., wheels, skids, wings, belt, etc.) with the suspended portion of the vehicle (e.g., seat, cockpit, passenger area, cargo area, etc.). Often, the suspension system will include one or more shock assemblies which are used to reduce feedback from the unsprung portion of the vehicle before that feedback is transferred to the suspended portion of the vehicle, as the vehicle traverses an environment. However, the language used by those of ordinary skill in the art to identify a shock assembly used by the suspension system can differ while referring to the same (or similar) types of components. For example, some of those of ordinary skill in the art will refer to the shock assembly as a shock absorber, while others of ordinary skill in the art will refer to the shock assembly as a damper (or damper assembly).

The shock assembly often consists of a (damping) piston and piston rod telescopically mounted in a fluid filled cylinder (e.g., a housing). The fluid (e.g., damping fluid, working fluid, etc.) may be, for example, a hydraulic oil, a gas such as nitrogen, air, or the like. In one embodiment, the shock assembly will include a mechanical spring (e.g., a helically wound spring that surrounds or is mounted in parallel with the body of the shock assembly). In one embodiment, the shock assembly will include an air spring. In one embodiment, the shock assembly will include both a mechanical spring and an air spring.

In its basic form, the suspension is used to increase ride comfort, performance, endurance, component longevity and the like. In general, the force of jarring events, rattles, vibrations, jostles, and the like which are encountered by the portion of the vehicle that is in contact with the surface are reduced or even removed as it transitions through the suspension before reaching suspended portions of the vehicle to include components such as seats, steering wheels/handlebars, pedals/foot pegs, fasteners, drive trains, engines, and the like.

For example, on a wheeled vehicle, a portion of the wheel (or tire) will be in contact with the surface being traversed (e.g., pavement, dirt, gravel, sand, mud, rocks, etc.) while a shock assembly and/or other suspension system components will be coupled between a wheel retaining assembly and the suspended portion of the vehicle (often a portion of the vehicle frame and associated systems, the seat, handlebars, pedals, controls, steering wheel, interior, etc.).

In a snow machine, a portion of the track and/or the skis that will be in contact with the surface being traversed (e.g., snow, ice, etc.) while a shock assembly and/or other suspension components will be coupled between a track retaining assembly (and similarly the skis retaining assembly) and the suspended portion of the vehicle (usually including the engine and associated systems, the seat, handlebars, etc.).

In a boat or PWC vehicle, a portion of the hull will be in contact with the surface of the water while a shock assembly and/or other suspension components will be coupled between the hull and the suspended portion(s) of the vehicle (such as the seat, the handlebars, a portion of the vehicle frame, and/or the like).

In a body wearable device, an unsprung portion of the body wearable device (e.g., hand, foot, arm, leg, elbow, knee, etc.) will be in contact with a vehicle while one or more active shock assemblies and/or other suspension components will be coupled between the unsprung portion and the suspended portion(s) of the body wearable device (e.g., another portion of the body wearable device, and/or the body to which the body wearable device is coupled). In general, the one or more active shock assemblies are used to automatically adjust the performance characteristics of the body wearable device as the user traverses an environment.

In the following discussion, and for purposes of clarity, a bicycle is utilized as the example vehicle in some, but not all cases. However, in another embodiment, the vehicle is any one of a variety of vehicles that utilize active valve dampers such as, but not limited to, a bicycle, a motorized bicycle, a motorcycle, a watercraft (e.g., boat, jet ski, PWC, etc.), a snow machine, a single wheeled vehicle, a multi-wheeled vehicle, a side-by-side, an on- and/or off-road vehicle, or the like. In general, a motorized bike can include a bike with a combustion motor, an electric bike (e-bike), a hybrid electric and combustion bike, a hybrid motor and pedal powered bike, and the like.

Overview

As discussed herein, an active valve system uses one or more sensor to essentially read the terrain. The goal is to discern if the bike is experiencing bumpy or smooth terrain and then change the suspension characteristics accordingly. On smooth terrain, the suspension is in the firm mode. In bumpy terrain, the suspension is in the soft mode. In one embodiment, the active adjustment of suspension characteristics is accomplished using aspects such as when the sensor's signal exceeds a configurable threshold, the active valve system opens solenoids in the rear shock and/or front fork, putting one or both in soft mode. After a configurable period of time (e.g., 500 ms) where no further bumps are detected, the shock and/or fork return to firm mode.

In one embodiment, there are several other active adjustments that can be made by the active valve system. For example, the above threshold and timer values can be changed based on the incline/decline angle of the bike. For example, there can be one set of configurable thresholds and timers for decline mode, another for flat riding, and yet another set for climbing. Moreover, the angles that constitute decline, flat or incline modes are also configurable. Finally, the active valve system has control style adjustment characteristics that dictate whether two or more of the suspension dampers work together (both going to soft mode together, for example), or independently.

The active valve system also allows for groups of the above settings to be packaged as a set, called a "tune". Using the active valve system smartphone app, these groupings allow users to swap tunes conveniently and quickly on their mobile device as they encounter new terrain or ride conditions. As changes are made, they are immediately transmitted via Bluetooth (or other near field communication (NFC) protocols) to the bike's active valve controller.

In one embodiment, the active valve controller has the capability to store a given number of tunes, such that each stored tune is instantly available during the ride.

In one embodiment, the application (e.g., a FOX® Live Valve® application) runs on a computing system. In one embodiment, the application is written in Python, a platform-independent programming language. In one embodiment, the equipment used to make settings changes to an active valve controller (e.g., a FOX® Live Valve® controller) includes the computer system and a communication interface (such as a USB-NFC dongle).

In one embodiment, the application allows the user to: read settings via NFC from an active valve controller, from a file on a storage device, or the like; Edit tune names, thresholds, timers, control styles, incline angles, and the like; Save settings to the active valve controller or to a file on a storage device; and the like.

In one embodiment, the application also automatically saves settings or backup files anytime the source is modified; allows users to load, view and edit backup files; prevents a user from entering any invalid settings values; provides a history of all user actions in a scrollable log; and the like.

Thus, the Application can make adjustments to a range of settings which affect how the active valve suspension behaves under a variety of conditions. The settings can be downloaded wirelessly directly to a controller, saved to a configuration file for use at a later time or on other components, and the like. In one embodiment, when settings are uploaded or downloaded, a copy of the previous settings is saved to a backup configuration file.

Operation

FIG. 1 is a perspective view of a bicycle 50 in accordance with an embodiment. Although a bicycle 50 is used in the discussion, in another embodiment, the system is used for a number of different vehicles with a semi-active damping system such as, but not limited to an e-bike, a motorcycle, ATV, jet ski, car, snow mobile, side-by-side, and the like. In one embodiment, the system is used in one or more different locations on any of the different vehicles. For example, in one embodiment, the semi-active damping system is used in one or more dampers in suspension systems for a wheel, a frame, a seat, a steering assembly, or any other component that utilizes a damper.

Bicycle 50 has a frame 24 with a suspension system comprising a swing arm 26 that, in use, is able to move relative to the rest of frame 24; this movement is permitted by, inter alia, a rear active valve damper 38. The front forks 34 also provide a suspension function via a damping assembly (similar to active valve damper 38 described herein) in at least one fork leg; as such the bicycle 50 is a full suspension bicycle (such as an ATB or mountain bike). However, the embodiments described herein are not limited to use on full suspension bicycles. In particular, the term "suspension system" is intended to include vehicles having front suspension only, rear suspension only, seat suspension only, a combination of two or more different suspensions, and the like.

In one embodiment, swing arm 26 is pivotally attached to the frame 24 at pivot point 12 which is located above the bottom bracket axis 11. Although pivot point 12 is shown in a specific location, it should be appreciated that pivot point 12 can be found at different distances from bottom bracket axis 11 depending upon the rear suspension configuration. The use of the specific pivot point 12 herein is provided merely for purposes of clarity. Bottom bracket axis 11 is the center of the pedal and front sprocket assembly 13. Bicycle 50 includes a front wheel 28 which is coupled with the frame 24 via front forks 34 and a rear wheel 30 which is coupled with the frame 24 via swing arm 26. A seat 32 is coupled with the frame 24, via a seatpost, in order to support a rider of the bicycle 50.

The front wheel 28 is supported by front forks 34 which, in turn, is secured to the frame 24 by a handlebar assembly 36. The rear wheel 30 is coupled with the swing arm 26 at rear axle 15. A rear damping assembly (e.g., active valve damper 38) is positioned between the swing arm 26 and the frame 24 to provide resistance to the pivoting motion of the swing arm 26 about pivot point 12. Thus, the illustrated bicycle 50 includes a suspension member between swing arm 26 and the frame 24 which operate to substantially reduce rear wheel 30 impact forces from being transmitted to the rider of the bicycle 50.

Bicycle 50 is driven by a chain 19 that is coupled with both front sprocket assembly 13 and rear sprocket 18. As the rider pedals the front sprocket assembly 13 is rotated about bottom bracket axis 11 a force is applied to chain 19 which transfers the energy to rear sprocket 18. Chain tension device 17 provides a variable amount of tension on chain 19.

In one embodiment, bicycle 50 includes one or more sensors, smart components, or the like for sensing changes of terrain, bicycle 50 pitch, roll, yaw, speed, acceleration, deceleration, or the like.

In one embodiment, a sensor 5 is positioned proximate the rear axle 15 of bicycle 50. In another embodiment a sensor 35 is positioned proximate to front fork 34. In yet another embodiment, both sensor 5 and sensor 35 are on bicycle 50.

In one embodiment, the angular orientation of the sensor is movable through a given range, thereby allowing alteration of a force component sensed by the sensor in relation to a force (vector) input. In one embodiment, the value for the range is approximately 120°. In one embodiment, the value for the range is approximately 100°. It is understood that the sensor can be moved or mounted in any suitable configuration and allowing for any suitable range of adjustment as may be desirable. That is useful for adjusting the sensitivity of the sensor to various anticipated terrain and bicycle speed conditions (e.g., the bicycle speed affects the vector magnitude of a force input to the bicycle wheel for constant amplitude terrain disparity or "bump/dip." Varying size bumps and dips also affect the vector input angle to the wheel for constant bicycle speed).

The sensors may be any suitable force or acceleration transducer (e.g. strain gage, wheatstone bridge, accelerometer, hydraulic, interferometer based, optical, thermal or any suitable combination thereof). One or more sensors may utilize solid state electronics, electro-mechanical principles or MEMS, or any other suitable mechanisms. In one embodiment, the sensor comprises a single axis self-powered accelerometer, such as for example ENDEVCO® model 2229C. The 2229C is a comparatively small device with overall dimensions of approximately 15 mm height by 10 mm diameter, and weighs 4.9 g. Its power is self-generated and therefore the total power requirements for the bicycle 50 are reduced; this is an advantage, at least for some types of bicycles, where overall weight is a concern. An alternative single axis accelerometer is the ENDEVCO® 12M1A, which is of the surface-mount type. The 12M1A is a single axis accelerometer comprising a bimorph sending element which operates in the bender mode. This accelerometer is particularly small and light, measuring about 4.5 mm by 3.8 mm by 0.85 mm, and weighs 0.12 g. In one embodiment, the sensor may be a triaxial accelerometer such as the ENDEVCO® 67-100. This device has overall dimensions of about 23 mm length and 15 mm width, and weighs 14 g.

One or more sensor(s) may be attached to the swing arm 26 directly, to any link thereof, to an intermediate mounting member, to front fork 34, or to any other portion or portions of the bicycle 50 as may be useful. In one embodiment, a sensor is fixed to an unsprung portion of the bicycle 50, such as for example the swing arm assembly 10. In one embodiment, the sensor is fixed to a sprung portion of the bicycle 50, such as the frame 24. In general, one or more sensors may be integrated with the vehicle structure, suspension components, suspension component controller(s) and data processing system as described in U.S. Pat. Nos. 7,484,603; 8,838,335; 8,955,653; 9,303,712; 10,060,499; 10,443,671; and 10,737,546; each of which is herein incorporated, in its entirety, by reference. Sensors and valve actuators (e.g. electric solenoid or linear motor type—note that a rotary motor may also be used with a rotary actuated valve) may be integrated herein utilizing principles outlined in SP-861-Vehicle Dynamics and Electronic Controlled Suspensions SAE Technical Paper Series no. 910661 by Shiozaki et. al. for the International Congress and Exposition, Detroit, Mich., Feb. 25-Mar. 1, 1991 which paper is incorporated herein, in its entirety, by reference. Further, sensors and valves, or principles, of patents and other documents incorporated herein by reference, may be integrated one or more embodiments hereof, individually or in combination, as disclosed herein.

In one embodiment, sensor information is obtained from mobile device 95. Although mobile device 95 is shown mounted to handlebar assembly 36, it should be appreciated that the mobile device 95 is well suited to being located in other locations such as, but not limited to, a rider's backpack, pocket, or the like, and still provide the sense input information.

In general, mobile device 95 is a smart device such as a mobile phone, a smart phone, a tablet, a smart watch, a piece of smart jewelry, smart glasses, or other user portable device(s) having wireless connectivity. Mobile device 95 is capable of broadcasting and receiving via at least one network, such as, but not limited to, WiFi, Cellular, Bluetooth, NFC, and the like. In one embodiment, mobile device 95 includes one or more of a display, a processor, a memory, a GPS, a camera, and the like.

In one embodiment, location information can be provided by the GPS. In one embodiment, the location information is provided by and/or enhanced by other location information components such as, but not limited to, the broadcast range of an identified beacon, a WiFi hotspot, overlapped area covered by a plurality of mobile telephone signal providers, and the like. In one embodiment, instead of using GPS information, the location of mobile device 95 is determined within a given radius, such as the broadcast range of an identified beacon, a WiFi hotspot, overlapped area covered by a plurality of mobile telephone signal providers, or the like. In one embodiment, geofences are used to define a given area and an alert or other indication is made when the mobile device 95 enters into or departs from a geofence.

Mobile device 95 includes sensors such as audio, visual, motion, acceleration, altitude, GPS, and the like. In one embodiment, mobile device 95 includes an optional application that operates thereon.

In one embodiment, switch 93 is a positional switch used in conjunction with the active valve suspension and the vehicle setup application (e.g., vehicle setup application 1124 discussed in further detail herein). In one embodiment, switch 93 is a multi-positional switch, an upshift/downshift type of switch, a button type switch, or the like. For example, switch 93 is a 2-position switch, a 3-position switch, a switch that can cycle through a number of different modes (similar to a gear shift), or the like.

In one embodiment, switch 93 is wireless. For example, switch 93 communicates with the mobile device 95 (or other components) via Bluetooth, NFC, WiFi, a hotspot, a cellular network, or any other type of wireless communications.

In one embodiment, switch 93 is wired. For example, switch 93 communicates with mobile device 95 (or other components) by way of an input port such as USB, micro USB, or any other connectable wired configuration that will allow switch 93 to be communicatively coupled with mobile device 95. In one embodiment, switch 93 has both wired and wireless communication capabilities.

Although switch 93 is shown mounted to handlebar assembly 36, it should be appreciated that switch 93 is mountable in a different location on the vehicle, on a mount coupled with the vehicle, or the like. In one embodiment, the location of switch 93 is modifiable and is located on the vehicle based on a rider's preference.

Some or all of components of embodiments herein including sensors, switches, controllers, valves, and the like may be interconnected or connected by wire, wireless, NFC, WAN, LAN, Bluetooth, WiFi, ANT, GARMIN® low power usage protocol, or any suitable power or signal transmitting mechanism.

Figure 2:
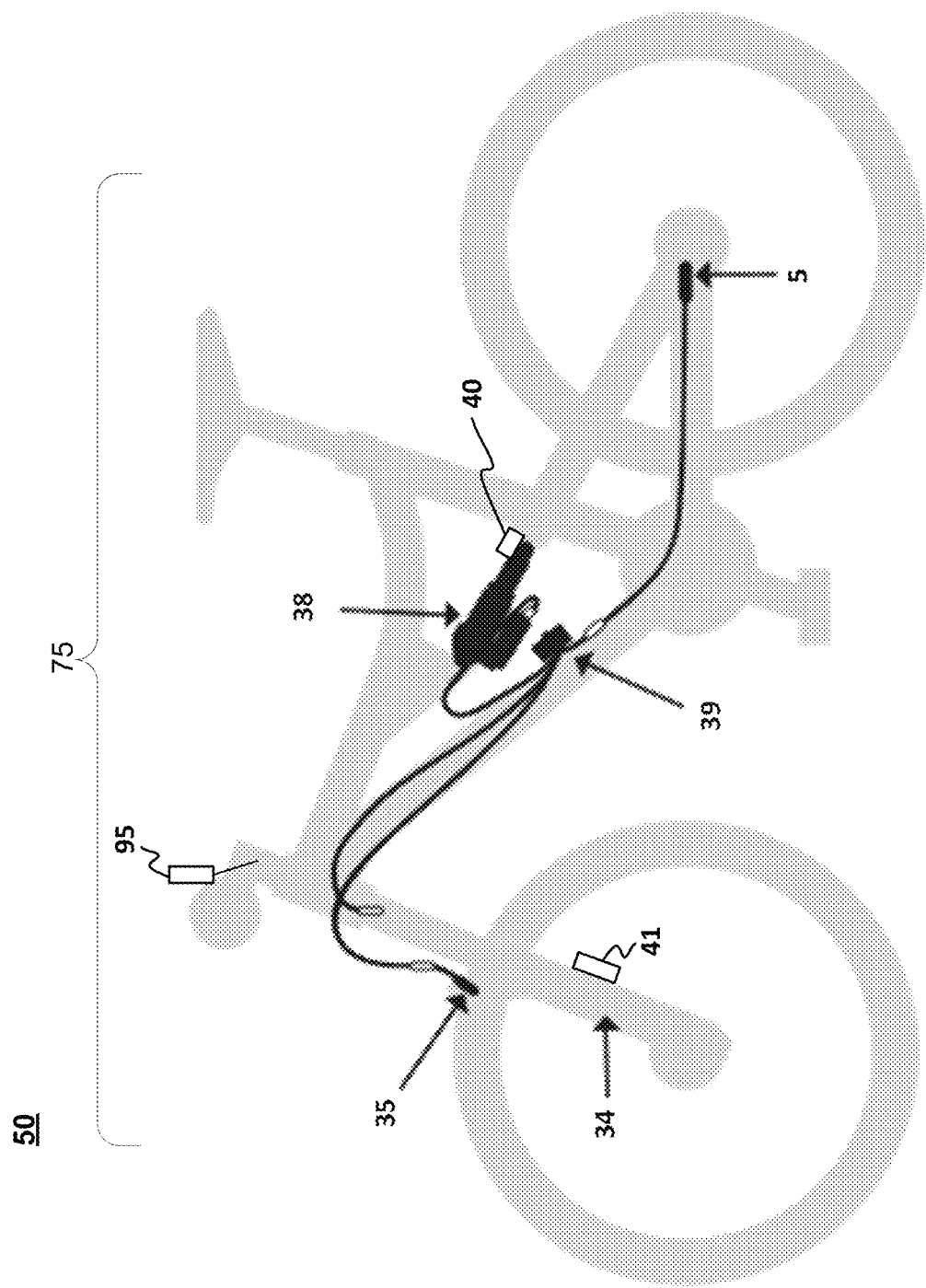
FIG. 2 is a perspective view of an active valve system on a bicycle, in accordance with an embodiment.

FIG. 2 is a perspective view of an active valve system 75 on bicycle 50 having a number of sensors, in accordance with an embodiment. In general, one or more sensors (e.g., sensor 5, 35, 40, and/or 41) are used for sensing characteristics (or changes to characteristics) such as terrain, environment, temperature, vehicle speed, vehicle pitch, vehicle roll, vehicle yaw, component activity, or the like. It is understood that the one or more sensors may be imbedded, moved, mounted, or the like, in any suitable configuration and allowing for any suitable range of adjustment as may be desirable. Although a number of sensors are shown in FIG. 2, it should be appreciated that there may be only a single sensor or more than two sensors in operation.

The sensor(s) may be any suitable force or acceleration transducer (e.g. strain gage, Wheatstone bridge, accelerometer, hydraulic, interferometer based, optical, thermal or any suitable combination thereof). The sensor(s) may utilize solid state electronics, electro-mechanical principles or MEMS, or any other suitable mechanisms.

In one embodiment, the one or more of the sensors are a single axis accelerometer, a triaxial accelerometer, a measurement type sensor such as an infrared based time of flight sensor, a radar, 2D and 3D imager, ultrasonic sensor, photoelectric sensor, LiDar, and the like. In one embodiment, the measurement type sensor is a STMicroelectronics sensor and specifically STMicroelectronics sensor model VL53L0X.

In general, a measurement sensor is used to measure distances by projecting a laser light (or sound, etc.) and measuring the reflection. Differences in return times and wavelengths are used to provide distance measurement information. For example, the time of flight sensor mounted on the vehicle is used to measure the distance to the ground in front of the vehicle. In so doing, the time of flight sensor will provide distance data that is used to monitor and detect terrain changes.

In one embodiment, the measurement type sensor continuously and/or repeatedly measures a distance from the sensor to the ground. By monitoring the distance from the sensor to the ground, the measurement type sensor can determine the existence of an upcoming obstacle (e.g., height changes due to holes, bumps, or other obstacles), a shape or abruptness of the obstacle, etc.

For example, in one embodiment, the sensor is aimed at a point that is approximately 2 feet in front of the bike. In general, by repeatedly measuring the distance from the sensor to the ground in front of the vehicle, any changes in that distance are indicative of an upcoming obstacle.

Although a distance of 2 feet is used in one embodiment, in another embodiment, the distance to the point in front of the bike varies depending upon speed, terrain, and the like. For example, in one embodiment, the distance in front of the bike is defined by user option, factory guidance provided by the damper manufacturer, sensor manufacturer, bike manufacturer, damping system controller manufacturer, or the like.

In operation on a steady surface, the sensor will regularly obtain a time-of-flight of x (plus or minus some nominal value depending upon the type of surface, type of vehicle, the precision/tolerance of the sensor, user or system defined tolerance, or the like). For example, in one embodiment, if a bike with a very tight suspension setup (such as a road bike), is being ridden on a paved road, the nominal value is slight (e.g., less than a ¼") such that a change in measurement (e.g., a ½" deep pothole) is larger than the nominal value. In contrast, in one embodiment, if a bike with a suspension setup that is not as tight as the road bike (such as a gravel bike) is being ridden on the road, the nominal value is larger (e.g., less than 1") such that the change in measurement (e.g., a ½" deep pothole) is not larger than the nominal value. Furthermore, in one embodiment, if a bike with a longer suspension setup (such as a mountain bike) is being ridden on the road, the nominal value is even larger (e.g., less than 3") such that the change in measurement (e.g., a 2" deep pothole) is not larger than the nominal value.

When the sensor obtains a time-of-flight of x+n (where n is a value that is larger than the nominal value) it means that a depression (or hole) is detected. Moreover, the size of n provides information about the depth of the depression, the size of the depression, the geometry (e.g., angle or grade) of the depression, etc.

In contrast, when the sensor obtains a time of flight of x-n, a bump (or rise) is detected. Here, the size of n provides information about the height of the rise, the size of the rise, the geometry of the rise, etc.

In one embodiment, the n value is preset for the type of active suspension, the terrain type, the vehicle type, the ride type, or the like.

In one embodiment, the sensors of active valve system 75 provide the obtained sensor data to a suspension controller 39 which uses the sensor data to monitor the terrain and make suspension adjustments. In one embodiment, suspension controller 39 makes suspension adjustments to active valve damper 38, a live valve damper in front fork 34, or the like. In one embodiment, suspension controller 39 use the sensor information to recognize when bicycle 50 is climbing, traversing, or descending.

In one embodiment, suspension controller 39 monitors the terrain at a rate of a thousand times per second and make suspension adjustments in a matter of milliseconds. For example, in one embodiment, sensors on the fork, rear axle, and/or frame read bump input at the wheel and the pitch angle of the bicycle 50, and send the obtained sensor data to the suspension controller 39 at a rate, such as but not limited to, 1,000 times per second. Thus, by placing sensors on the frame and/or proximate both wheels, the suspension controller 39 processes data from the terrain to constantly adjust the suspension for maximum efficiency and control. In one embodiment, suspension controller 39 includes a lithium ion battery as the main user interface and can be charged (e.g., via micro USB) on or off the bicycle 50.

For example, in one embodiment, the time of flight sensor detects a depression in the terrain. The depression data generated by the time of flight sensor is provided to the damping suspension controller 39 which will then compare the measurement data against the nominal value and generate a command to one or more of the active valves to change to the damping setting of one or more dampers when the nominal value is exceeded. For example, a compression damping setting is softened, a rebound damping speed setting is increased, etc.

In one embodiment, after detecting the depression, the time of flight sensor detects an upcoming rise in the terrain (e.g., the other side of the depression) and then makes a number of consistent measurements indicating a (relatively) smooth surface. In one embodiment, the rise in the terrain and the return to a constant distance measurement data generated by the time of flight sensor is provided to the damping suspension controller. When the damping suspension controller determines that the obstacle has been passed, in one embodiment, it will generate the command to the active valve to change to the damping setting of the one or more dampers back to the pre-obstacle compression and/or rebound settings. For example, the compression damping setting is stiffened, the rebound speed setting is decreased, etc.

In one embodiment, measurement type sensor 41 continuously and/or repeatedly measures a distance from the bicycle fork steerer tube, crown, or other fixed point to the lower stanchion, wheel, fender, ground, or other fixed point. By monitoring the distance between these points, the measurement type sensor can determine the suspension travel used and the speed at which the bicycle fork suspension compressed and rebounded.

In one embodiment, sensor 40 is a measurement type sensor such as an infrared based time of flight sensor and the like. In one embodiment, the measurement type sensor continuously and/or repeatedly measures a distance from the from the bottom shock eyelet, supporting shock substructure, or other fixed point to the top shock eyelet, supporting substructure, or other fixed point. By monitoring the distance between these points, the measurement type sensor can determine the shock suspension travel used and the speed at which the shock suspension compressed and rebounded.

Although four sensors are shown in FIG. 2, it should be appreciated that there may be only a single sensor or two or more sensors in operation. Moreover, in one embodiment, mobile device 95 is part of the active valve system 75.

Further, it should be appreciated that in one embodiment, information obtained by a vehicle can be shared with other vehicle(s). For example, in one embodiment, if a plurality of users are operating a number of vehicles within a certain range, information obtained by one, some, or all of the vehicles is shared with one, some, or all of the other vehicles. In one embodiment, the sharing is encrypted, as discussed herein, such that the information is only available to other vehicles (components, controllers, etc.) that are also using the encryption.

In one embodiment, the information is shared between components on one, some, or all of the other bikes such that, for example, the information from the lead vehicle (e.g., data from the sensor(s), controller, other smart/active components, and the like) is provided to the follow vehicle(s) (or automobiles, motorcycles, ATVs, snowmobiles, water vehicles, and the like) and used by, the follow vehicle(s) to adjust one or more suspension characteristics.

In one embodiment, the sharing of information includes raw sensor data. In one embodiment, the sharing of information includes data from the controller. For example, if the vehicles are different, e.g., motorcycle and truck, the sharing of raw sensor data allows one or more components associated with each vehicle to perform its own damping adjustments. In another example, when the vehicles are similar, the sharing of data from the controller includes specific tunes, settings, or the like.

In one embodiment, the sensors provide the obtained sensor data to suspension controller 39 which processes data from the terrain to constantly adjust the suspension for maximum efficiency and control. In one embodiment, using the sensor's pitch detection, the active valve system 75 can recognize when bicycle 50 climbing, traversing or descending.

In one embodiment, suspension controller 39 includes a lithium ion battery as the main user interface and can be charged (e.g., via micro USB) on or off the bicycle 50.

In one embodiment, one or a plurality of component(s) of the bicycle 50 are also smart component(s). Examples of the smart component(s) can include one or more of the forks, wheels, rear shocks, front shocks, handlebars, seat posts, pedals, cranks, and the like. In one embodiment, the smart component(s) will include connective features that allow them to communicate wired or wirelessly with suspension controller 39, mobile device 95, one or more sensors, and/or any other smart component(s) within transmission range (thereby becoming connected components). In one embodiment, the sensors, smart components, smart devices, controllers, valves, and the like may be interconnected or connected by (one or a combination of) wire, or wirelessly via systems such as near field communication (NFC), WAN, LAN, Bluetooth, WiFi, ANT, GARMIN® low power usage protocol, or any suitable power or signal transmitting mechanism, making them connected components.

By using a connected component, data (including real-time data) can be collected from the smart component by suspension controller 39. Depending upon the connected component, data such as telemetry attributes to provide angle, orientation, velocity, acceleration, RPM, operating temperature, and the like, can be obtained.

For example, a smart wheel is a connected component that is attached to the wheel (or wheels) to provide telemetry such as RPM, tire pressure, tire temperature, or the like to suspension controller 39. For example, in one embodiment, the smart component is a smart valve stem, a MEMS device, or the like coupled with the rim of the wheel.

An example of a smart handlebar is a connected component that provides handlebar geometry information, handlebar dimensions, stress measurements, or the like. For example, in one embodiment, the smart component is a MEMS device coupled with the handlebar.

An example of a smart seat post is connected component that provides geometry information such as seat height, seat pitch, roll, yaw, seat forward or aft location, weight on the seat, or the like. For example, in one embodiment, the smart component is a MEMS device coupled with the seat post.

An example of a smart pedal is connected component that provides telemetry such as RPM's, push and pull pressure, left side versus right side performance data (e.g., a stronger force on the right pedal or left pedal, in the up or down direction), or the like. For example, in one embodiment, the smart component is a MEMS device or other sensor type coupled with the pedal(s).

An example of a smart crank set is connected component that provides telemetry such as RPM's, chain tension, chain temperature, internal crank temperature, bearing operation, or the like. For example, in one embodiment, the smart component is a MEMS device coupled with the crank set.

Figure 3:
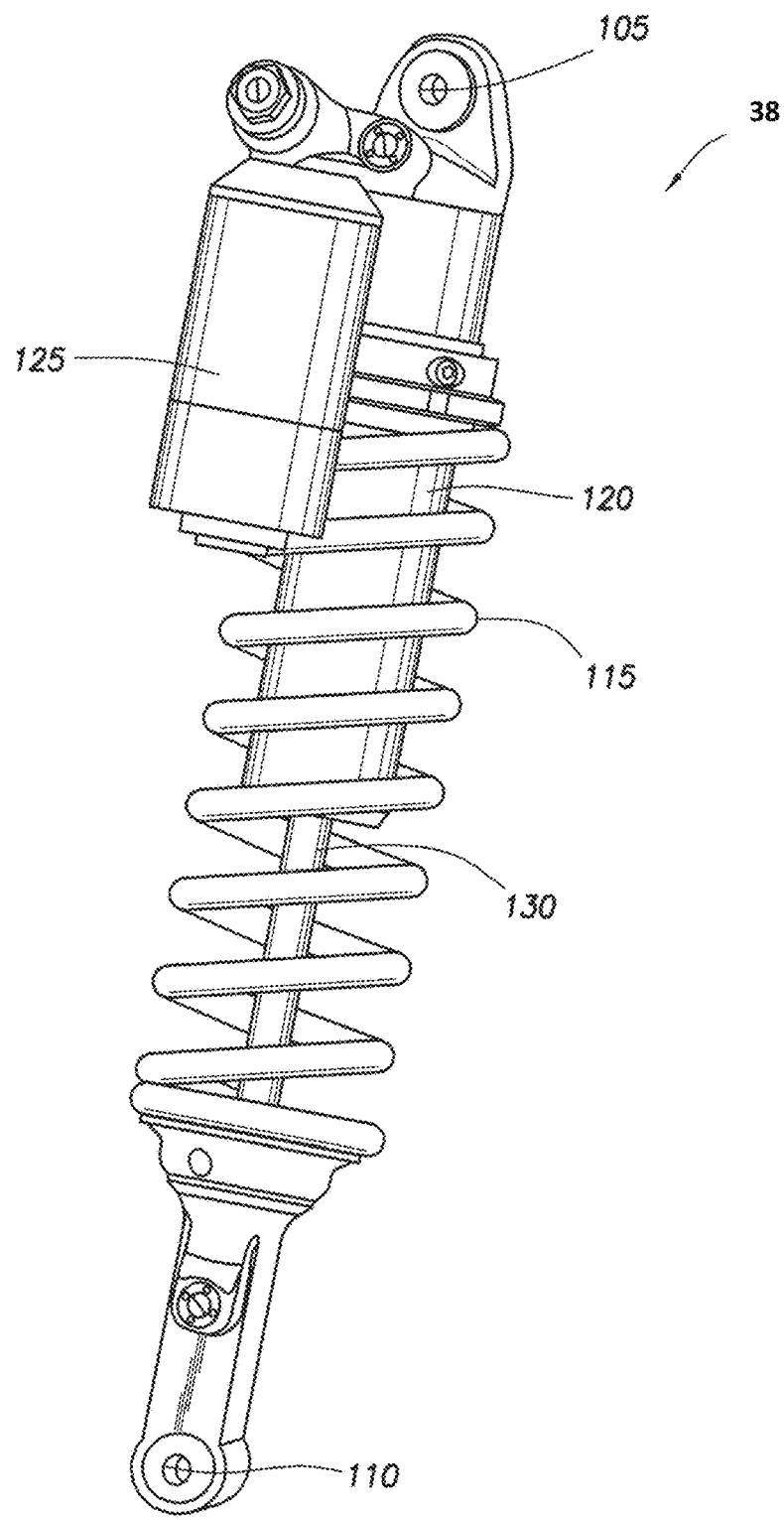
FIG. 3 is a perspective view of a rear damping assembly including a damper, external reservoir, and helical spring, in accordance with an embodiment.

FIG. 3 is a perspective view of an active valve damper 38. In one embodiment, active valve damper 38 includes eyelets 105 and 110, damper housing 120, helical spring 115, piston shaft 130, and piggyback (or external reservoir 125). In one embodiment, external reservoir 125 is described in U.S. Pat. No. 7,374,028 the content of which is entirely incorporated herein by reference.

In one embodiment, the damper housing 120 includes a piston and chamber and the external reservoir 125 includes a floating piston and pressurized gas to compensate for a reduction in volume in the main damper chamber of the damping assembly 38 as the piston shaft 130 moves into the damper body. Fluid communication between the main chamber of the damper and the external reservoir 125 may be via a flow channel including an adjustable needle valve. In its basic form, the damper works in conjunction with the helical spring and controls the speed of movement of the piston shaft by metering incompressible fluid from one side of the damper piston to the other, and additionally from the main chamber to the reservoir, during a compression stroke (and in reverse during the rebound or extension stroke).

Although a coil sprung damping assembly is shown in FIG. 3, this is provided as one embodiment and for purposes of clarity. In another embodiment, the active valve damper 38 is a different type such as, but not limited to, an air sprung fluid damper assembly, a stand-alone fluid damper assembly, and the like.

Example Active Valve

Figure 4:
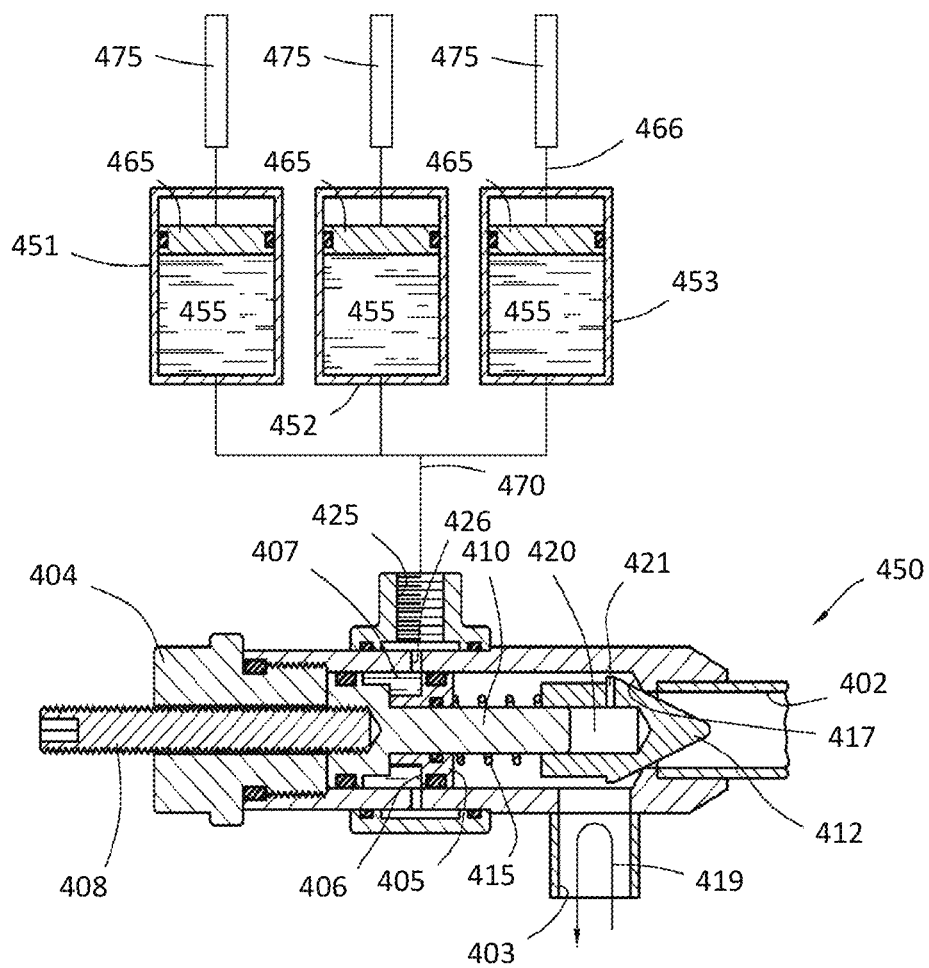
FIG. 4 is an enlarged section view showing an active valve and a plurality of valve operating cylinders in selective communication with an annular piston surface of the active valve, in accordance with an embodiment.

Referring now to FIG. 4, an enlarged view of an active valve 450 is shown in accordance with an embodiment. Although FIG. 4 shows the active valve 450 in a closed position (e.g. during a rebound stroke of the damper), the following discussion also includes the opening of active valve 450. Active valve 450 includes a valve body 404 housing a movable piston 405 which is sealed within the body. The piston 405 includes a sealed chamber 407 adjacent an annular piston surface 406 at a first end thereof. The chamber 407 and annular piston surface 406 are in fluid communication with a port 425 accessed via opening 426. Two additional fluid communication points are provided in the body including orifice 402 and orifice 403 for fluid passing through the active valve 450.

Extending from a first end of the piston 405 is a shaft 410 having a cone shaped member 412 (other shapes such as spherical or flat, with corresponding seats, will also work suitably well) disposed on an end thereof. The cone shaped member 412 is telescopically mounted relative to, and movable on, the shaft 410 and is biased toward an extended position due to a spring 415 coaxially mounted on the shaft 410 between the cone shaped member 412 and the piston 405. Due to the spring biasing, the cone shaped member 412 normally seats itself against a seat 417 formed in an interior of the valve body 404.

As shown, the cone shaped member 412 is seated against seat 417 due to the force of the spring 415 and absent an opposite force from fluid entering the active valve 450 along orifice 402. As cone shaped member 412 telescopes out, a gap 420 is formed between the end of the shaft 410 and an interior of cone shaped member 412. A vent 421 is provided to relieve any pressure formed in the gap. With a fluid path through the active valve 450 (from 403 to 402) closed, fluid communication is substantially shut off from the rebound side of the cylinder into the valve body (and hence to the compression side) and its "dead-end" path is shown by arrow 419.

In one embodiment, there is a manual pre-load adjustment on the spring 415 permitting a user to hand-load or un-load the spring using a threaded member 408 that transmits motion of the piston 405 towards and away from the conical member, thereby changing the compression on the spring 415.

Also shown in FIG. 4 is a plurality of valve operating cylinders 451, 452, 453. In one embodiment, the cylinders each include a predetermined volume of fluid 455 that is selectively movable in and out of each cylindrical body through the action of a separate corresponding piston 465 and rod 466 for each cylindrical body. A fluid path 470 runs between each cylinder and port 425 of the valve body where annular piston surface 406 is exposed to the fluid.

Because each cylinder has a specific volume of substantially incompressible fluid and because the volume of the sealed chamber 407 adjacent the annular piston surface 406 is known, the fluid contents of each cylinder can be used, individually, sequentially or simultaneously to move the piston a specific distance, thereby effecting the damping characteristics of the system in a relatively predetermined and precise way.

While the cylinders 451-453 can be operated in any fashion, in the embodiment shown each piston 465 and rod 466 is individually operated by a solenoid 475 and each solenoid, in turn, is operable from a remote location of the vehicle, like a cab of a motor vehicle or even the handlebar area of a motor or bicycle (not shown). Electrical power to the solenoids 475 is available from an existing power source of a vehicle or is supplied from its own source, such as on-board batteries. Because the cylinders may be operated by battery or other electric power or even manually (e.g. by syringe type plunger), there is no requirement that a soequipped suspension rely on any pressurized vehicle hydraulic system (e.g. steering, brakes) for operation. Further, because of the fixed volume interaction with the bottom out valve there is no issue involved in stepping from hydraulic system pressure to desired suspension bottom out operating pressure.

In one embodiment, e.g., when active valve 450 is in the damping-open position, fluid flow through orifice 402 provides adequate force on the cone shaped member 412 to urge it backwards, at least partially loading the spring 415 and creating a fluid flow path from the orifice 402 into and through orifice 403.

The characteristics of the spring 415 are typically chosen to permit active valve 450 to open at a predetermined pressure, with a predetermined amount of control pressure applied to port 425. For a given spring 415, higher control pressure at port 425 will result in higher pressure required to open the active valve 450 and correspondingly higher damping resistance in orifice 402. In one embodiment, the control pressure at port 425 is raised high enough to effectively "lock" the active valve closed resulting in a substantially rigid compression damper (particularly true when a solid damping piston is also used).

In one embodiment, the valve is open in both directions when the cone shaped member 412 is "topped out" against valve body 404. In another embodiment however, when the valve piston 405 is abutted or "topped out" against valve body 404 the spring 415 and relative dimensions of the active valve 450 still allow for the cone shaped member 412 to engage the valve seat 417 thereby closing the valve. In such embodiment backflow from the rebound side to the compression side is always substantially closed and cracking pressure from flow along orifice 402 is determined by the pre-compression in the spring 415. In such embodiment, additional fluid pressure may be added to the inlet through port 425 to increase the cracking pressure for flow along orifice 402 and thereby increase compression damping. It is generally noteworthy that while the descriptions herein often relate to compression damping and rebound shut off, some or all of the channels (or channel) on a given suspension unit may be configured to allow rebound damping and shut off or impede compression damping.

While the examples illustrated relate to manual operation and automated operation based upon specific parameters, in various embodiments, active valve 450 can be remotely-operated and can be used in a variety of ways with many different driving and road variables and/or utilized at any point during use of a vehicle. In one example, active valve 450 is controlled based upon vehicle speed in conjunction with the angular location of the vehicle's steering wheel. In this manner, by sensing the steering wheel turn severity (angle of rotation and rotational velocity), additional damping (by adjusting the corresponding size of the opening of orifice 402 by causing cone shaped member 412 to open, close, or partially close orifice 402) can be applied to one shock assembly or one set of vehicle shock assemblies on one side of the vehicle (suitable for example to mitigate cornering roll) in the event of a sharp turn at a relatively high speed.

In another example, a transducer, such as an accelerometer, measures other aspects of the vehicle's suspension system, like axle force and/or moments applied to various parts of the vehicle, like steering tie rods, and directs change to position of active valve 450 (and corresponding change to the working size of the opening of orifice 402 by causing cone shaped member 412 to open, close, or partially close orifice 402) in response thereto. In another example, active valve 450 is controlled at least in part by a pressure transducer measuring pressure in a vehicle tire and adding damping characteristics to some or all of the wheels (by adjusting the working size of the opening of orifice 402 by causing cone shaped member 412 to open, close, or partially close orifice 402) in the event of, for example, an increased or decreased pressure reading.

In one embodiment, active valve 450 is controlled in response to braking pressure (as measured, for example, by a brake pedal (or lever) sensor or brake fluid pressure sensor or accelerometer). In still another example, a parameter might include a gyroscopic mechanism that monitors vehicle trajectory and identifies a "spin-out" or other loss of control condition and adds and/or reduces damping to some or all of the vehicle's dampers (by adjusting the working size of the opening of orifice 402 by causing cone shaped member 412 to open, close, or partially close orifice 402 chambers) in the event of a loss of control to help the operator of the vehicle to regain control.

For example, active valve 450, when open, permits a first flow rate of the working fluid through orifice 402. In contrast, when active valve 450 is partially closed, a second flow rate of the working fluid though orifice 402 occurs. The second flow rate is less than the first flow rate but greater than no flow rate. When active valve 450 is completely closed, the flow rate of the working fluid though orifice 402 is statistically zero.

In one embodiment, instead of (or in addition to) restricting the flow through orifice 402, active valve 450 can vary a flow rate through an inlet or outlet passage within the active valve 450, itself. See, as an example, the electronic valve of FIGS. 2-4 of U.S. Pat. No. 9,353,818 which is incorporated by reference herein, in its entirety, as further example of different types of "electronic" or "active" valves). Thus, the active valve 450, can be used to meter the working fluid flow (e.g., control the rate of working fluid flow) with/or without adjusting the flow rate through orifice 402.

Due to the active valve 450 arrangement, a relatively small solenoid (using relatively low amounts of power) can generate relatively large damping forces. Furthermore, due to incompressible fluid inside the active valve damper 38, damping occurs as the distance between cone shaped member 412 and orifice 402 is reduced. The result is a controllable damping rate. Certain active valve features are described and shown in U.S. Pat. Nos. 8,627,932; 8,857,580; 9,033,122; 9,120,362; and 9,239,090 which are incorporated herein, in their entirety, by reference.

It should be appreciated that when the body 404 rotates in a reverse direction than that described above and herein, the cone shaped member 412 moves away from orifice 402 providing at least a partially opened fluid path.

Figure 5:
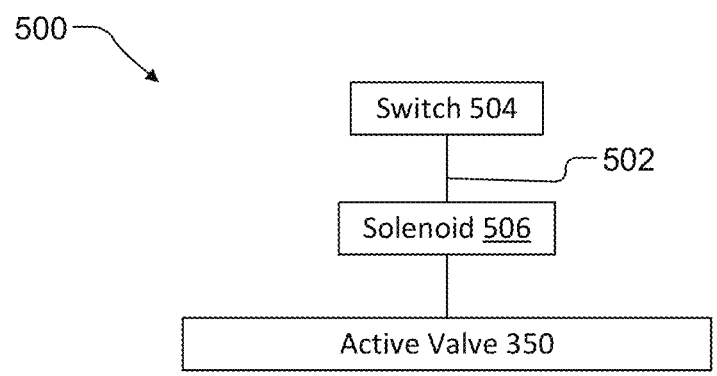
FIG. 5 is a schematic diagram showing a control arrangement for an active valve, in accordance with an embodiment.

FIG. 5 is a schematic diagram showing a control arrangement 500 for a remotely-operated active valve 450. As illustrated, a signal line 502 runs from a switch 504 to a solenoid 506. Thereafter, the solenoid 506 converts electrical energy into mechanical movement and rotates body 404 within active valve 450, In one embodiment, the rotation of body 404 causes an indexing ring consisting of two opposing, outwardly spring-biased balls to rotate among indentions formed on an inside diameter of a lock ring.

As the body 404 rotates, cone shaped member 412 at an opposite end of the valve is advanced or withdrawn from an opening in orifice 402. For example, the body 404 is rotationally engaged with the cone shaped member 412. A male hex member extends from an end of the body 404 into a female hex profile bore formed in the cone shaped member 412. Such engagement transmits rotation from the body 404 to the cone shaped member 412 while allowing axial displacement of the cone shaped member 412 relative to the body 404. Therefore, while the body does not axially move upon rotation, the threaded cone shaped member 412 interacts with mating threads formed on an inside diameter of the bore to transmit axial motion, resulting from rotation and based on the pitch of the threads, of the cone shaped member 412 towards or away from an orifice 402, between a closed position, a partially open position, and a fully or completely open position.

Adjusting the opening of orifice 402 modifies the flowrate of the fluid through active valve 450 thereby varying the stiffness of a corresponding active valve damper 38. While FIG. 5 is simplified and involves control of a single active valve 450, it will be understood that any number of active valves corresponding to any number of fluid channels (e.g., bypass channels, external reservoir channels, bottom out channels, etc.) for a corresponding number of vehicle suspension dampers are used alone or in combination. That is, the one or more active valves are operated simultaneously or separately depending upon needs in a vehicular suspension system.

For example, a suspension damper will have one, a combination of, or each of an active valve(s): for a bottom out control, an internal bypass, for an external bypass, for a fluid conduit to the external reservoir 125, etc. In other words, anywhere there is a fluid flow path within the active valve damper 38, an active valve is used. Moreover, in one embodiment, the active valve is alone or used in combination with other active valves at other fluid flow paths to automate one or more of the damping performance characteristics of the damping assembly. In one embodiment, additional switches permit individual operation of separate active bottom out valves.

Figure 6:
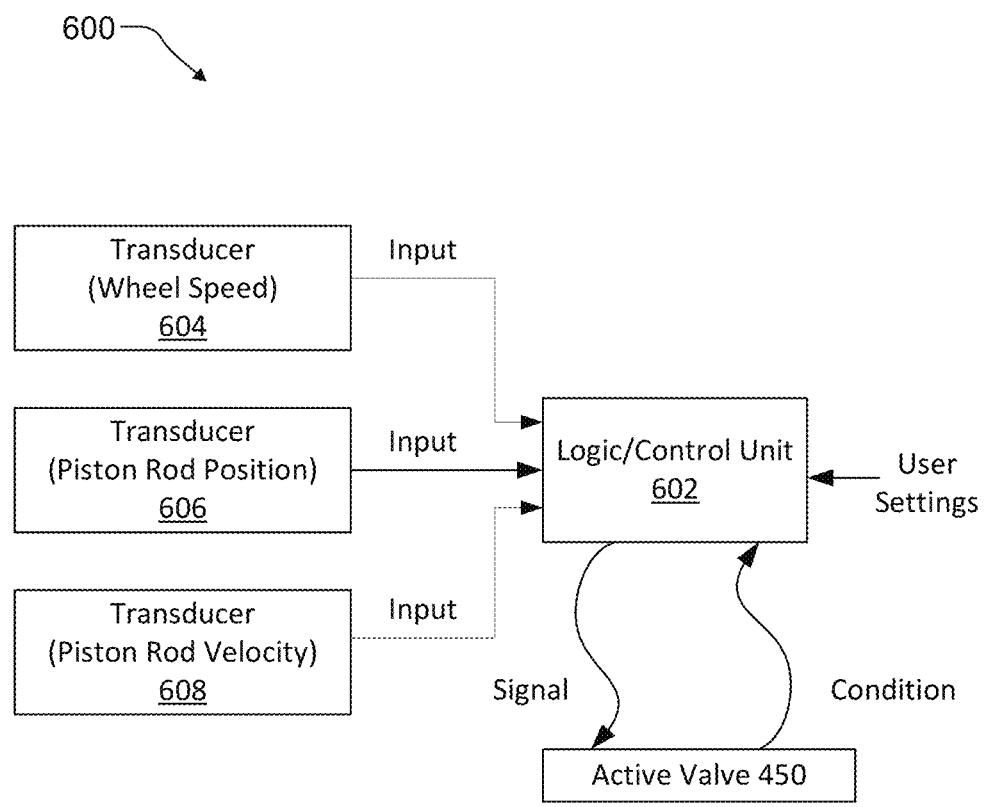
FIG. 6 is a schematic diagram of a control system based upon any or all of vehicle speed, damper rod speed, and damper rod position, in accordance with an embodiment.

In addition to, or in lieu of, the simple, switch-operated remote arrangement of FIG. 5, the remotely-operable active valve 450 can be operated automatically based upon one or more driving conditions, and/or automatically or manually utilized at any point during use of a vehicle. FIG. 6 shows a schematic diagram of a control system 600 based upon any or all of vehicle speed, damper rod speed, and damper rod position. One embodiment of the arrangement of FIG. 6 is designed to automatically increase damping in a shock assembly in the event a damper rod reaches a certain velocity in its travel towards the bottom end of a damper at a predetermined speed of the vehicle.

In one embodiment, the control system 600 adds damping (and control) in the event of rapid operation (e.g. high rod velocity) of the active valve damper 38 to avoid a bottoming out of the damper rod as well as a loss of control that can accompany rapid compression of a shock assembly with a relative long amount of travel. In one embodiment, the control system 600 adds damping (e.g., adjusts the size of the opening of orifice 402 by causing cone shaped member 412 to open, close, or partially close orifice 402) in the event that the rod velocity in compression is relatively low but the rod progresses past a certain point in the travel.

Such configuration aids in stabilizing the vehicle against excessive low-rate suspension movement events such as cornering roll, braking and acceleration yaw and pitch and "g-out."

FIG. 6 illustrates, for example, a control system 600 including three variables: wheel speed, corresponding to the speed of a vehicle component (measured by wheel speed transducer 604), piston rod position (measured by piston rod position transducer 606), and piston rod velocity (measured by piston rod velocity transducer 608). Any or all of the variables shown may be considered by logic unit 602 in controlling the solenoids or other motive sources coupled with active valve 450 for changing the working size of the opening of orifice 402 by causing cone shaped member 412 to open, close, or partially close orifice 402. Any other suitable vehicle operation variable may be used in addition to or in lieu of the variables discussed herein, such as, for example, piston rod compression strain, eyelet strain, vehicle mounted accelerometer (or tilt/inclinometer) data or any other suitable vehicle or component performance data.

In one embodiment, the piston's position within the damping chamber is determined using an accelerometer to sense modal resonance of the suspension damper or other connected suspension element such as the tire, wheel, or axle assembly. Such resonance will change depending on the position of the piston and an on-board processor (computer) is calibrated to correlate resonance with axial position. In one embodiment, a suitable proximity sensor or linear coil transducer or other electro-magnetic transducer is incorporated in the damping chamber to provide a sensor to monitor the position and/or speed of the piston (and suitable magnetic tag) with respect to a housing of the suspension damper.

In one embodiment, the magnetic transducer includes a waveguide and a magnet, such as a doughnut (toroidal) magnet that is joined to the cylinder and oriented such that the magnetic field generated by the magnet passes through the rod and the waveguide. Electric pulses are applied to the waveguide from a pulse generator that provides a stream of electric pulses, each of which is also provided to a signal processing circuit for timing purposes. When the electric pulse is applied to the waveguide, a magnetic field is formed surrounding the waveguide. Interaction of this field with the magnetic field from the magnet causes a torsional strain wave pulse to be launched in the waveguide in both directions away from the magnet. A coil assembly and sensing tape is joined to the waveguide. The strain wave causes a dynamic effect in the permeability of the sensing tape which is biased with a permanent magnetic field by the magnet. The dynamic effect in the magnetic field of the coil assembly due to the strain wave pulse, results in an output signal from the coil assembly that is provided to the signal processing circuit along signal lines.

By comparing the time of application of a particular electric pulse and a time of return of a sonic torsional strain wave pulse back along the waveguide, the signal processing circuit can calculate a distance of the magnet from the coil assembly or the relative velocity between the waveguide and the magnet. The signal processing circuit provides an output signal, which is digital or analog, proportional to the calculated distance and/or velocity. A transducer-operated arrangement for measuring piston rod speed and velocity is described in U.S. Pat. No. 5,952,823 and that patent is incorporated by reference herein in its entirety.

While transducers located at the suspension damper measure piston rod velocity (piston rod velocity transducer 608), and piston rod position (piston rod position transducer 606), a separate wheel speed transducer 604 for sensing the rotational speed of a wheel about an axle includes housing fixed to the axle and containing therein, for example, two permanent magnets. In one embodiment, the magnets are arranged such that an elongated pole piece commonly abuts first surfaces of each of the magnets, such surfaces being of like polarity. Two inductive coils having flux-conductive cores axially passing therethrough abut each of the magnets on second surfaces thereof, the second surfaces of the magnets again being of like polarity with respect to each other and of opposite polarity with respect to the first surfaces. Wheel speed transducers are described in U.S. Pat. No. 3,986,118 which is incorporated herein by reference in its entirety.

In one embodiment, as illustrated in FIG. 6, the logic unit 602 with user-definable settings receives inputs from piston rod position transducer 606, piston rod velocity transducer 608, as well as wheel speed transducer 604. Logic unit 602 is user-programmable and, depending on the needs of the operator, logic unit 602 records the variables and, then, if certain criteria are met, logic unit 602 sends its own signal to active valve 450 (e.g., the logic unit 602 is an activation signal provider) to cause active valve 450 to move into the desired state (e.g., adjust the flow rate by adjusting the distance between cone shaped member 412 and orifice 402). Thereafter, the condition, state, or position of active valve 450 is relayed back to logic unit 602 via an active valve monitor or the like.

In one embodiment, logic unit 602 shown in FIG. 6 assumes a single active valve 450 corresponding to a single orifice 402 of a single active valve damper 38, but logic unit 602 is usable with any number of active valves or groups of active valves corresponding to any number of orifices, or groups of orifices. For instance, the suspension dampers on one side of the vehicle can be acted upon while the vehicles other suspension dampers remain unaffected.

Figure 7:
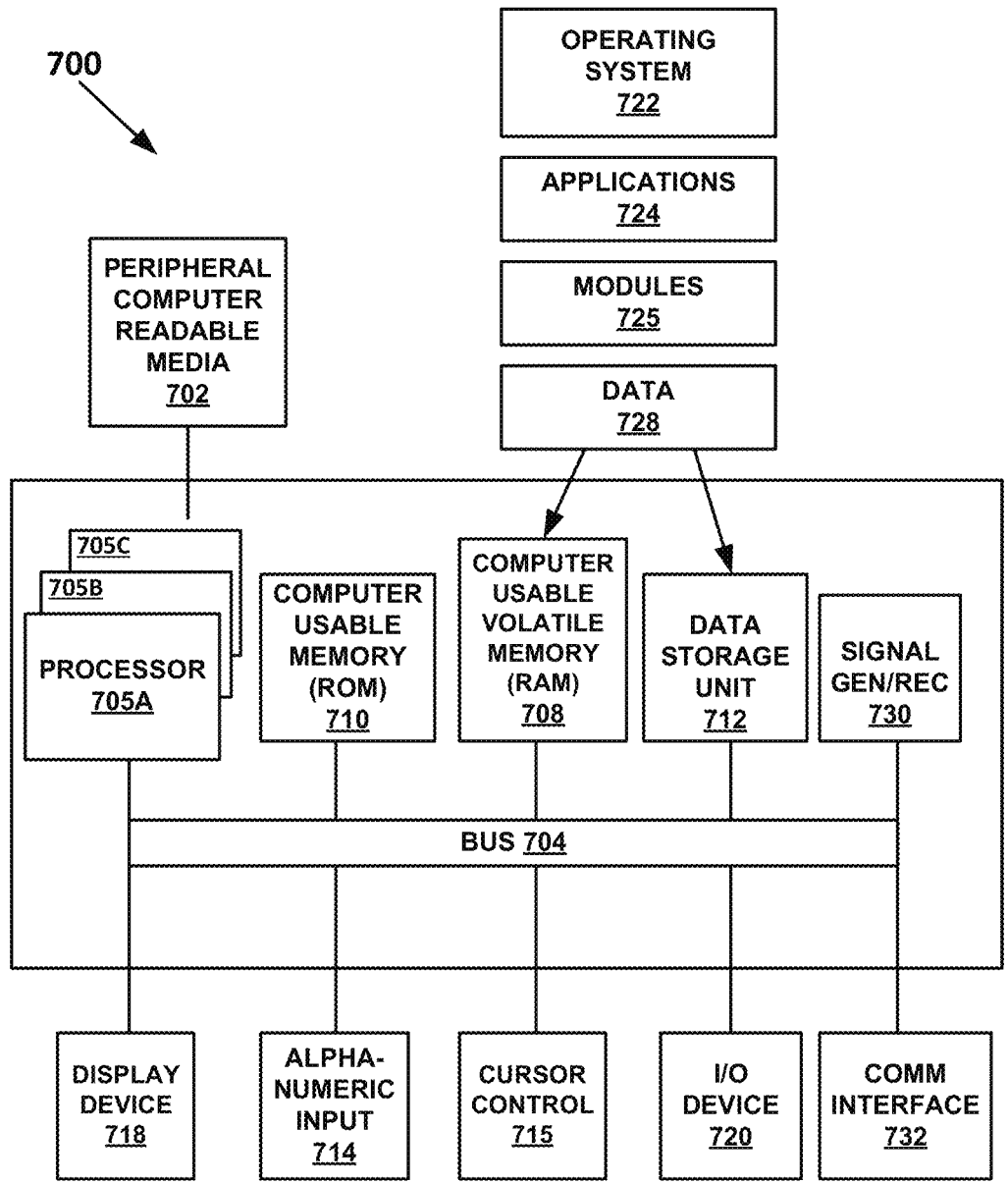
FIG. 7 is a block diagram of an example computer system with which or upon which various embodiments of the present invention may be implemented.

With reference now to FIG. 7, an example computer system 700 is shown. In the following discussion, computer system 700 is representative of a system or components that may be used with aspects of the present technology. In one embodiment, different computing environments will only use some of the components shown in computer system 700.

In general, suspension controller 39 can include some or all of the components of computer system 700. In different embodiments, suspension controller 39 can include communication capabilities (e.g., wired such as ports or the like, and/or wirelessly such as near field communication, Bluetooth, WiFi, or the like) such that some of the components of computer system 700 are found on suspension controller 39 while other components are ancillary but communicatively coupled thereto (such as a mobile device, tablet, computer system or the like). For example, in one embodiment, suspension controller 39 can be communicatively coupled with one or more different computing systems to allow a user (or manufacturer, tuner, technician, etc.) to adjust or modify any or all of the programming stored in suspension controller 39. In one embodiment, the programming includes computer-readable and computer-executable instructions that reside, for example, in non-transitory computer-readable medium (or storage media, etc.) of suspension controller 39 and/or computer system 700.

In one embodiment, computer system 700 includes an address/data/control bus 704 for communicating information, and a processor 705A coupled with bus 704 for processing information and instructions. As depicted in FIG. 7, computer system 700 is also well suited to a multi-processor environment in which a plurality of processors 705A, 705B, and 705C are present. Conversely, computer system 700 is also well suited to having a single processor such as, for example, processor 705A. Processors 705A, 705B, and 705C may be any of various types of microprocessors. Computer system 700 also includes data storage features such as a computer usable volatile memory 708, e.g., random access memory (RAM), coupled with bus 704 for storing information and instructions for processors 705A, 705B, and 705C. In one embodiment, computer system 700 can access peripheral computer readable media 702.

Computer system 700 also includes computer usable non-volatile memory 710, e.g., read only memory (ROM), coupled with bus 704 for storing static information and instructions for processors 705A, 705B, and 705C. Also present in computer system 700 is a data storage unit 712 (e.g., a magnetic disk drive, optical disk drive, solid state drive (SSD), and the like) coupled with bus 704 for storing information and instructions. Computer system 700 also can optionally include an alpha-numeric input device 714 including alphanumeric and function keys coupled with bus 704 for communicating information and command selections to processor 705A or processors 705A, 705B, and 705C. Computer system 700 also can optionally include a cursor control device 715 coupled with bus 704 for communicating user input information and command selections to processor 705A or processors 705A, 705B, and 705C. Cursor control device may be a touch sensor, gesture recognition device, and the like. Computer system 700 of the present embodiment can optionally include a display device 718 coupled with bus 704 for displaying information.

Referring still to FIG. 7, display device 718 can be a liquid crystal device, cathode ray tube, OLED, plasma display device or other display device suitable for creating graphic images and alpha-numeric characters recognizable to a user. Cursor control device 715 allows the computer user to dynamically signal the movement of a visible symbol (cursor) on a display screen of display device 718. Many implementations of cursor control device 715 are known in the art including a trackball, mouse, touch pad, joystick, non-contact input, gesture recognition, voice commands, bio recognition, and the like. In addition, special keys on alpha-numeric input device 714 capable of signaling movement of a given direction or manner of displacement. Alternatively, it will be appreciated that a cursor can be directed and/or activated via input from alpha-numeric input device 714 using special keys and key sequence commands.

Computer system 700 is also well suited to having a cursor directed by other means such as, for example, voice commands. Computer system 700 also includes an I/O device 720 for coupling computer system 700 with external entities. For example, in one embodiment, I/O device 720 is a modem for enabling wired or wireless communications between computer system 700 and an external network such as, but not limited to, the Internet or intranet. A more detailed discussion of the present technology is found below.

Referring still to FIG. 7, various other components are depicted for computer system 700. Specifically, when present, an operating system 722, applications 724, modules 725, and data 728 are shown as typically residing in one or some combination of computer usable volatile memory 708, e.g. random-access memory (RAM), and data storage unit 712. However, it is appreciated that in some embodiments, operating system 722 may be stored in other locations such as on a network or on a flash drive; and that further, operating system 722 may be accessed from a remote location via, for example, a coupling to the Internet. The present technology may be applied to one or more elements of described computer system 700.

Computer system 700 also includes one or more signal generating and receiving device(s) 730 coupled with bus 704 for enabling computer system 700 to interface with other electronic devices and computer systems. Signal generating and receiving device(s) 730 of the present embodiment may include wired serial adaptors, modems, and network adaptors, wireless modems, and wireless network adaptors, and other such communication technology. The signal generating and receiving device(s) 730 may work in conjunction with one (or more) communication interface 732 for coupling information to and/or from computer system 700. Communication interface 732 may include a serial port, parallel port, Universal Serial Bus (USB), Ethernet port, Bluetooth, thunderbolt, near field communications port, WiFi, Cellular modem, or other input/output interface. Communication interface 732 may physically, electrically, optically, or wirelessly (e.g., via radio frequency) couple computer system 700 with another device, such as a mobile phone, radio, or computer system.

Figure 8:
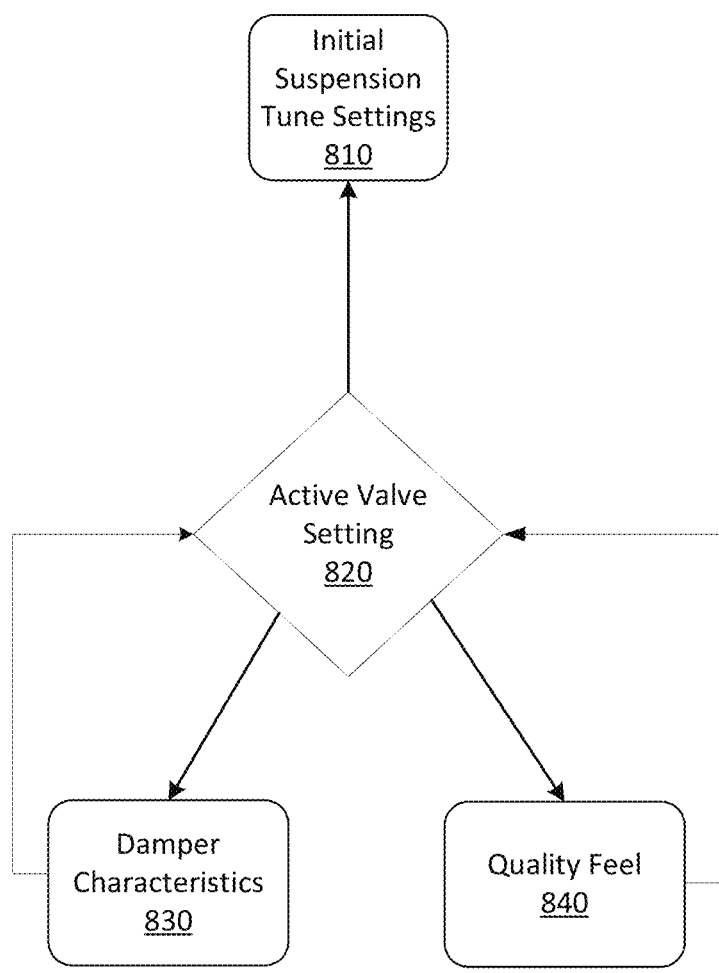
FIG. 8 is a flowchart of an embodiment for an active bottom out valve operation scheme, in accordance with an embodiment.

FIG. 8 is a flowchart 800 of an example method of operational incorporation for an active valve 450 operation in accordance with an embodiment. In one embodiment, during tuning of a suspension, the ride zone portion of the active valve damper 38 has a given range. This range can be adjusted by hardening or softening the active valve damper 38 settings in one or both of compression and rebound.

In one embodiment, by utilizing at least one active valve 450 in active valve damper 38, the tuning of the damping characteristics of the ride zone portion can be electronically vary based on terrain and/or rider behavior, etc.

At 810, the initial suspension tune setting is established (as discussed in further detail in the tune section herein). At 820, the active valve 450 is checked (as described in detail in FIGS. 5-7) for its present damping characteristic settings and is adjusted as needed.

At 830, the damper characteristics are established for the active tune and the damping of active valve 450 is adjusted accordingly.

At 840, the quality feel is evaluated and the damping of active valve 450 can be adjusted based on the quality feel.

Although a single flowchart is shown, it should be appreciated that in another embodiment, the flowchart 800 is similarly utilized by each of a plurality of active valves within the single active valve damper 38; by every of a plurality of active valves within the single active valve damper 38; by an active valve in each of a plurality of damping assemblies within a vehicle suspension; by a plurality of active valves in a plurality of damping assemblies within a vehicle suspension; by every active valve in a plurality of damping assemblies within a vehicle suspension; and by every active valve in every active valve damper 38 within a vehicle suspension.

Figure 9:
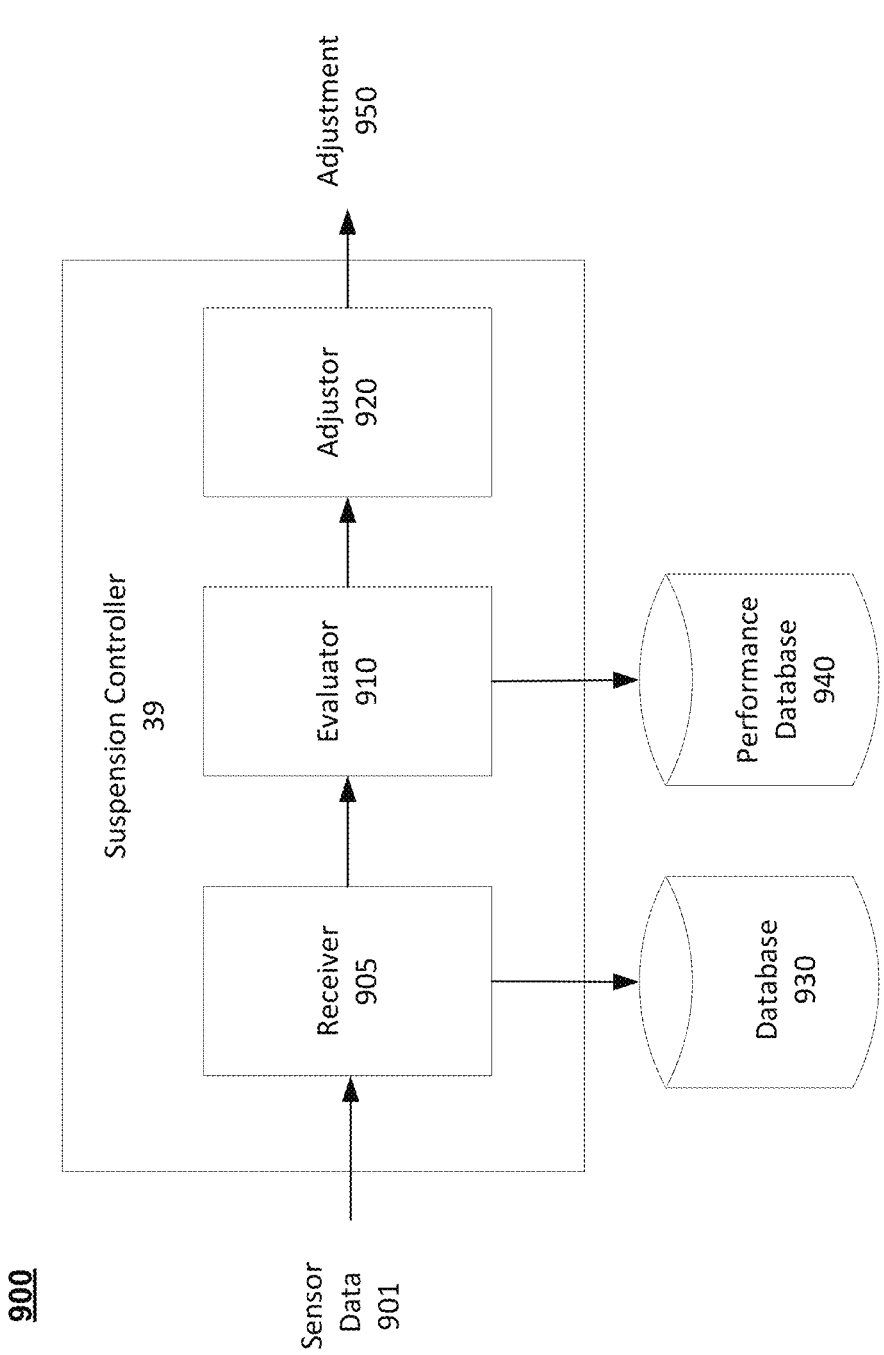
FIG. 9 is a block diagram of a suspension controller system, in accordance with an embodiment.

Referring now to FIG. 9, a block diagram of a suspension controller system 900 is shown in accordance with an embodiment. In one embodiment, suspension controller system 900 includes a suspension control device (e.g., suspension controller 39) and at least one active valve damper and one or more sensors coupled with a vehicle as shown in FIGS. 1 and 2. In one embodiment, suspension controller 39 includes a sensor data receiver 905, a sensor data evaluator 910, and an active valve damper adjustor 920.

In one embodiment, sensor data receiver 905 receives sensor data 901 from the one or more sensors (shown and described in FIGS. 1-2). In one embodiment, sensor data receiver 905 utilizes database 930 (or other memory solution) to collect and store the received sensor data 901.

In one embodiment, sensor data 901 includes sensor data such as accelerometer data, measurement data, and the like. In one embodiment, sensor data 901 is received from a bump sensor attached to one or both of the front and rear wheels that senses the bumps encountered by bicycle 50 (e.g., reading the terrain).

In one embodiment, sensor data 901 is received from a measurement type sensor (such as measurement type sensor 41) that continuously and/or repeatedly measures a distance from the bicycle fork steerer tube, crown, or other fixed point to the lower stanchion, wheel, fender, ground or other fixed point. By monitoring the distance between these points, the measurement type sensor can determine the suspension travel used and the speed at which the bicycle fork suspension compressed and rebounded.

In one embodiment, sensor data 901 is received from a measurement type sensor (such as sensor 40) that continuously and/or repeatedly measures a distance from the from the bottom shock eyelet, supporting shock substructure, or other fixed point to the top shock eyelet, supporting substructure, or other fixed point. By monitoring the distance between these points, the measurement type sensor can determine the shock suspension travel used and the speed at which the shock suspension compressed and rebounded.

In one embodiment, sensor data 901 is received from a plurality of sensor types as described herein.

In one embodiment, sensor data evaluator 910 determines a value of a repeating pattern identified in the sensor data, obtains a range of operational values for at least one damping characteristic of the active valve damper related to the repeating pattern, and adjusts the range of operational values based on the repeating pattern value. In one embodiment, the tunes including the operational values for at least one damping characteristic of the active valve damper are stored in performance database 940.

In one embodiment, active valve damper adjustor 920 is configured to monitor and adjust at least one damping characteristic of the at least one active valve damper (e.g., active valve damper 38). That is, active valve damper adjustor 920 will provide adjustment 950 commands to at least one active valve damper (e.g., active valve damper 38).

Evaluation Using Frequency

In one embodiment, the sensor data is evaluated by sensor data evaluator 910 using real-time fast Fourier transform (FFT) to calculate frequency data from the sensor signal for a certain period of time. In one embodiment, performance database 940 will include a number of pre-identified frequency signals that have been previously associated with different types of terrain. For example, a gravel road will have a unique signature (e.g., unique frequency signal).

In one embodiment, sensor data evaluator 910 will access the performance database 940 and correlate (or match, establish a level of similarity (e.g., 50% or greater match), and the like) the calculated frequency data from the sensor signal with one of the pre-identified frequencies signature associated with different types of terrain. For example, sensor data evaluator 910 will calculate the frequency data from the sensor signal and determine that the calculated frequency data reaches the threshold to consider it analogous to the pre-identified frequency signature associated with a gravel road.

In one embodiment, sensor data evaluator 910 will then access performance database 940 to obtain the appropriate damping settings for the gravel road. For example, the appropriate damping settings (e.g., gravel road settings) includes a bump threshold characteristic threshold such that the traveling along the gravel road will not be sufficient to trigger the suspension to open.

In one embodiment, sensor data evaluator 910 will compare the present damping characteristics, thresholds, and settings to determine if they are different from, or already set to, the gravel road settings. If the active valve damper 38 damping characteristics, thresholds, and settings are already set to the gravel road settings then no further actions is needed.

In one embodiment, if the present active valve damper 38 damping characteristics, thresholds, and settings are not already set to the gravel road settings, sensor data evaluator 910 will provide the gravel road damping characteristics, thresholds, and settings to active valve damper adjustor 920 which will provide the adjustment 950 information to active valve damper 38.

In one embodiment, if the present active valve damper 38 damping characteristics, thresholds, and settings are not already set to the gravel road settings, sensor data evaluator 910 will monitor the input frequency for a certain period of time to determine that the bike is remaining on the gravel road and is not just crossing a gravel road or encounter only a small patch of gravel road. For example, in one embodiment, the sensor data evaluator 910 evaluates the calculated frequency data for 1-5 seconds in order to establish that the bike is continuing to be operated on a gravel road environment. In one embodiment, the evaluation time period is shorter or longer depending upon type of ride (e.g., race, training, fun, etc.), user settings, performance requirements (e.g., less than 3 seconds on a gravel road will not cause a significant change to a rider's performance, but more than 3 seconds will begin a noticeable performance degradation, etc.), and the like.

In one embodiment, if the present active valve damper 38 damping characteristics, thresholds, and settings are not already set to the gravel road settings, after the evaluation time period is achieved, sensor data evaluator 910 will provide the gravel road damping characteristics, thresholds, and settings to active valve damper adjustor 920 which will provide the adjustment 950 information to active valve damper 38.

In one embodiment, sensor data evaluator 910 will continue to calculate frequency data from the sensor signal monitor to determine that the bike is remaining on the gravel road. If the input frequency changes to a different signature for a certain period of time sensor data evaluator 910 will repeat the above process to switch the damping characteristics, thresholds, and settings to the appropriate terrain settings. For example, if the sensor data evaluator 910 determines that the bike has returned to hard pack (following one or more embodiments above), sensor data evaluator 910 will provide the hard pack damping characteristics, thresholds, and settings to active valve damper adjustor 920 which will provide any adjustment 950 information to active valve damper 38.

Evaluation Using Acceleration and PSD

In one embodiment, the sensor data is evaluated by sensor data evaluator 910 to determine acceleration magnitude and real time power spectral density (PSD) determinations. In general, PSD measures the power content of the sensor data signal versus the frequency of the sensor data 901. In one embodiment, the acceleration is measured in g's while the PSD is measured in watts per hertz (W/Hz). In general, PSD provides a measurement of the amount of "punch" that the event (e.g., bump) has given to the suspension.

In one embodiment, sensor data evaluator 910 will determine the acceleration magnitude and PSD from the sensor data 901. Sensor data evaluator 910 will monitor the input to determine when both the acceleration magnitude and the PSD breach a pre-defined threshold. For example, in one embodiment, the threshold for acceleration magnitude is 5 g and the threshold for PSD is dependent upon user settings, manufacturer suggested, performance requirements and the like.

Once both the acceleration magnitude and the PSD breach their own pre-defined thresholds, sensor data evaluator 910 will provide the appropriate active valve damper 38 damping characteristics, thresholds, and settings to active valve damper adjustor 920 which will provide the adjustment 950 information to active valve damper 38.

In one embodiment, sensor data evaluator 910 will continue to calculate both the acceleration magnitude and the PSD to ensure that they are both remaining above their pre-defined thresholds. In one embodiment, if one or both of the acceleration magnitude and the PSD drop below their pre-defined thresholds, sensor data evaluator 910 will provide the previous damping characteristics, thresholds, and settings to active valve damper adjustor 920 which will provide the adjustment 950 information to active valve damper 38.

Evaluation Using Acceleration

In one embodiment, the sensor data is evaluated by sensor data evaluator 910 to include the derivative of acceleration (referred to herein as Jerk) from the acceleration data. Jerk is expressed in m/s3 (SI units) or standard gravities per second (g/s).

In one embodiment, sensor data evaluator 910 will continuously determine the Jerk and apply a variance approach to the Jerk to detect rapid changes in the signal.

In one embodiment, performance database 940 will include a number of pre-identified Jerk signatures that have been previously associated with different types of terrain. For example, a gravel road will have a unique Jerk signature that is distinguishable from a paved road Jerk signature, a hard pack Jerk signature, etc.

In one embodiment, sensor data evaluator 910 will access the performance database 940 and correlate (or match, establish a level of similarity (e.g., 70% or greater match), and the like) the calculated Jerk from the sensor signal with one of the pre-identified Jerk signatures associated with different types of terrain. For example, sensor data evaluator 910 will calculate the Jerk from the sensor signal and determine that the calculated Jerk reaches the threshold to consider it analogous to the pre-identified Jerk signature associated with a gravel road.

In one embodiment, sensor data evaluator 910 will then access performance database 940 to obtain the appropriate damping settings for the gravel road. For example, the appropriate damping settings (e.g., gravel road settings) includes a bump threshold characteristic threshold such that the traveling along the gravel road will not be sufficient to trigger the suspension to open.

In one embodiment, sensor data evaluator 910 will compare the present damping characteristics, thresholds, and settings to determine if they are different from, or already set to, the gravel road settings. If the active valve damper 38 damping characteristics, thresholds, and settings are already set to the gravel road settings then no further actions is needed.

In one embodiment, if the present active valve damper 38 damping characteristics, thresholds, and settings are not already set to the gravel road settings, sensor data evaluator 910 will provide the gravel road damping characteristics, thresholds, and settings to active valve damper adjustor 920 which will provide the adjustment 950 information to active valve damper 38.

In one embodiment, sensor data evaluator 910 will continue to calculate the Jerk to ensure that remains a match to the presently utilized gravel road Jerk signature. In one embodiment, if the real-time Jerk no longer matches the gravel road Jerk signature, sensor data evaluator 910 will perform another comparison and provide the new Jerk signature damping characteristics, thresholds, and settings to active valve damper adjustor 920 which will provide the adjustment 950 information to active valve damper 38.

In one embodiment, sensor data evaluator 910 will provide the gravel road damping characteristics, thresholds, and settings to active valve damper adjustor 920 which will provide the adjustment 950 information to active valve damper 38 as soon as the Jerk signature is identified.

In one embodiment, sensor data evaluator 910 will monitor the Jerk for a certain period of time before moving to the changed settings to ensure that the bike is remaining on the gravel road and is not just crossing a gravel road or encountering only a small patch of gravel road. For example, in one embodiment, the sensor data evaluator 910 evaluates the Jerk for 1-3 seconds in order to establish that the bike is continuing to be operated on a gravel road environment. In one embodiment, the evaluation time period is shorter or longer depending upon type of ride (e.g., race, training, fun, etc.), user settings, performance requirements (e.g., less than 2 seconds on a gravel road will not cause a significant change to performance, but more than 2 seconds will begin a noticeable performance degradation, etc.), and the like.

In one embodiment, if the present active valve damper 38 damping characteristics, thresholds, and settings are not already set to the gravel road settings, after the evaluation time period is achieved, sensor data evaluator 910 will provide the gravel road damping characteristics, thresholds, and settings to active valve damper adjustor 920 which will provide the adjustment 950 information to active valve damper 38.

Noise Floor Approach

In one embodiment, the vibration (e.g., sensor noise or noise not due to mechanical movement) coming from the surface of the ground has a certain acceleration noise which is a much higher frequency than a lower frequency when the sensor detects a discrete bump caused by hitting a rock or tree root (for example). This higher frequency noise floor creates an offset to the acceleration signal. In one embodiment, the frequency of bump input to the sensor is usually in the range of 1-50 Hz thus any frequency above 50 Hz is considered the sensor noise. In one embodiment, the frequency of bump input to the sensor is in the range of 1-30 Hz thus any frequency above 30 Hz is considered the sensor noise. In yet another embodiment, the frequency of bump input to the sensor is in the range of 1-30 Hz and any frequency above 50 Hz is considered the sensor noise. Although a number of examples are provided, it should be appreciated that in another embodiment, the actual values include a higher or lower range depending upon sensor metrics, manufacturer suggestions, performance requirements, rider preference, and the like.

For example, the bump threshold to change the suspension mode is set at approximately 5 g (or any other threshold setting selected by manufacturer, rider, or the like). However, while on the ride, the higher frequency noise floor is causing the sensor data evaluator 910 to continually determine a constant 3 g for acceleration magnitude (e.g., the road noise). Without adjustment, the sensor data evaluator 910 has active valve damper adjustor 920 send the adjustment 950 commands to active valve damper 38 whenever an acceleration event of greater than 2 g occurred (e.g., 3 g background noise plus 2.1 g event). This causes a softening of the suspension to occur well below the pre-set 5 g event threshold is met.

To overcome this problem, in one embodiment, sensor data evaluator 910 will modify the bump threshold value to be a value of 5 g+the higher frequency noise floor. For instance, using the above example, sensor data evaluator 910 continually determines a constant 3 g for the higher frequency noise floor acceleration magnitude (e.g., the road noise). As such, the sensor data evaluator 910 will adjust the bump threshold value to 8 g (e.g., 3 g floor noise+5 g threshold value). In so doing, the sensor data evaluator 910 has active valve damper adjustor 920 send the adjustment 950 commands to active valve damper 38 whenever an acceleration event of greater than 8 g was determined by sensor data evaluator 910.

In one embodiment, instead of sensor data evaluator 910 modifying the bump threshold value to be a value of 5 g+the higher frequency noise floor, sensor data evaluator 910 will filter out the higher frequency noise floor. For instance, using the above example, sensor data evaluator 910 continually determines a constant 3 g for the higher frequency noise floor acceleration magnitude (e.g., the road noise). As such, the sensor data evaluator 910 will filter out the 3 g noise floor while keeping the bump threshold value at the 5 g threshold value. In so doing, the sensor data evaluator 910 establishes a base line at the higher frequency noise floor and have active valve damper adjustor 920 send the adjustment 950 commands to active valve damper 38 whenever an acceleration event of greater than 5 g above the base line, was determined by sensor data evaluator 910.

In one embodiment, sensor data evaluator 910 will continue to calculate the higher frequency noise floor (over a given period of time) and continually adjust the base line, the bump threshold range, or the like based on the most recent higher frequency noise floor. For example, in one embodiment, sensor data evaluator 910 calculates the higher frequency noise floor average for a given period of time (such as every five minutes, two minutes, one minute, 30 seconds, n-minutes, n-seconds, etc.). The most recently determined higher frequency noise floor average is used for the time period required for the sensor data evaluator 910 to determine the next-in-time higher frequency noise floor average. Once the next-in-time higher frequency noise floor average was determined, it replaces the previous higher frequency noise floor average.

For example, in one embodiment, the higher frequency noise floor average is determined by sensor data evaluator 910 over a 2-minute time window. After the 2-minute time window ends, the higher frequency noise floor average is determined to be 2.2 g. During the next 2-minute time window, sensor data evaluator 910 adjusts the base line by filtering out 2.2 g from the acceleration signal data (or adjust the bump threshold range to 7.2 g), or the like. In addition, during the same time period, sensor data evaluator 910 will be monitoring the higher frequency noise floor.

At, about, or right after the closing of the 2-minute time window, sensor data evaluator 910 has a new next-in-time higher frequency noise floor average (for example, the average over the latest 2-minute time window was 1.5 g). This new average (1.5 g) is used over the next 2-minute time window; e.g., sensor data evaluator 910 adjusts the base line by filtering out 1.5 g from the acceleration signal data (or adjust the bump threshold range to 6.5 g), or the like; and the cycle continues to repeat.

In one embodiment, (e.g., in one or more of the above examples) instead of using a block of time approach, the sensor data evaluator 910 continually adjusts the higher frequency noise floor average over a rolling time period. In other words, the higher frequency noise floor is based on a rolling 2-minute average such that the higher frequency noise floor average is continually updated by sensor data evaluator 910. For example, in one embodiment, starting after 2-minutes of time, sensor data evaluator 910 sets the higher frequency noise floor at 1.8 g (e.g., the average of the measurements taken from time zero to 2-minutes). The rolling 2-minute average continues to be adjusted by throwing out measurements older than 2-minutes in the past and replacing them with the latest measurement. For example, at 5 minutes into the ride, the determined higher frequency noise floor is set at the average of the measurements taken from time 3-minutes to 5-minutes. At 21 minutes and 20 seconds into the ride, the determined higher frequency noise floor is set at the average of the measurements taken from time 19-minutes and 20-seconds to 21-minutes and 20-seconds. Etc.

In one embodiment, the first time period of the ride has no noise floor, has a noise floor average taken for the entirety of time until the first time period was completed, etc. Moreover, although 2-minutes is used herein, the time window may be larger or smaller and may be dependent upon type of ride (e.g., race, training, fun, etc.), user settings, performance requirements, manufacturer recommendation, or the like.

In one embodiment, the sensor data evaluator 910 will use one, some, a combination of different features of some or all of the different approaches, or all of the different approaches (e.g., evaluation using frequency, evaluation using acceleration and PSD, evaluation using acceleration, noise floor approach, etc.) to determine when the suspension should, or should not, be adjusted.

Figure 10:
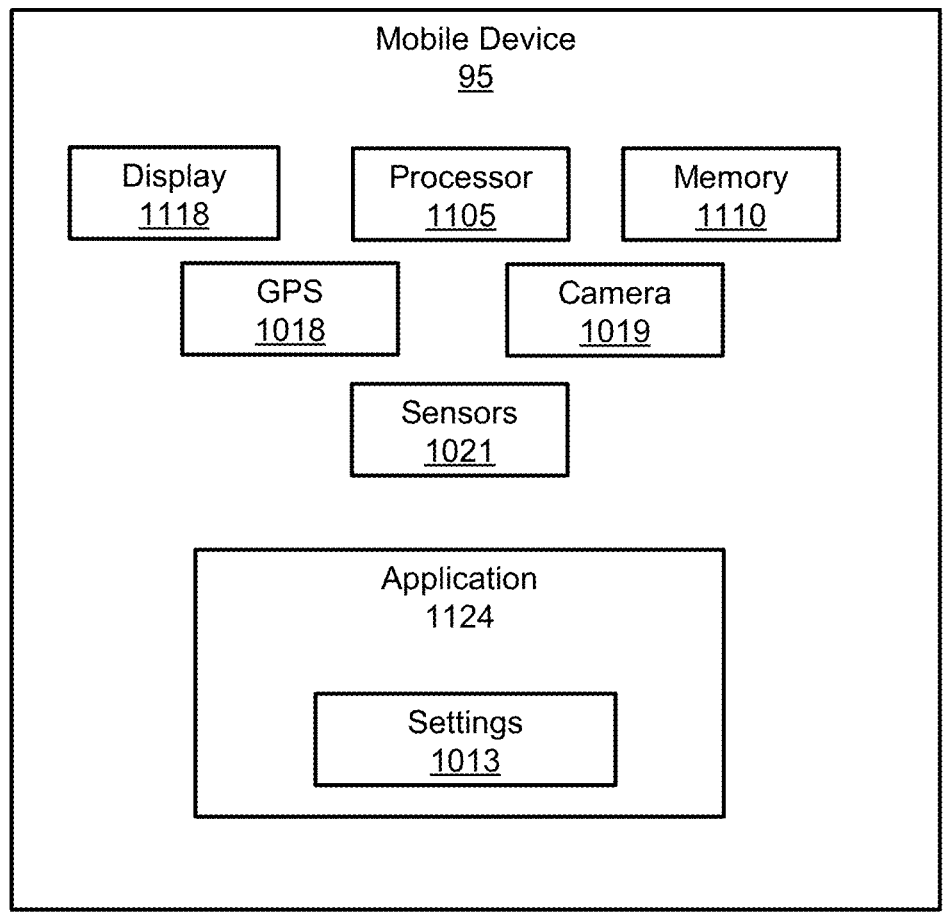
FIG. 10 is a block diagram of a mobile device, in accordance with an embodiment.

Referring now to FIG. 10, a block diagram of a mobile device 95 is shown. Although a number of components are shown as part of mobile device 95, it should be appreciated that other, different, more, or fewer components may be found on mobile device 95.

In general, mobile device 95 is an example of a smart device that is available for a user. In one embodiment, mobile device 95 is a mobile phone, a smart phone, a tablet, a smart watch, a piece of smart jewelry, smart glasses, or other user portable devices having wireless connectivity. For example, mobile device 95 is capable of broadcasting and receiving via at least one network, such as, but not limited to, WiFi, Cellular, Bluetooth, NFC, and the like. In one embodiment, mobile device 95 includes a display 1118, a processor 7055, a memory 1110, a GPS 1018, a camera 1019, and the like. In one embodiment, location information can be provided by GPS 1018. In one embodiment, the location information is enhanced by the broadcast range of an identified beacon, a WiFi hotspot, overlapped area covered by a plurality of mobile telephone signal providers, or the like. In one embodiment, instead of using GPS information, the location of mobile device 95 may be determined within a given radius, such as the broadcast range of an identified beacon, a WiFi hotspot, overlapped area covered by a plurality of mobile telephone signal providers, or the like. In one embodiment, geofences are used to define a given area and an alert or other indication is made when the mobile device 95 enters into or departs from a geofence.

Mobile device 95 includes sensors 1021 which can include one or more of audio, visual, motion, acceleration, altitude, GPS, and the like. Mobile device 95 also includes a vehicle setup application 1124 which is an electronic application that operates on mobile device 95. Vehicle setup application 1124 includes settings 1013. Although settings 1013 are shown as part of vehicle setup application 1124, it should be appreciated that in another embodiment settings 1013 are located in a different application operating on mobile device 95, at a remote storage system separate from mobile device 95, or the like.

Figure 11:
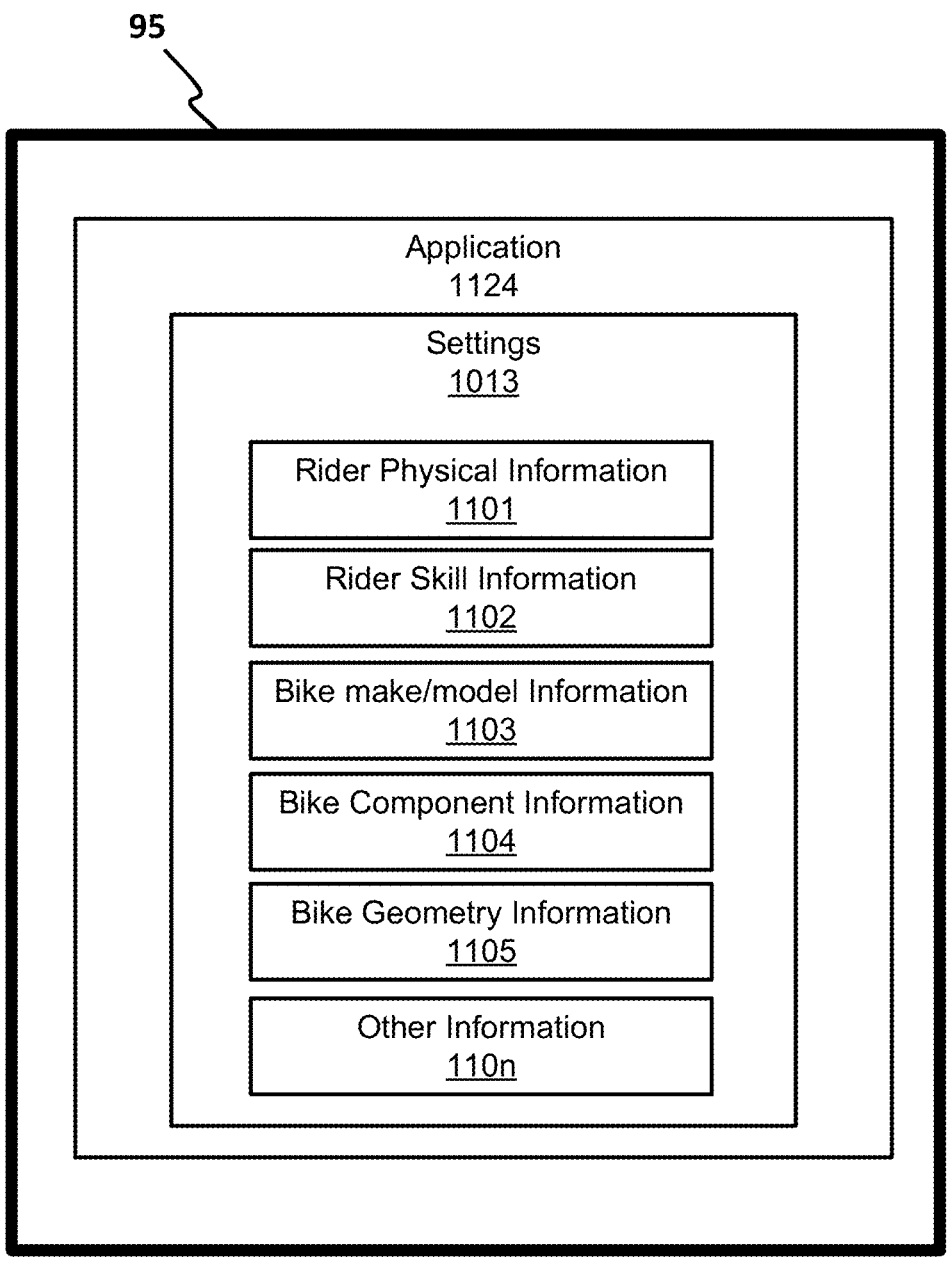
FIG. 11 is a block diagram of a mobile device display having a number of inputs shown for the application, in accordance with an embodiment.

Referring now to FIG. 11, a block diagram of a mobile device 95 display having a number of inputs are shown for the vehicle setup application 1124 in accordance with an embodiment. In general, the vehicle setup application 1124 operates on mobile device 95 and uses the communication capabilities of mobile device 95 to communicate with one or more active valves in the active valve system of the vehicle. In various embodiments, the communication is Bluetooth, near field communication (NFC), WiFi, or any other available wireless communication. In one embodiment, the communication is wired if the mobile device 95 is mounted on the handlebar assembly 36 and a communications cable is running from one or more of the active valve systems to the handlebars and plugged into mobile device 95.

In one embodiment, the vehicle setup application 1124 receives a number of inputs to help establish the settings for the provided tunes. In one embodiment, the inputs include, a rider physical information 1101 (e.g., one or a combination of features such as, but not limited to, rider height, weight, gender, age, body mass, body type, fitness level, heart rate, and the like). Rider skill information 1102, e.g., beginner, intermediate, advanced, professional, etc., or rider motivation (e.g., fun ride, race, workout, etc.), and the like. Bike make/model information 1103, such as, bike manufacturer, bike model, bike use, e.g., road, gravel, mountain, BMX, etc. bike component information 1104 such as, one or more components on the bike (full suspension, half suspension, gearing, weight, tires, wheels, manufacturer of components, etc.), and the like.

In one embodiment, the input to the vehicle setup application 1124 includes bike geometry information 1105 such as: seat height setting, seat pitch, seat offset, crank arm length, wheel diameter, handlebar width, handlebar offset (fore or aft), pedal type, and the like. In one embodiment, other information $110n$ categories are added to the inputs. In one embodiment, the inputs are more or fewer of the above categories, different categories, user selectable, application driven, and the like. The use of the described categories herein is provided for purposes of clarity.

In one embodiment, some or all of the above information is obtained by user input, by communication between the user's mobile device 95 and a networked device such as a scale, smart watch or other smart jewelry that monitors one or more user's biometrics (e.g., heart rate, body mass, temperature, etc.), one or more sensors on the vehicle, or the like. In one embodiment, the information is obtained by an image capture device (such as a camera) that obtains an image of the bike, a bike component, a 1D or 2D code on the bike or bike component, and the like. In one embodiment, the captured image(s) are then evaluated by the vehicle setup application 1124 (or other recognition capability) to make one or more bike specific measurement determinations therefrom, make one or more bike part specific component brand/model/year determination(s), make one or more bike brand/model/year determination(s), make one or more bike geometric determination(s) (e.g., seat height-from ground, seat height-from cranks, etc.; wheel diameter, type/brand/wear of tires, and the like).

In one embodiment, vehicle setup application 1124 allows the user to search, select, and upload one or more factory and/or customer suspension tunes.

In one embodiment, vehicle setup application 1124 can provide the rider with the tunes that correlate with one or more of the rider inputs provided to settings 1013. For example, there may be 5,000 tunes stored in the factory database. In one embodiment, instead of the user manually selecting from the 5,000 tunes, vehicle setup application 1124 will use the user inputs to automatically narrow the number of tunes down to only those that meet the user input criteria. For example, novice tunes, expert tunes, bike model/brand tunes, damping assembly types, and the like.

In one embodiment, vehicle setup application 1124 will also manage a number of bike profiles. For example, the user may have three different vehicles (a mountain bike, a road bike, and a quad). There may be different tunes downloaded to vehicle setup application 1124 for each of the three (or any number) of different vehicles. The user can select which vehicle she will be riding (e.g., the mountain bike), and the available tunes for the mountain bike will be presented by the vehicle setup application 1124 as shown and described in further detail in FIG. 12.

In one embodiment, vehicle setup application 1124 can also perform system diagnostics on the vehicle active valve system, can calibrate the vehicle active valve system, can provide firmware updates to one or more components of the vehicle active valve system, and the like.

In one embodiment, vehicle setup application 1124 on mobile device 95 can communicate directly with the active valve system and then provide the information to the rider via the mobile device display. In one embodiment, vehicle setup application 1124 can communicate with another device that provides the power to the active valve system (e.g., a Bosch Kiox HMI, or the like). In one embodiment, the device that provides power to the active valve system will also have a front mounted display that can present information from vehicle setup application 1124 to the rider. In one embodiment, the rider can change modes (while stopped, on-the-fly, or the like) via the vehicle setup application 1124 and/or by the Bosch handlebar button and Kiox screen. In one embodiment, A mode selected on the Kiox is reflected on the vehicle setup application 1124 and similarly, a mode selected in the vehicle setup application 1124 is reflected on the Kiox screen.

Figure 13:
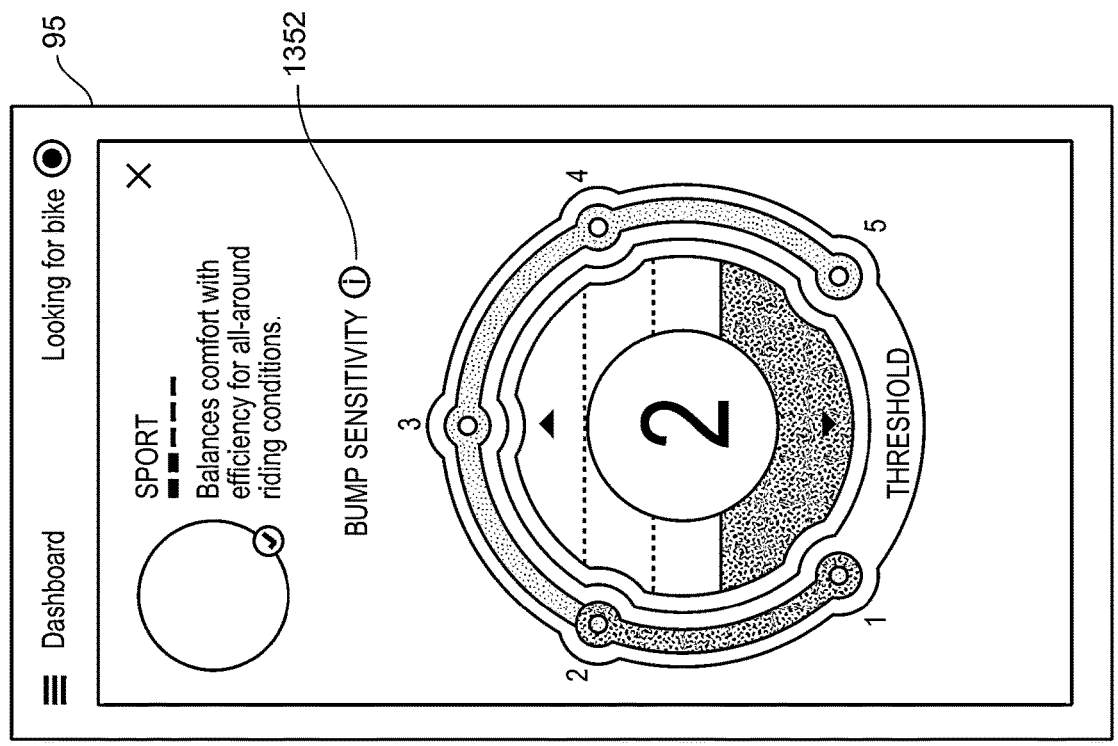
FIG. 13 is a screenshot of a user adjustable capability that is accessed when the user wants to change a tune in the application, in accordance with an embodiment.
Figure 12:
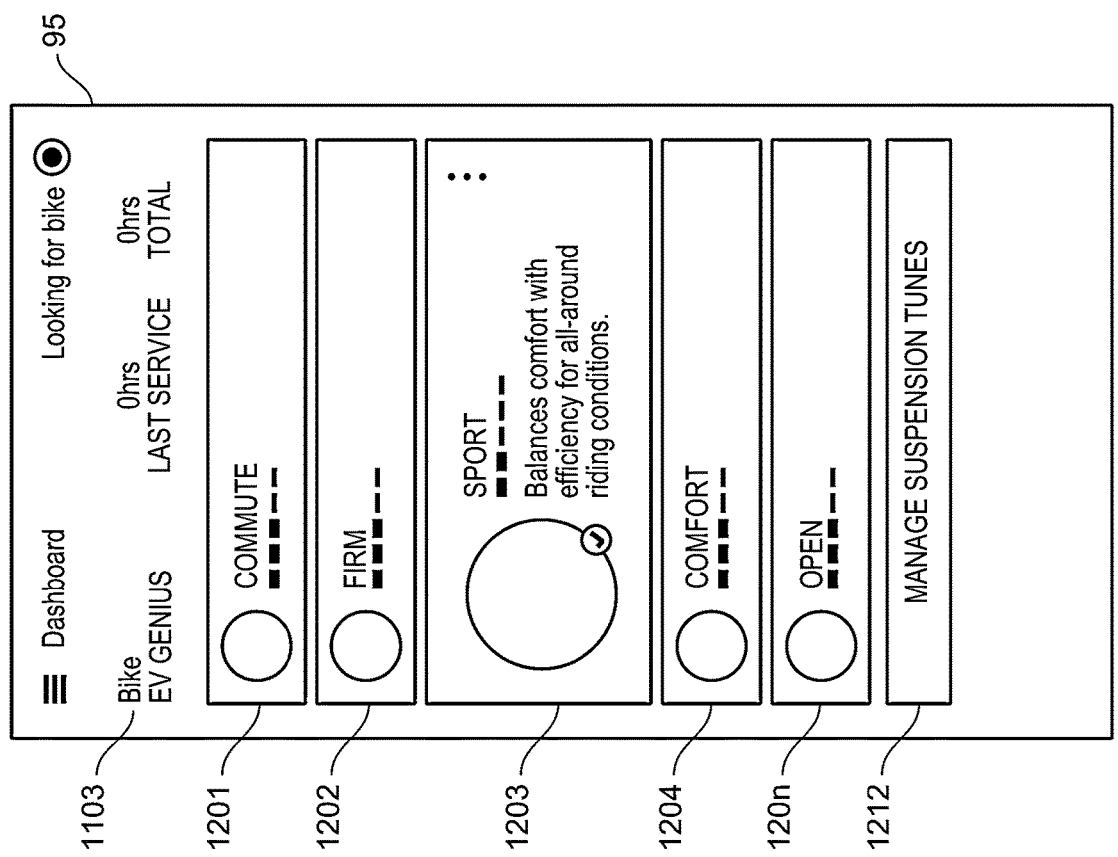
FIG. 12 is a screenshot of the application having a number of different tunes shown on a display, in accordance with an embodiment.

With reference now to FIGS. 12, a screenshot of the vehicle setup application 1124 having a number of different tunes 1201-120n is shown in accordance with an embodiment. FIG. 13 is a screenshot of a user adjustable capability that is accessed when the user wants to change a tune in accordance with an embodiment.

In FIG. 12, mobile device 95 displays the vehicle setup application 1124 that includes the bike make/model information 1103 and five different tunes 1201-120n. In one embodiment, the tunes include a commute tune 1201, a firm tune 1202, a sport tune 1203, a comfort tune 1204 and an open tune 1205. Although five tunes are shown, it should be appreciated that there may be more or fewer tunes. The use of five tunes herein is one embodiment and provided for purposes of clarity. Further, although four of the five tunes have specific names, it should be appreciated that in another embodiment, there may be all custom tunes, a number of differently modified sport tunes, or the like. For example, a rider may make a first comfort tune for road riding, a second comfort tune for trail riding, a third comfort tune for the racetrack, etc. Thus, the naming and or type of tunes is multi-faceted, and user or application driven.

In one embodiment, the tunes are different based on the inputs provided at FIG. 12 information such as rider skill level, bike type, one or more components on the bike, rider motivation, and the like. For example, a new rider receives one or more tunes that were set at a first level, while an expert rider (or intermediate rider) receives one or more tunes that were set at a second level. In one embodiment, the differentiation in tune settings occurs between bike types, e.g., a road bike likely (but may not necessarily) receive different automatic (or initial tune) settings that that of a gravel bike, mountain bike, etc.

When the user selects a mode (or tune), e.g., sport tune 1203 the tune includes a number of different suspension settings. For example, as shown in FIG. 13, sport tune 1203 has an initial bump sensitivity 1352 setting of 2 from a scale of 1 to 5. In one embodiment, the user will adjust the initial bump sensitivity 1352 to a new bump sensitivity (e.g., sensitivity level 3) which is either a firmer setting or a softer setting depending upon which way the sensitivity scale was ranked. In one embodiment, other suspension tune management bump sensitivity 1352 features include timers, coupling/decoupling front and/or rear dampers, incline angles, and the like.

Figure 14:
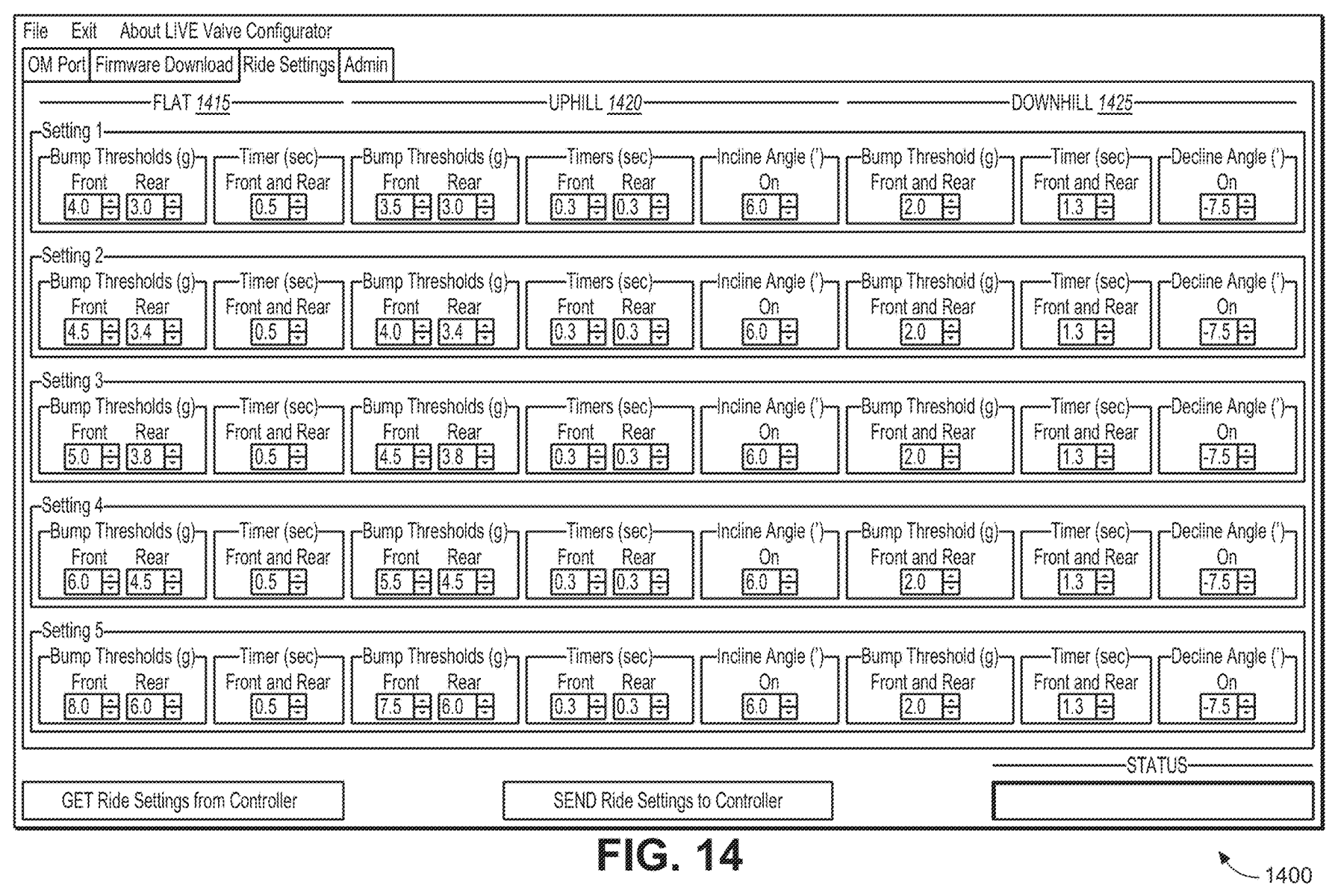

In one embodiment, as shown in FIG. 14, a screenshot of a ride settings management page, the manage suspension tunes 1212 includes modes such as flat, uphill and downhill bump settings.

The following is an example of the code for one modes (or tunes): In this case, sport mode.

```
slot:
    base_slot: 2
    id: 3
    name: [S, P, O, R, T, "\0", "\0", "\0", "\0", "\0", "\0", "\0", "\0", "\0",
           "\0", "\0", "\0", "\0", "\0", "\0", "\0", "\0", "\0", "\0", "\0", "\0",
           "\0", "\0", "\0", "\0", "\0"]
    threshold_index: 2
    timestamp: [0, 1]
threshold:
    bump_threshold:
    -   - [3000, 3500, 4000, 5000, 6000]
        - [2000, 2000, 2000, 2000, 2000]
        - [2500, 3000, 3500, 4500, 5500]
    -   - [2250, 2625, 3000, 3750, 4500]
        - [2000, 2000, 2000, 2000, 2000]
        - [2000, 2300, 2625, 3375, 4125]
slot_3_settings:
    mode:
        coupled_open_time:
            - [300, 300, 300, 300, 300]
            - [1300, 1300, 1300, 1300, 1300]
            - [0, 0, 0, 0, 0]
        decline_angle: [-600, -600, -600, -600, -600]
        decline_delay: [0, 0, 0, 0, 0]
        decline_hysteresis: [-300, -300, -300, -300, -300]
        decoupled_open_time:
        -   - [500, 500, 500, 500, 500]
            - [500, 500, 500, 500, 500]
            - [500, 500, 500, 500, 500]
        -   - [300, 300, 300, 300, 300]
            - [300, 300, 300, 300, 300]
            - [300, 300, 300, 300, 300]
        incline_angle: [600, 600, 600, 600, 600]
        incline_delay: [250, 250, 250, 250, 250]
        incline_hysteresis: [550, 550, 550, 550, 550]
        shock_control_style: 4
```

The mode (or tune) has a name (sport mode), a threshold index (0-5), a front bump threshold matrix: where the three rows are defined as climb (incline), flat (neutral), descend (decline) and the columns are related to the threshold index selection, and a rear bump threshold matrix: where the three rows are defined as climb (uphill 1420), neutral (flat 1415), descend (downhill 1425) and the columns are related to the threshold index selection.

Although one embodiment shows that the settings are made automatically, in another embodiment, the settings are selected or modified by the user, modified by the input provided by the user, or the like. In one embodiment, the settings are a combination of automatic settings, user selected settings, and user input information.

In one embodiment, the user's mobile device 95 (or one or more smart device(s) in communication with the user's mobile device) has one or more sensors for obtaining data such as inertia, pitch, roll, yaw, altitude, and the like. Some or all of the information is provided to the vehicle setup application 1124 to allow the vehicle setup application 1124 to automatically change some tune settings on the fly, provide a notice to the rider to manually change one or more tune settings, or some combination thereof.

Figure 15:
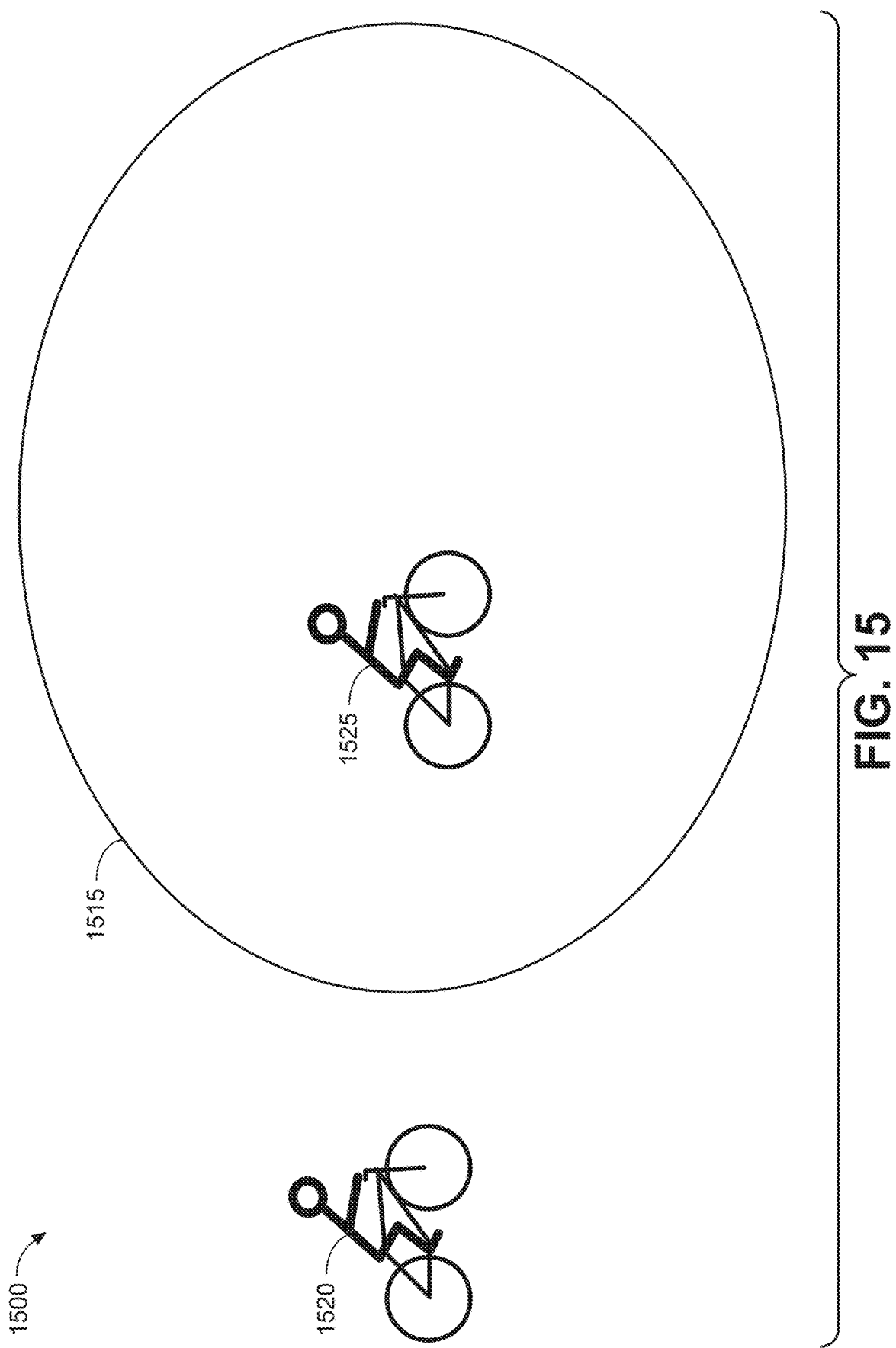
FIG. 15 is a high level view of a defined area, in accordance with an embodiment.

Referring now to FIG. 15, a high level view 1500 of a defined area is shown in accordance with an embodiment. For example, in one embodiment, the user' mobile device 95 includes location information from mobile device 95 that is pulled into the vehicle setup application 1124. The location information is GPS location information, WiFi location information, Cellular network location information, or any information used by the mobile device 95 to obtain location information.

In one embodiment, the vehicle setup application 1124 includes location information that defines an area 1515 (such as a geofence, elevation level, terrain type, or the like). When the mobile device 95 enters into the area 1515 (as shown by bike 1525 inside area 1515 and bike 1520 outside of area 1515), the vehicle setup application 1124 updates some of the tune settings to match the tune settings for the given area. The update to the tune settings is automatically performed or is provided as an "advisory" to the rider to modify the settings to the geofence settings. In one embodiment, the location settings are adjusted by the in-vehicle setup application 1124 settings based on the previously described features that were input into the application as discussed with respect to FIGS. 12-14.

In addition, in one embodiment a new rider receives a first set of automatic setting adjustments when they entered area 1515, while an expert rider (or intermediate rider) receives a second set of automatic setting adjustments when the entered area 1515. In one embodiment, the differentiation of settings occurs between bike types, e.g., a road bike entering into area 1515 likely (but may not necessarily) receives different automatic settings that that of a gravel bike, mountain bike, etc. In one embodiment, the entering into area 1515 provides a multitude of possible automatic settings based on the rider information in the vehicle setup application 1124, information such as rider skill level, bike type, one or more components on the bike, rider motivation, and the like.

Referring again to FIG. 12, in addition to having automatic or predefined tunes 1201-120*n*, there can also be peer generated custom tunes 120*n* that will be provided, such as in a custom mode, to other application users for download and utilization.

For example, trail x is ridden by Johnny Pro and he records his settings (or tune) and uploads them for the vehicle setup application 1124 (Johnny does trail x). Another rider downloads Johnny Pro's settings (e.g., the tune Johnny does trail x) and uses that specific tune to ride trail x (or to ride other trails).

In another example, Franky Speed rides his bike with specific components thereon, record his settings, and upload them for the vehicle setup application 1124. Another user with a bike having the same (or similar) specific components thereon (or same bike model, brand, year, etc.) is able to find the custom tune for her similar bike and download that custom Franky Speed configuration to her mobile device 95. Thus, in one embodiment, there are custom tunes for general locations, different altitudes, specific rides, specific riders, certain bikes, different bike brands, different bike models, bikes with similar components, and the like.

For example, the custom tunes can come from FOX or the OEM and might target a specific type of rider or a specific geographic location. In one embodiment, the custom tunes are downloaded into a "bullpen" and can then be dragged into the active stack of 5 (or any defined number) tunes. In one embodiment, when a new tune is selected from the bullpen, the replaced tune drops down into the bullpen, available for later use (e.g., "Johnny does trail x" replaces comfort 1204). In one embodiment, before dissemination, any custom tunes is sent for approval, and then the approved custom tunes is available for download.

Although, in one embodiment, the custom tunes are managed by the vehicle setup application 1124 or the servers supporting vehicle setup application 1124 (e.g., the management location from which tunes are uploaded to and downloaded from), in one embodiment, one or more custom tunes 120*n* is shared peer-to-peer via WiFi, Bluetooth, NFC, SMS, MMS, etc. In one embodiment, they are shared through a middleman such as a webstore, a social network, a riding club, or any combination thereof.

In one embodiment, there is a collection of performance data taken during the ride. The collected performance data is used to compare the settings (or tune) used on the ride with the actual performance of the active valve and other reporting components. This comparison is used to determine if the selected settings (or tune) was the most appropriate for the ride, if one or more aspects of the tune should be adjusted for performance gains, if the active valve system was operating correctly, if any faults were detected, or the like. For example, in the collected performance data it may be determined that the downhill setting does not allow for the full motion of one or more active components. The determination is further that the downhill setting was too stiff and that a softer setting has allowed for additional performance to be obtained from the one or more active components. In another embodiment, the determination is that one or more of the active valves in the active valve system was not operating correctly and needed an update, replacement, or the like. In yet another embodiment, the determination is that one or more of the components on the bike was not operating correctly and needed repair, replacement, or the like.

In one embodiment, if the determination was that the tune was not correct for the situation, the result of the comparison is an adjustment to the downhill portion of the tune. In one embodiment, if the same downhill adjustment was needed for the same rider on a number of different rides, there may be further input such as rider weight, height, seat settings, and the like that are added to the inputs for the vehicle setup application 1124 and then used to adjust some portion of one or more of the settings (or tunes). Moreover, if the same downhill tune adjustments were determined for a number of riders (each of which being shorter than 5'7") that height information is used to automatically modify the initial tune information once the height was provided by the rider to the application 124. Although height is discussed, in one embodiment, the recurring feature is one or a combination of rider height, weight, gender, age, body mass, body type, fitness level, heart rate, seat height setting, seat pitch, seat offset, crank arm length, wheel diameter, handlebar width, handlebar offset (fore or aft), pedal type, etc. Further, some or all of the above information is obtained by user input, by communication between the user's mobile device 95 and networked devices such as a smart scale, smart watch or other smart jewelry that monitors one or more user's biometrics (e.g., heart rate, body mass, temperature, etc.); and the like.

Figure 16A:
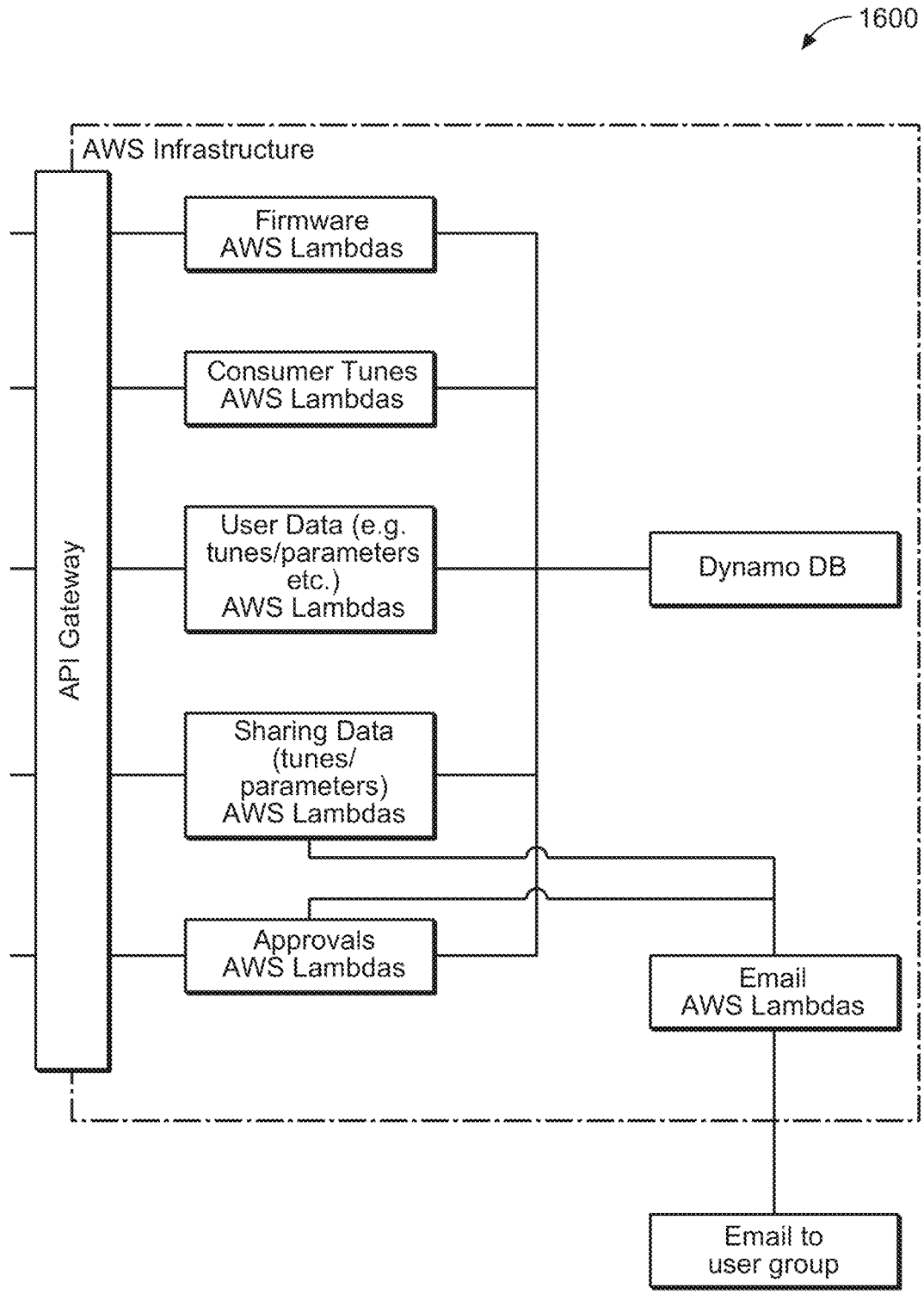
FIG. 16A is a flowchart of an embodiment for sharing custom tunes, in accordance with an embodiment.

Referring now to FIG. 16A, a flowchart 1600 of an embodiment for sharing custom tunes is shown. In flowchart 1600, application 1124 interacts with a web services server that contains assets such as, but not limited to, firmware, consumer (approved) tunes, user data, sharing data, approval data, or the like. In one embodiment, firmware refers to updates to the application 1124 or other components. Consumer (approved) tunes refers to things like bike model specific information, and the like. User data refers to aspects such as, bike profiles, images, information, and the like. Sharing data is in one embodiment, a tune "sandbox". Approval data refers to aspects such as what has been approved, what is pending, etc.

Figure 16B:
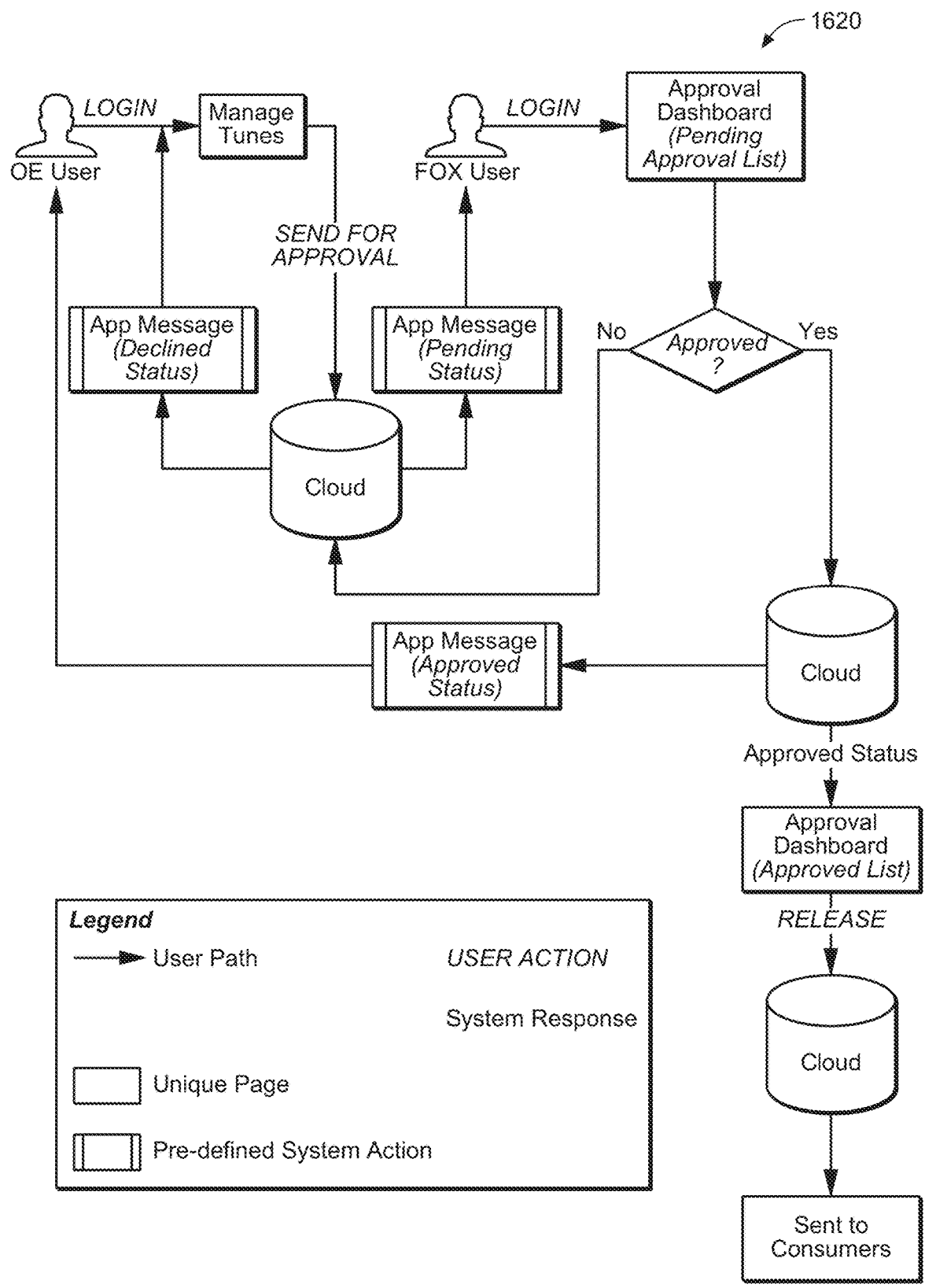
FIG. 16B is a flowchart of an embodiment of a custom tune approval process, in accordance with an embodiment.
Figure 16C:
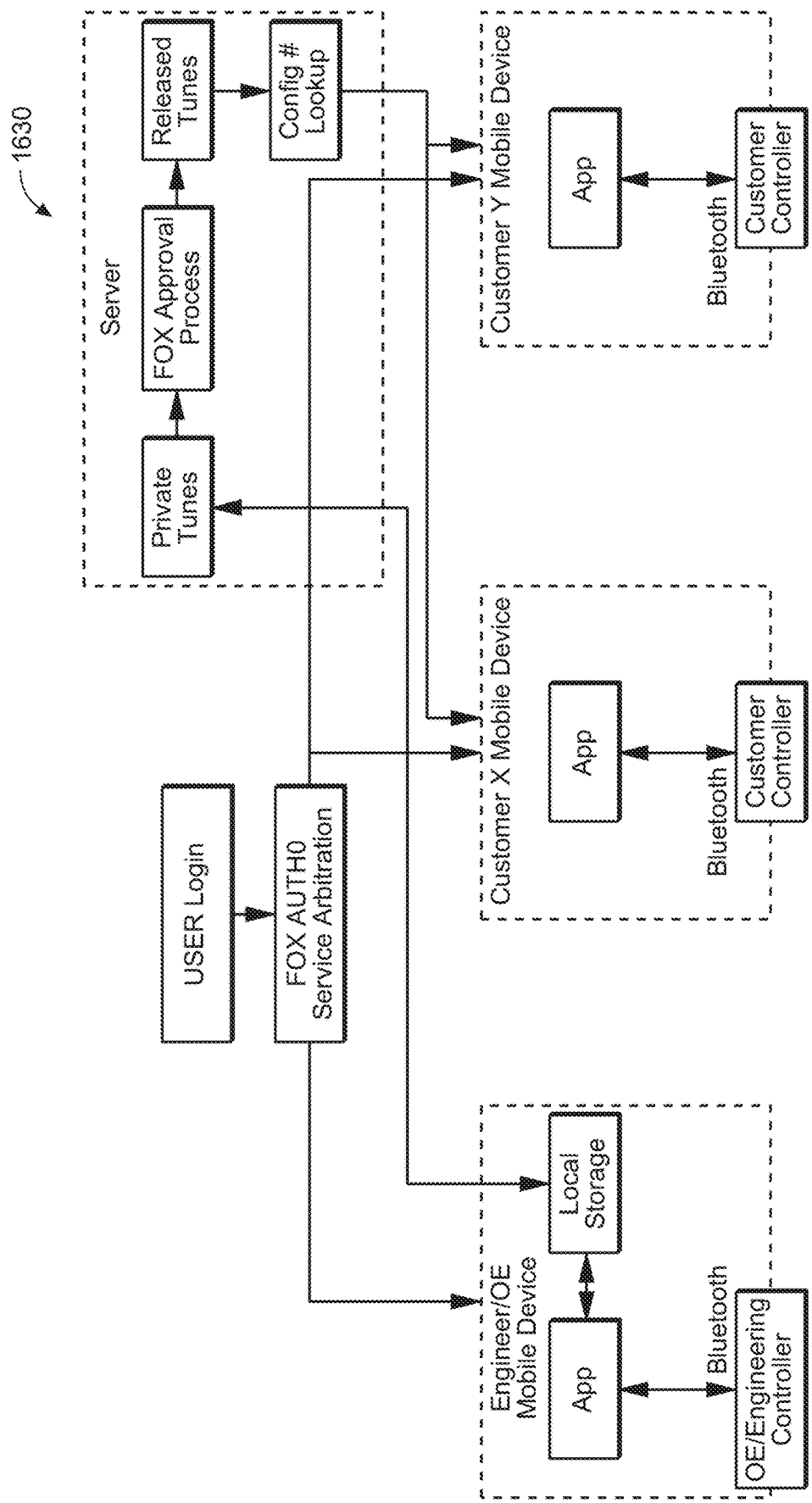
FIG. 16C is a flowchart of an application architecture diagram, in accordance with an embodiment.
Figure 16D:
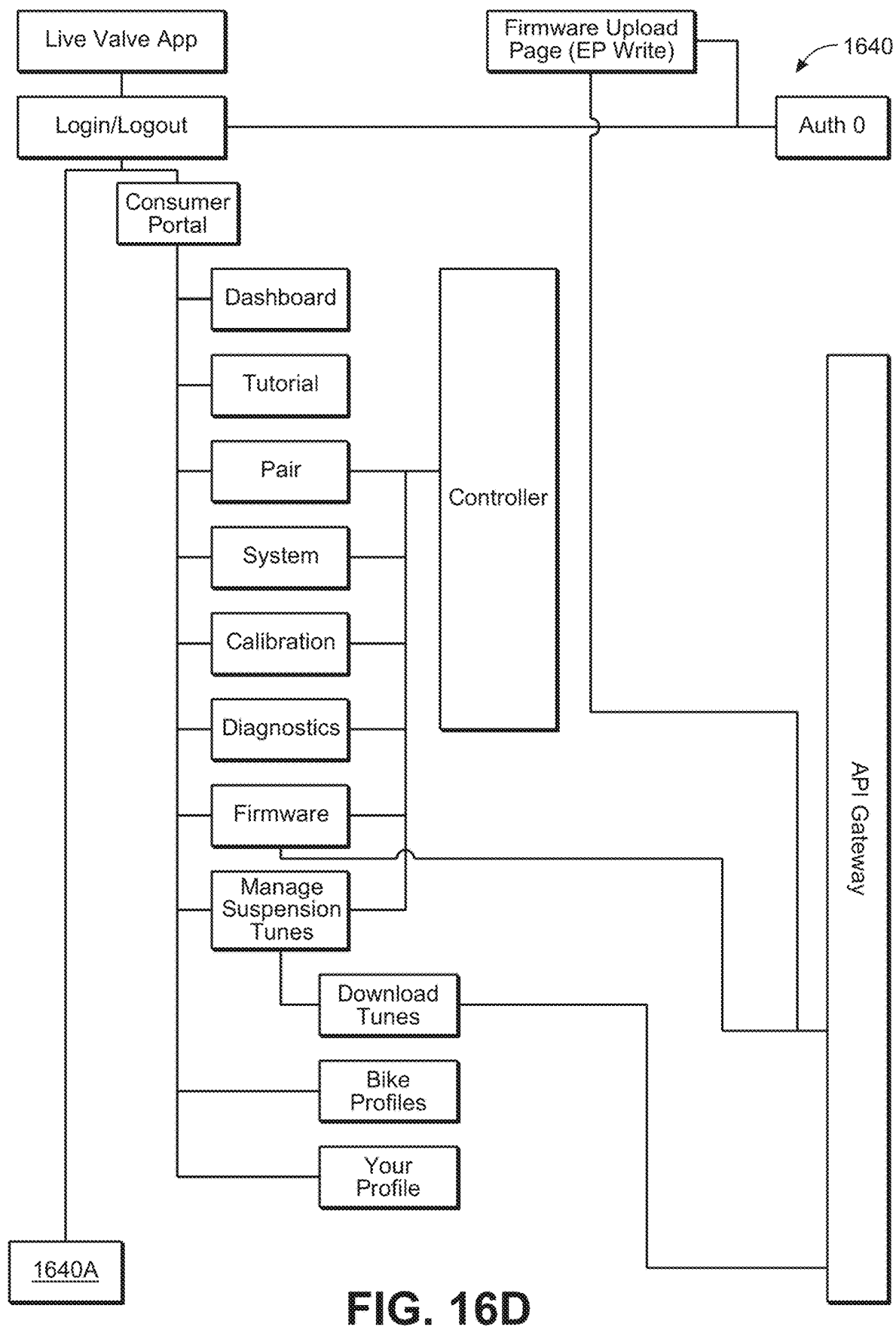
FIG. 16D is a flowchart of a system level application architecture diagram, in accordance with an embodiment.
Figure 16E:
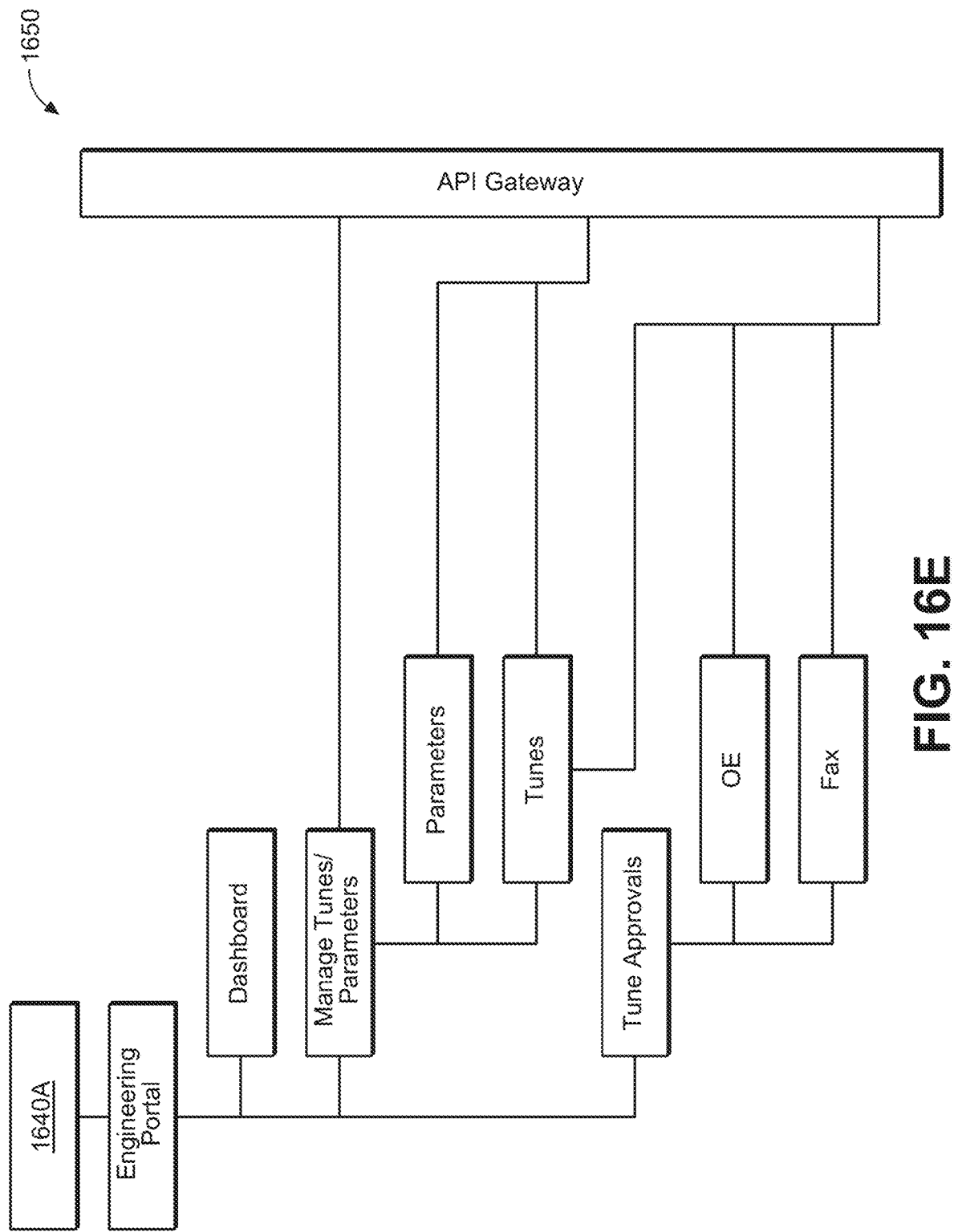
FIG. 16E is a flowchart of a system level engineering portal architecture diagram, in accordance with an embodiment.

With reference now to FIG. 16B, a flowchart 1620 an embodiment of a custom tune approval process is shown. FIG. 16C is a flowchart 1630 of an application 1124 architecture diagram shown in accordance with an embodiment. FIG. 16D is a flowchart 1640 of a system level application 1124 architecture diagram shown in accordance with an embodiment. FIG. 16E is a flowchart 1650 of a system level engineering portal architecture diagram shown in accordance with an embodiment. 1640A of FIG. 16D couples to 1640A of FIG. 16E, and the API gateway leads to the web server shown in further detail in FIG. 16A.

Figure 17A:
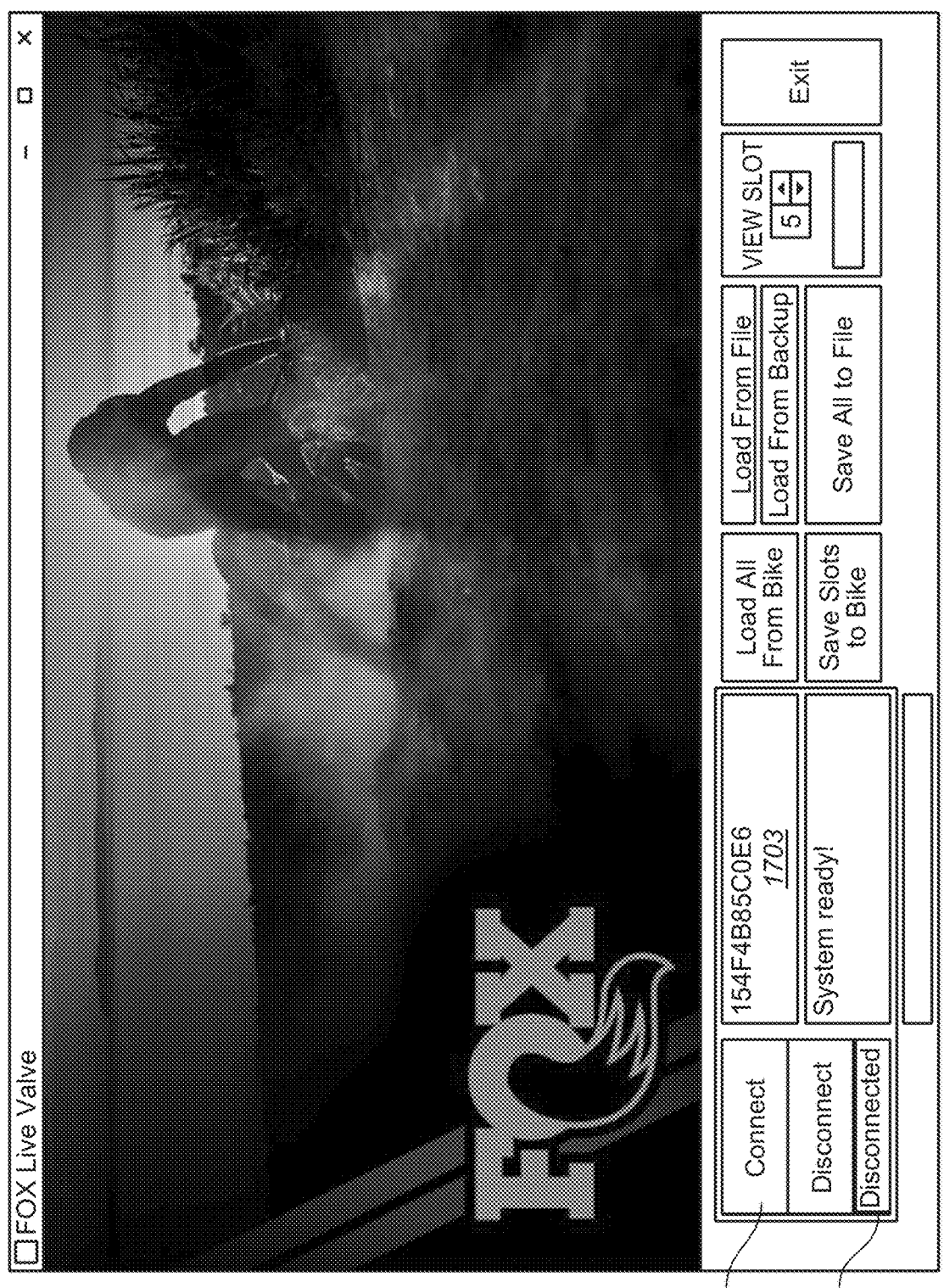
FIG. 17A is a screen shot of the FOX® Live Valve® application, shown in accordance with an embodiment.

Referring now to FIG. 17A, a screen shot of the FOX® Live Valve® application 1700 is shown in accordance with an embodiment. In one embodiment, the application can be used by an original equipment (OE) manufacturer to evaluate new equipment performance on a bike and determine the operational ranges and settings for a desired performance tune.

In one embodiment, the OE can use pre-existing tune settings for a different component as a baseline and then adjust the settings on the new equipment based on the new equipment performance envelope, use case, and the like. For example, an OE front fork assembly version 1 has an established tune (or set of tunes) including settings that have been developed through testing, use, rider input, result evaluation, etc. When the OE is developing front fork assembly version 1.5, they start with tune settings from version 1 and then adjust one or more different aspects of the tune based on the different performance aspects (different performance requirements, different use cases, etc.) of front fork assembly version 1.5.

In addition to the application 1700 providing the numerous options to the OE (or other manufacturer, developer, tuner, etc.), the application also has a user version (e.g., vehicle setup application 1124 described herein) that will provide a reduced number of aspects/thresholds/and features. Thus, instead of having access to all 100 plus features, mods, levels, ranges, settings, etc., of Application 1700, the user version (e.g., vehicle setup application 1124) provides 3, 5, 10, etc. different aspects that are available for modification.

In one embodiment, the vehicle setup application 1124 might include a reduced number of adjustable/modifiable tune features, but the adjustment to one of the tune features actually provides an underlying adjustment to a plethora of different thresholds, features, or ranges, within the actual underlying application.

In one embodiment, the opening of application 1700 initially does not display any settings. To view and edit settings, they must be load from a configuration file, from the bike etc.

In one embodiment, once application 1700 is opened, it will attempt to connect with suspension controller 39. When it is successful connected with suspension controller 39, it will be indicated by a connected symbol shown in connection indicator 1705. In one embodiment, the initial pairing with suspension controller 39 is done by a process such as, but not limited to: If ebike power is on, turn it off. Then turn the power back on. This will put the suspension controller 39 into pairing mode. If the suspension controller 39 has never connected with application 1700, this power cycling may be necessary before connecting. At this point the user has 60 seconds to connect before the pairing window expires. Once the suspension controller 39 has been connected at least once to the application 1700, the 60 second window no longer applies. Anytime the suspension controller 39 is powered, it can be connected.

In one embodiment, once paired, the suspension controller 39 can be selected from the list in box 1703. In one embodiment, once suspension controller 39 is selected, the connect button of connect/disconnect 1702 is selected, and a successful connection will be indicated in connection indicator 1705.

Figure 17B:
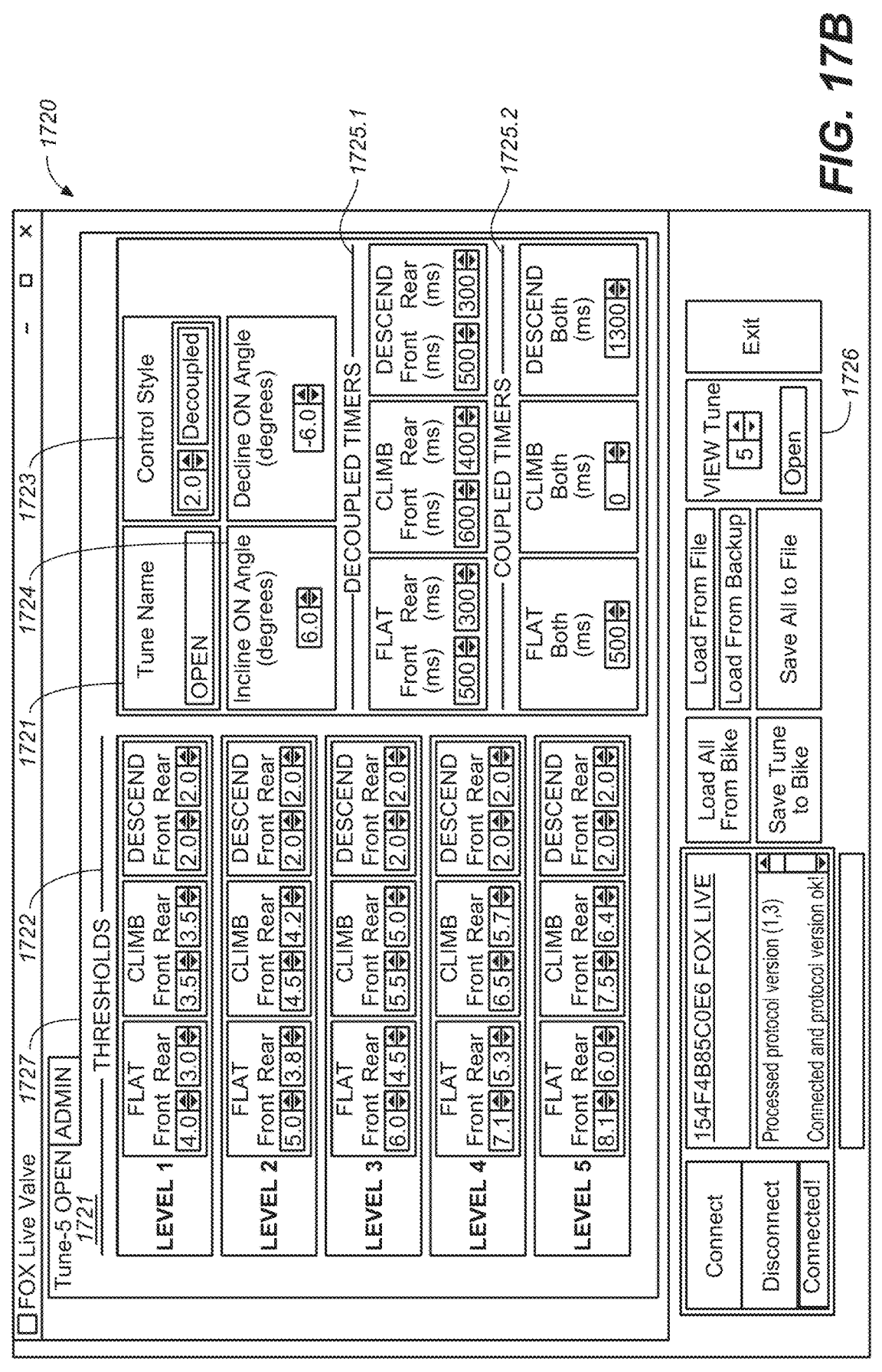

With reference now to FIG. 17B, a screenshot of tune page 1720 is shown in the Application 1700. In one embodiment, the settings are loaded into the application either from a file or from the suspension controller 39. For example, in one embodiment, to load settings into the application from the connected bike, press "Load All from Bike". To load settings into the application from the file, press "Load From File" and select the configuration file.

Once the settings are loaded, they are visible in the tune page 1720. For example, at tune page 1720 the settings are shown as being from tune memory location slot 5.

A "tune" is used herein to encapsulate a group of settings that have been optimized for a particular feel or set of riding conditions. The best way to understand all of the settings in a tune is to look at one level at a time. Within a level, there are three sets of two threshold values for both the front and rear shock. Which of these sets is active depends on what "pitch mode" the bike is in. If the bike is in Incline (climbing) mode, the climb thresholds are used. If the bike is in Decline (descending) mode, the descend thresholds are used. By comparing the sets of thresholds in one level to another, it will be noted that, as the level increases, the thresholds increase. In one embodiment, the level units are g-forces.

In one embodiment, when the user increases the bump sensitivity in the live valve smartphone app (as shown in FIGS. 12-13), under the hood the app moves all of the thresholds in the next level.

In one embodiment, the thresholds include front suspension settings and rear suspension settings. In one embodiment, the thresholds include more or fewer suspension aspects such as a seatpost suspension setting, two different front/rear settings for a vehicle with two rear suspensions, two front suspensions, four wheeled suspension, etc.

There are also different types of use cases (or pitch modes) that can be used. One embodiment, shows three pitch modes, e.g., flat, climb, and descend, however, it should be appreciated that additional use cases or modes such as freefall (or jump mode), etc. are available. In one embodiment, each of the use cases can have their own thresholds and/or share thresholds. In one embodiment, a "0" threshold setting can indicate an always open case, while a "99" threshold setting can indicate an always closed case.

In one embodiment, a configuration file is used to store all configurable settings associated with the operation of a live controller. It is a text file formatted as a YAML (a recursive acronym for "YAML Ain't Markup Language") file. These settings files are used by various programs to (1) program or "flash" settings to the controller's flash memory or (2) read out and save controller settings to a file.

There are many sections in a configuration file, but for the application 1700, the only section that is viewed and edited (unless the user has administrator access to the admin page), is the tune data. Although all settings are uploaded from the bike by the application 1700, it's important to understand that, since all the application 1700 can change are tunes, only the Tune settings are written back to the controller. In one embodiment, since configuration files are text files, they can be easily corrupted by editing.

Referring again to tune page 1720, one embodiment, indicates a tune name 1721 and tune number entry box 1726. The tab at the top of the tune page, shows the tune number as well as the tune name. In one embodiment, when the tune name is edited, the fields will be updated.

Threshold spinboxes 1722 are where bump thresholds can be between 1.3 and 16 g's. Enter 0 for always open and 99 for always closed. When these special thresholds (0 and 99) are entered, the behavior applies only to the fork or shock that the special threshold is associated with. This is different than the always open/always closed controls, which apply to both front and rear.

Control style 1723 can be user selected or left on the default. In one embodiment, control style affects how the suspension performs in various conditions. For example, which timers are active depends on control style 1723, e.g., always open: both front and rear shocks are always open regardless of pitch mode; Always closed: both front and rear shocks are always closed regardless of pitch mode; Decoupled: the front and rear shocks behave independently—a bump detected by the front sensor has no effect on the rear shock; Coupled: the front and rear shocks act together: when the either the front or rear sensor detects a bump, the controller will open both the front and rear shocks; Pitch-determined: in this style, the front and rear are coupled as above when the bike is level ("flat") or descending. When the bike is on an incline ("climb"), the front and rear are decoupled as described above; and the like.

In other words, control style can be a global setting, or a setting for two or more of the plurality of suspension components, the suspension components in a defined grouping, etc. In general, control style can include a number of settings such as always closed, decoupled, coupled, always opened, pitch determined, etc. In one embodiment, the defined grouping is front suspension components, rear suspension components, front and seatpost (or seat) suspension components, rear and seatpost (or seat) suspension components, handlebar and seat suspension components, or any combination thereof.

In one embodiment, "always closed" overrides the tune thresholds and causes the suspension to remain firm (or closed). In one embodiment, "always open" overrides the tune thresholds and causes the suspension to remain soft (or opened). In one embodiment, "Pitch determined" is a standard functionality where all the thresholds remain in operation for each of the suspension components.

In one embodiment, "decoupled" allows two or more of the suspension components to be controlled independently. For example, in a decoupled mode, if the front suspension receives an input (such as a tree root) that causes the front suspension to open, the front suspension change will not be applied to any of the other decoupled suspension components (although the tree root event might as it, or its effects on other suspension components, is encountered by another decoupled suspension component).

In one embodiment, "coupled" causes two or more of the suspension components to change to the same state based on a change to one of the coupled suspension components. For example, if the front suspension is coupled with the rear suspension, an input (such as a tree root) that causes the front suspension to open will also cause the rear suspension to open.

In one embodiment, the decoupled and coupled options include timers for how long the suspension components remain coupled or decoupled. In one embodiment, the timers are also dependent upon the pitch mode (e.g., flat, climb, descend, freefall, etc.)

Angle indicator 1724 provides angle information. In one embodiment, the angles are incline on angle: this is the angle, adjustable from 3° to 9.9°, at which the controller enters "incline" (climb) mode. In other words, incline on angle refers to the angle that indicates when the system should shift to the climb thresholds. This angle is monitored by a sensor that includes an inclinometer or the like. In one embodiment, the incline on angle is pre-defined by the OE, established as part of a tune, be rider adjustable, etc. For example, a training tune has an include on angle of 9 degrees while a race tune has an incline on angle of 6 degrees. Thus, in a training ride example, in one embodiment, when the inclinometer is reading less than 9 degrees the "flat" thresholds is used, when the inclinometer is reading 9 degrees or greater, the "climb" thresholds is used.

Decline on angle: this is the angle, adjustable from −3° to −9.9°, at which the controller enters "decline" (descend) mode. In other words, decline on angle refers to the angle that indicates when the system should shift to the descend thresholds. In one embodiment, this angle is monitored by a sensor that includes an inclinometer or the like. In one embodiment, the decline on angle is pre-defined by the OE, established as part of a tune, be rider adjustable, etc. For example, a training tune has a decline on angle of −8 degrees while a race tune has a decline on angle of −4 degrees. Thus, using the training ride example above, in one embodiment, when the inclinometer is reading more than −8 degrees but less than 9 degrees, the "flat" thresholds is used, when the inclinometer is reading −8 degrees or less, the "descend" thresholds is used and when the inclinometer is reading 9 degrees or greater, the "climb" thresholds is used.

One embodiment shows timers, e.g., decoupled timers 1725.1 and coupled timers 1725.2, for coupled or decoupled modes respectively, which represent the period of time the shock and/or fork will remain open once it has opened. When the timer expires, the shock and/or fork closes. In one embodiment, the system is in a decoupled mode when either of two states exist. Either the control style is decoupled, or the control style is pitch determined and the bike is currently in climb pitch mode. In this mode, the shock and the fork each have their own timer. In one embodiment, the system is in a coupled mode when one of three states exist. Either the control style is coupled, or the control style is pitch determined and the bike is currently in either flat or descend pitch mode. In the coupled mode, the shock and the fork share the same timer.

View tune spinbox 1726, in one embodiment, allows a user to scroll through the five user tunes (tunes 5-9). In one embodiment, unsaved changes to any tune are maintained when scrolling between tunes so changes are not lost. In one embodiment, there a number of tune memory locations available to store the suspension tunes. The tune memory locations include a number of factory memory locations, user memory locations, etc. In one embodiment, the factory tune memory locations are not user modifiable. In another embodiment, the factory tune memory locations are user modifiable but include a reset option that allows the tune memory location to be reset to the factory tune.

In one embodiment, the memory locations are initially filled with a factory tune and then be adjusted by the user. For example, if there is a factory tune A in memory location 2, the user will load factory tune A into user available tune memory location 6. The user then modifies the tune in memory location 6.

As such, during a ride, the user selects the tune found in tune memory location 6. If the tune is not working properly or is not providing the desired results, the rider can then select tune memory location 2 on the app (that is operating on their smart device (e.g., phone, watch, tablet, etc.) which will cause the factory tune A to be used by the controller. In one embodiment, this change to factory tune A will occur in real-time and allow the rider to continue or complete the ride using the factory tune A settings.

Similarly, if the user had filled memory location 6 with Factory tune A 1.1, filled memory location 7 with Factory tune A 1.5, filled memory location 8 with Factory tune A 2.1, etc., if the factory tune A 1.1 was not working properly or not providing the desired results, the rider will switch through each of the different tunes (e.g., A 1.5, A 2.1, etc.). Thus, the rider uses the different tunes to evaluate different changes to a single setting, to a number of settings, etc.

For example, the factory tune has an Incline on angle of 6, while A 1.1 adjusted the Incline on angle to 5, A 1.5 adjusted the Incline on angle to 4, A 2.1 adjusted the Incline on angle to 3, etc. Thus, the user evaluates the ride performance across the same tune with the only variation being the Incline-on angle. From this evaluation, the user (or team, factory, aftermarket component provider, etc.) determines their own personal best performance Incline on angle.

In one embodiment, this tuning approach is used again for any number of the different tune settings. Such capabilities allows a user (team, factory, aftermarket component provider, etc.) to develop a specific tune that was based on the factory tune setting, but which included a number of modified values that worked best for the user and bike configuration.

Admin tab 1727 is, in one embodiment, for internal use and is password-protected.

In one embodiment, after the tune is loaded, whenever a value is changed, its background will turn yellow. This is to help a tuner see all of the changes made before saving. In one embodiment, the box will stay yellow until the tune is saved back to the original source from which the settings came (bike or file). For example, if the user selects "Load All From Bike" and then edits several values, the edited items turn yellow. If the tuner then select "Save All To File", the background of the edited items will stay yellow. This is because the changes have not yet been updated at the source (the bike). In one embodiment, once the tuner select "Save Slots To Bike", and after the download is complete, all backgrounds will return to white. In one embodiment, the backgrounds will also return to white if the tuner overwrites the current changes by re-loading from either the bike or file.

Figure 17C:
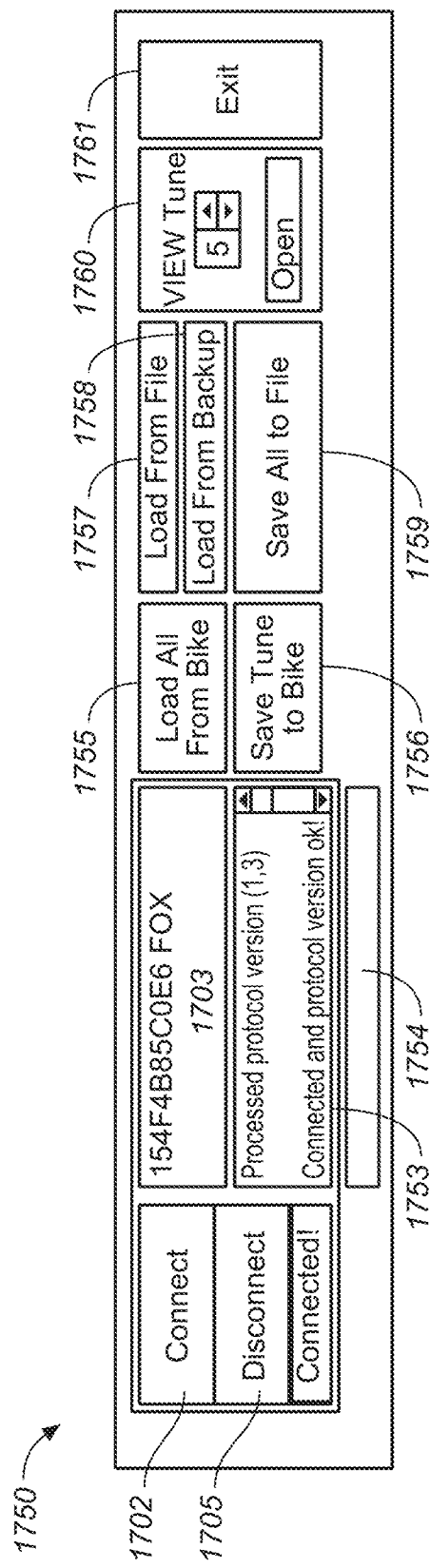
FIG. 17C is a screen shot of the control panel portion of the application page, shown in accordance with an embodiment.

Referring now to FIG. 17C, a screen shot of the control panel 1750 is shown in accordance with an embodiment.

As in FIG. 17A, the connect/disconnect buttons 1702 and connection indicator 1705 are shown in accordance with an embodiment. In one embodiment, when suspension controller 39 has been powered up, it will appear in the controller list (2). In one embodiment, the control panel provides connect/disconnect buttons 1702 to manage connections and the connection status is indicated below the buttons at connection indicator 1705.

As in FIG. 17A, controller list 1703 provides a list of controllers that will appear in this window after a user cycles controller power. In one embodiment, if the controller 39 has never connected with the application, controller 39 power must be cycled before connecting. In one embodiment, there are 60 seconds to connect before the pairing window expires. Once the controller 39 has been connected at least once to the application, the 60 second window no longer applies. In one embodiment, as long as the controller 39 is powered, it can be connected.

Session log 1753 is a scrolled textbox shows a history of all messages, events, and errors that occur during the time the application is connected with the controller. In one embodiment, successful actions are shown in green and errors are shown in red.

Progress bar 1754 shows the uploading and downloading progress of the settings to/from the bike.

In one embodiment, if suspension controller 39 is connected, a load all from bike 1755 button is enabled. When pressed, it reads all settings from the bike but loads only tune settings into the UI.

In one embodiment, if suspension controller 39 is connected, save tunes to bike 1756 button is enabled. When pressed, it reads settings for all tunes from the UI and saves only tune settings to the bike.

In one embodiment, load from file button 1757 causes all settings from a configuration (.yaml) file to be read and populates UI with only tune settings. In one embodiment, the default directory is the "c:\fox live application data files" folder, which is created when the application is installed.

In one embodiment, as mentioned above, before the bike's settings are uploaded or downloaded, a backup file (with serial number, date and time in the filename) is automatically saved to the "c:\fox live application data files\backups" folder. The load from backup 1758 button operates similarly to the load from file 1757 button except for the default file location.

In one embodiment, save all to file 1759 button saves all settings (not just tune settings) to a configuration file. Default folder is "c:\fox live application data files".

In one embodiment, view tune spinbox 1760 allows user to change which tune is being viewed/edited. Unsaved changes from previous tune are preserved so that, when the user scrolls back to the original tune, highlighted edits (yellow background) are still visible.

In one embodiment, exit button 1761 exits the application without saving any unsaved edits. In one embodiment, the user is warned about this before closing.

Thus, in one embodiment, the disclosed active valve tuner application allows an active suspension component manufacturer (such as FOX racing) to provide active suspension settings to a vehicle manufacturer (e.g., a bicycle OE) such that when the active suspension components are installed during the bicycle build by the OE, the suspension controller (or individual active suspension components) will be tuned to acceptable, optimal, preferential (or the like) settings developed by the active suspension component manufacturer. As such, the performance aspects of the active suspension component will be controlled and/or programed by input and guidance received from the active suspension component manufacturer.

Moreover, if the OE modifies the tune based on its own testing, rider feedback, and the like, the OE can provide the modified tune to the active valve application tune evaluation process. Once received, the active valve application tune evaluation process can analyze, test, and vet the modified tune with respect to the capabilities of the active suspension component. If the modified tune is within the required parameters of operation, safety, etc., The modified tune from the OE manufacturer can be added to the tune library. If the evaluation process makes any changes to the modified tune, the updated modified tune can then be provided to the OE, added to the tune library, and the like.

Similarly, if a user adds (or replaces) an active suspension component to their vehicle, instead of attempting to manually tune the active suspension component the user can access the live valve application and receive tunes from the active suspension component manufacturer, from other rides with authorized tunes, and the like. Thus, the active suspension component will be tuned with a working tune. Moreover, the user can then begin to experiment with adjustments to one or more aspects of the working tune framework to develop a personalized tune without having to start from scratch.

Power Spectral Density

In one embodiment, different rides may have certain power spectral density signatures, power spectral density type maps, trail fingerprints, etc. In other words, actual ride characteristics such as surface terrain (e.g., road, trail, dirt, gravel, sand, mud, rock crawling, etc.), speed, and grade information (e.g., uphill speed, downhill speeds, flat speeds, etc.) can be correlated with the associated performance of the vehicle (or one or more suspension components thereof) for the ride (e.g., compression/rebound rates, suspension travel speeds, suspension travel ranges, etc. This information will be used to determine power spectral density signatures, maps, etc.

In one embodiment, there is a collection of the spectral density diagrams and/or the presentation of the spectral density diagrams to utilize for suspension setting determinations.

For example, in a very basic example, a paved road has a first power spectral density signature, a gravel road has a second power spectral density signature, and a dirt road has a third power spectral density signature. Of course, embodiments herein are able to provide different power spectral density signatures for different ride types with those categories, and among combinations of different categories. For example, rides can be broken down into categories, such as, but not limited to concrete, asphalt, gravel size, rock crawling, road age (e.g., old, new, etc.), temperature aspects (e.g., hot, cold, etc.), weather aspects (e.g., dry, wet, icy, etc.), and the like.

In one embodiment, as additional rides on different terrain types are identified, mapped, and ridden, that power spectral density information is added to the ride database (e.g., database 930, performance database 940, a database stored in a rider's mobile device 95 memory 1110, stored in the memory of the controller 39, etc.) along with suspension settings, suggestions, and the like. In so doing, the power spectral density information can be correlated with different ride and terrain characteristics and the associated suspension settings can be obtained. These suspension settings can then be automatically applied to the suspension, provided as suggested manual user input to change suspension settings, or a combination thereof.

In one embodiment, the power spectral density information is provided at a number of different databases. For example, when the rider is home planning the ride, they may be using a home computer/laptop/tablet, or the like to interact with a large storage environment (either locally e.g., ROM 710 or over a network connection e.g., database 930, performance database 940, etc.) of power spectral density information to generate a filtered amount of power spectral density information and its associated suspension settings configuration data. This filtered amount of power spectral density information and associated suspension settings can then be added to the memory of the rider's mobile device 95 and/or the memory slots of suspension controller 39.

On the way to the ride, the rider may utilize their mobile device 95 to interact with local storage (e.g., memory 1110) or over a network connection to interact with their home computer database (e.g., ROM 710) or the network database (s) (e.g., database 930, performance database 940, etc.) to further filter/update the power spectral density information suspension settings to include location information, weather information, etc. In one embodiment, this information is added to (or replaces) the power spectral density information and associated suspension settings in the memory of the rider's mobile device 95 and/or the memory slots of suspension controller 39.

In one embodiment, if the rider is out of long range network coverage, they may only be able to access the local storage on their controller 39, local storage on their mobile device 95 along with the Application 1124 thereon, storage on a laptop or tablet, USB, hard drive, SSD, etc. to make any final inputs (e.g., components, weather, location data, terrain type, ride course changes, etc.) and receive the finalized version of the suggested initial suspension settings.

In one embodiment, for a vehicle with passive suspension there will only be one suggested suspension setting e.g., the configuration for the vehicle to be set before the ride/drive commences.

In contrast, a vehicle with an active or semi-active suspension might receive an initial suggested suspension setting (that is manually or automatically set-up prior to the start of the ride/drive), a number of suggested suspension settings to be implemented (automatically, upon rider/driver/passenger approval, manually, or a combination thereof) as the ride/drive is being performed, where the suggested suspension settings to be implemented are based on actual performance data suggested modifications and/or for the different terrain segments that are encountered.

In one embodiment, the different power spectral density information and associated suspension settings can be obtained based on rides that have already been ridden. For example, after a ride, the power spectral density information for the ride, including the terrain characteristics, speed, and the associated suspension settings can be downloaded to the ride database. This information is available to establish suspension settings for another rider that is going to go on some or all of the same ride. In one embodiment, each time a given ride (or portion of the ride) is made, the power spectral density information and associated suspension settings can be used to refine the suspension settings model.

In one embodiment, the amount of input from a repeated ride may be weighed by a metric such as skill/ride level, experience, suspension components, bike characteristics, rider characteristics, etc. For example, in one embodiment, a professional rider's data is weighted more than a non-professional rider's data for purposes of refining the suspension model.

In one embodiment, the amount of input from a repeated ride may be weighed by a metric such as a rider's characteristic, e.g., weight, height, inseam, or the like. For example, data from a rider with a weight (height, etc.) that is outside of one standard deviation above or below normal might be weighted less than data from a rider within one standard deviation of normal.

In one embodiment, the different power spectral density information and associated suspension settings can be extrapolated for rides (or portions of rides) that have not been ridden, or do not have information stored in the ride database. For example, the new ride is a fire road of dirt and gravel with different grades. Power spectral density information for previously ridden fire roads of dirt and gravel with similar grades can be used to extrapolate initial suspension settings for the new ride. In another example, a new ride includes a sand terrain portion, as such, power spectral density information for previously ridden sand terrain is used to extrapolate initial suspension settings for the new ride. In yet another example, when the new ride includes a sand terrain portion, power spectral density information for previously ridden sand terrain with similar features (e.g., grades, corners, expected speeds, and the like) and/or weather conditions, etc. is used to extrapolate initial suspension settings for the new ride.

In one embodiment, once the rider begins riding on the new ride with the extrapolated suggested initial suspension settings, the suspension settings can be evaluated in real-time to determine any adjustments that may be made to the initial suspension settings (e.g., automatic adjustments and/or providing a suspension adjustment setting suggestion to a user for a manual suspension change).

In one embodiment, as the ride is made (or after the ride is completed), the power spectral density information is then added to the database, such that the new actual power spectral density information is available for the actual ride performed. In addition, as described herein, in one embodiment, the new power spectral density information is used to update the power spectral density database for a given terrain/environment. Thus, the actual ride data is available for suspension setting suggestions/automation and the power spectral density information for extrapolation will also be refined.

Thus, embodiments described herein provide at least long time averaging and short time obstacle adjustment suspension settings capability.

For example, a ride can be broken down into segments, and in an active adjustable suspension, the suspension settings can be adjusted per segment or suggested suspension settings can be provided to the suspension management user (e.g., rider, driver, navigator, etc.) such that the suspension settings are available for each segment. For example, as a truck (or motorcycle, bicycle, e-bike, car, side-by-side, snowmachine, etc.) is driven along a ride, the suspension settings are initially set for the paved road segment, then adjusted to the dirt road segment, adjusted for a whoops segment, back to the dirt road segment, a muddy segment, back to the dirt road segment, a sandy segment, a dunes segment, a fast dirt road segment, a slow rock crawling segment, back to the dirt road segment, etc.

In one embodiment, once the driver begins the ride, the suspension settings can be evaluated in real-time to determine any adjustments that should be made to one or more of the different suspension settings (e.g., automatic adjustments and/or providing a suspension adjustment setting suggestion to a user). In one embodiment, any real-time suspension setting adjustments will be used for each segment of the same terrain type along the ride. For example, if the dirt road segment suspension setting is modified, when the suspension is later set to the next dirt road segment, the modified dirt road segment suspension settings will be used.

In one embodiment, this type of active adjustment can be based on modifications to suspension settings based upon changing conditions such as weather, temperature, and the like. For example, if the third dirt road segment is warmer (or wetter, etc.) the previously modified dirt road segment suspension settings may be further modified based on the changing temperature, weather, and the like. That is, instead of modifying the initial third dirt road segment suspension settings based upon the changed/changing conditions, the previously modified dirt road segment suspension settings will become the new dirt road baseline suspension settings and any modifications based upon the changed/changing conditions will be made to the new dirt road baseline suspension settings.

In a suspension that is not actively adjustable, the segments (and their associated suspension settings) can be evaluated to determine one or more of, the segment or segments that will be most often encountered during the ride, which segment or segments will have the most impact on the suspension, which segment or segments are the most valuable for having the best suspension performance, overall ride-time, etc. This information can then be used to generate a single suspension setup that is used on a non-active suspension to obtain the best overall performance for a given ride.

For example, in the ride discussed above, e.g., a ride having a paved road segment, a dirt road segment, a whoops segment, another dirt road segment, a muddy segment, another dirt road segment, a sandy segment, a dunes segment, a fast dirt road segment, a slow rock crawling segment, and another dirt road segment, in one embodiment, the suspension settings may be based on the dirt road settings since the ride is mostly on dirt.

In one embodiment, the suspension settings may be based the sandy segment since that segment will be the slowest or hardest to traverse without the appropriate sand suspension settings. In one embodiment, the suspension settings may be based upon a combination or amalgamation of the dirt and sand settings to provide a suspension that is passable for the sand segment but provides better performance than the sand settings on the longer dirt road segments, or the like to arrive at the fastest overall time for the given ride, or the like.

In one embodiment, once the suspension setting determination is made (automatically, based on user preference, based on a combination of data evaluation and user input, and the like), the suspension settings will be generated for the bicycle (or motorcycle, e-bike, car, side-by-side, truck, snowmobile, etc.) and provided for the rider (or crew/mechanic/etc.) to set-up the suspension accordingly. In one embodiment, once set, those suspension settings will be used for the entirety of the ride.

In one embodiment, during the ride, power spectral density information will be recorded. Once the ride is completed, the power spectral density information can be evaluated to determine if any adjustments should be made to one or more of the different suspension settings (e.g., there were x-bottom outs, the suspension was too hard for too much of the ride or an important segment of the ride such that significant time/performance was lost, the suspension was too soft for too much of the ride or an important segment of the ride such that significant time/performance was lost, the suspension was perfectly set for one or more of the segments, etc.).

In one embodiment, regardless of whether there was a single suspension setting or active suspension setting adjustments, the power spectral density information will be stored, added to the database, or the like and used to confirm suspension settings for a given power spectral density signature, establish new (modified) suspension setting for a given power spectral density signature, added to an existing amount of similar suspension settings for a given power spectral density signature (either weighted or not), and the like. As such, the next time a ride is made across the already ridden terrain, there will be existing power spectral density information with associated suspension settings. Such information will include the resultant base-line active suspension setting information as well as set-and-forget suspension settings that are generated based on actual performance data across the previously driven ride. In one embodiment, the enhanced power spectral density information with associated suspension settings will also be available for extrapolating suspension set-up for yet another new ride.

In one embodiment, the spectral density information is generated as a 3-D surface of spectral density curves to reduce the size of the data being transmitted. In one embodiment, the comparison is done locally (e.g., on vehicle) at the sensor and the answer (e.g., the suspension setting adjustment) is sent to the controller/active valve. In one embodiment, the sensor information is provided to a mobile device 95, the controller 39, a networked computing system and the like and the comparison is done locally (e.g., on vehicle) at the computing device and the answer (e.g., the suspension setting adjustment) is sent to the controller and/or active valve. In one embodiment, the sensor information is provided to a mobile device 95, the controller 39, a networked computing system and the like and the comparison is done remotely (e.g., off vehicle) and the answer (e.g., the suspension setting adjustment) is sent to the mobile device 95 (or the like) and provided to controller 39 and/or active valve 450.

In one embodiment, output from an embodiment of a rough road detection system and method used to determine when a suspension change is warranted based on a terrain type being traversed by the vehicle and/or one or more sensor inputs provided to or used by a rough road detection embodiment, is well-suited to being received by, and/or utilized as input to, a customizable tune application such as the active valve customizable tune application.

In one embodiment, the output from the customizable tune application such as the active valve customizable tune application, and/or one or more sensor inputs, provided to and/or utilized by the customizable tune application is well-suited to being information used by a rough road detection system and method. In one embodiment, the input information is used to supplement the inputs to the rough road detection system and method. In one embodiment, the performance of the rough road detection is performed on an application such as the mobile device application, or other computing devices such as the desktop, laptop, virtual computing environments, and the like.

Active Body Wearable Device

In the following discussion, information from a sensor and/or controller is provided to an active valve shock assembly of a body wearable device. In so doing, the body wearable device will be able to adjust the damping characteristics of the active valve shock assembly to provide a user with better feel, a larger range of available performance, and return some of the "feel" that is lost when a passive shock assembly (or no shock assembly) is used in the body wearable device.

In one embodiment, the body wearable device is integrated with one or more components of a vehicle (e.g., a sensor, controller, active valve, or the like) such that the damping characteristics of the body wearable device are tuned with respect to the performance of the vehicle. In one embodiment, sensors, which may be mounted on the vehicle (such as sensors 35), carried in the user's pocket (e.g., mobile device 95, smart jewelry, smart watch, etc.), mounted on the body wearable device (e.g., liDar, etc.), will provide information not only to the active valve shock assembly coupled with the vehicle (if present) but also to the active valve shock assembly integrated with the body wearable device.

For example, in one embodiment, the active valve shock assembly in the body wearable device is normally soft. However, when the sensor(s) detect the vehicle going downhill, the active valve shock assembly can switch to a firmer mode to provide better support for the user by slowing down the rate of articulation of the joint to which the active valve shock assembly is attached.

Prosthetic

With reference now to FIG. 18A, a prosthetic arm 1801 with an active valve shock assembly 1838 is shown in accordance with an embodiment. In one embodiment, the active valve shock assembly 1838 is used for the elbow joint 1817. However, this is provided for purposes of clarity. It should be appreciated that in one embodiment, the prosthetic arm 1801 may have a plurality of shock assemblies (including one or more active valve shock assemblies) of similar or different sized depending upon the joints that are provided in the prosthetic. For example, in prosthetic arm 1801 there may be an active valve shock assembly 1838 for the elbow joint 1817 and an active valve shock assembly 1838w for the wrist joint 1818. In one embodiment, the wrist joint 1818 active valve shock assembly 1838w is smaller (or has a smaller damping range) than the active valve shock assembly 1838 for the elbow joint 1817 to provide better feel, performance, nuanced maneuvering, etc. while the elbow joint 1817 active valve shock assembly 1838 has a larger size (or larger damping range) to provide a larger operating range for absorbing larger impacts.

Referring now to FIG. 18B, a prosthetic leg 1851 with an active valve shock assembly 1888 is shown in accordance with an embodiment. In one embodiment, the active valve shock assembly 1888 is used like a calf muscle between the knee joint 1867 and the lower leg.

However, this is provided for purposes of clarity. It should be appreciated that in one embodiment, the prosthetic leg 1851 may have a plurality of shock assemblies (including one or more active valve shock assemblies) of similar or different sized depending upon the joints that are provided in the prosthetic. For example, in prosthetic leg 1851 there may be an active valve shock assembly for the calf muscle and an active valve shock assembly 1888a for the ankle joint 1868. In one embodiment, the ankle joint 1868 active valve shock assembly 1888a is smaller (or have a smaller damping range) than the active valve shock assembly 1888 to provide better feel, performance, nuanced maneuvering, etc. while the active valve shock assembly 1888 has a larger size (or larger damping range) to provide a larger operating range for absorbing larger impacts.

In one embodiment, the active valve shock assembly used in the prosthetic (e.g., either or both of prosthetic leg 1851 and prosthetic arm 1801) is similar in operation to the active valve shock assembly 38 disclosed herein. That is, the prosthetic active valve shock assembly will be able to receive input from a controller 39 and adjust one or more damping characteristics of the prosthetic active valve shock assembly during operation.

Orthotic

Figure 19B:
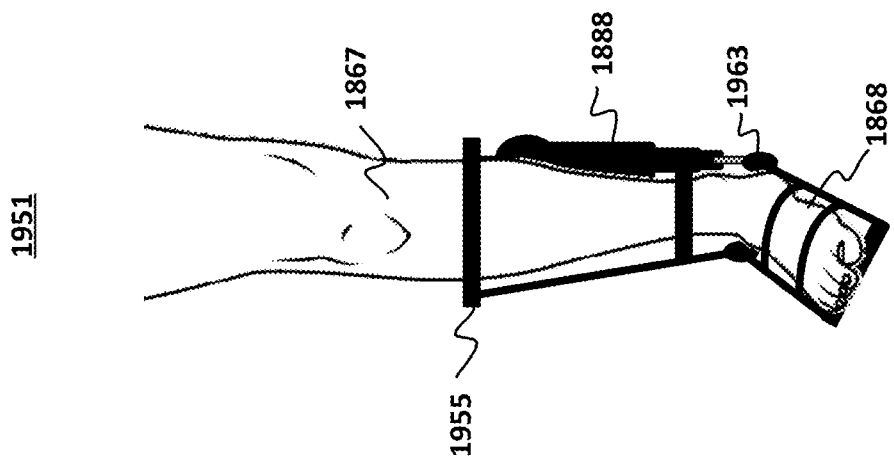
FIG. 19B is a perspective view of a exoskeleton boot with an active valve shock assembly, in accordance with an embodiment.
Figure 19A:
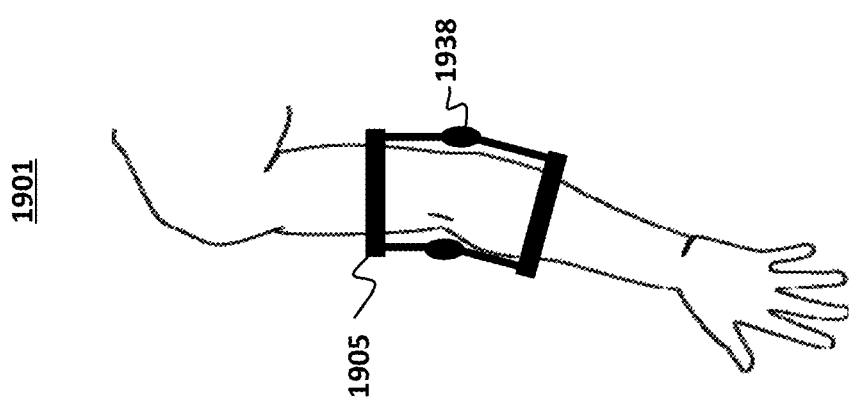
FIG. 19A is a perspective view of a orthotic arm brace with an active valve shock assembly, in accordance with an embodiment.

With reference now to FIG. 19A, an arm 1901 with an orthotic 1905 is shown in accordance with an embodiment. Although the orthotic 1905 is shown as an elbow brace in FIG. 19A, in another embodiment, the orthotic is a brace and/or splint used on one or more areas of the body, such as, but not limited to, a joint, tendon, ligament, muscle, bone, etc.

Figure 20:
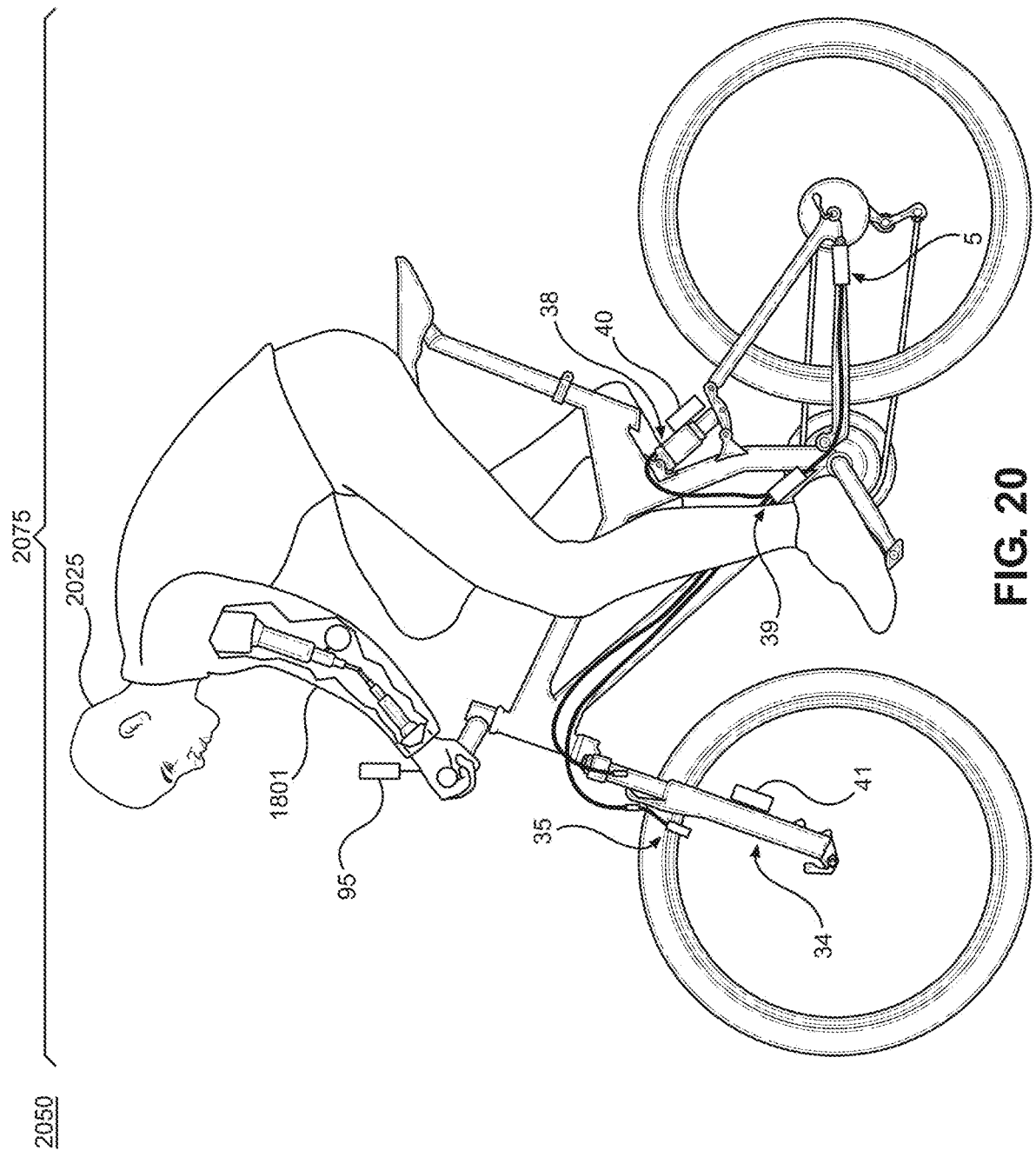
FIG. 20 is a perspective view of an active valve system on a vehicle with body wearable device integration, in accordance with an embodiment.
Figure 21:
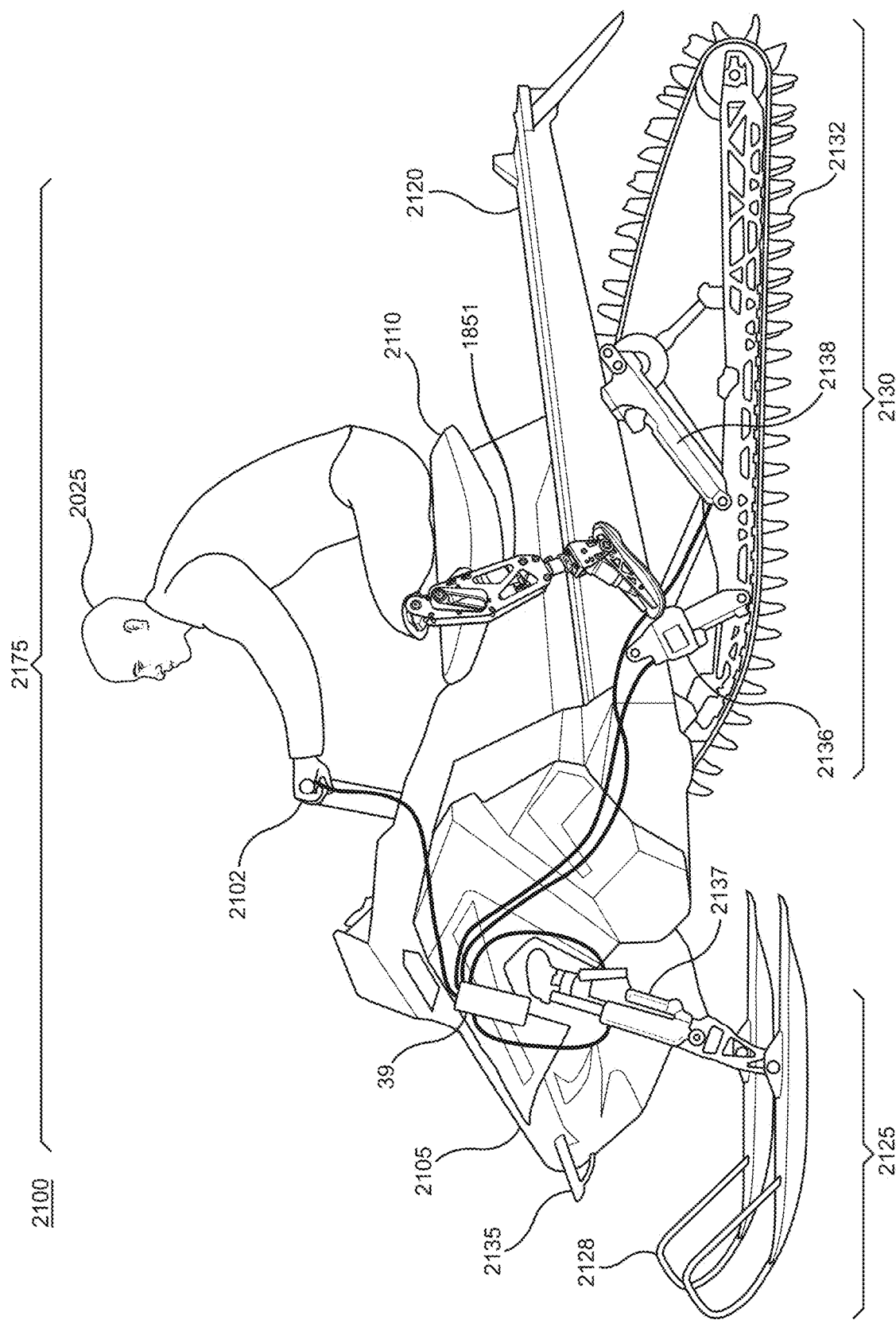
FIG. 21 is a perspective view of an active valve system on a different vehicle with body wearable device integration, in accordance with an embodiment.
Figure 22:
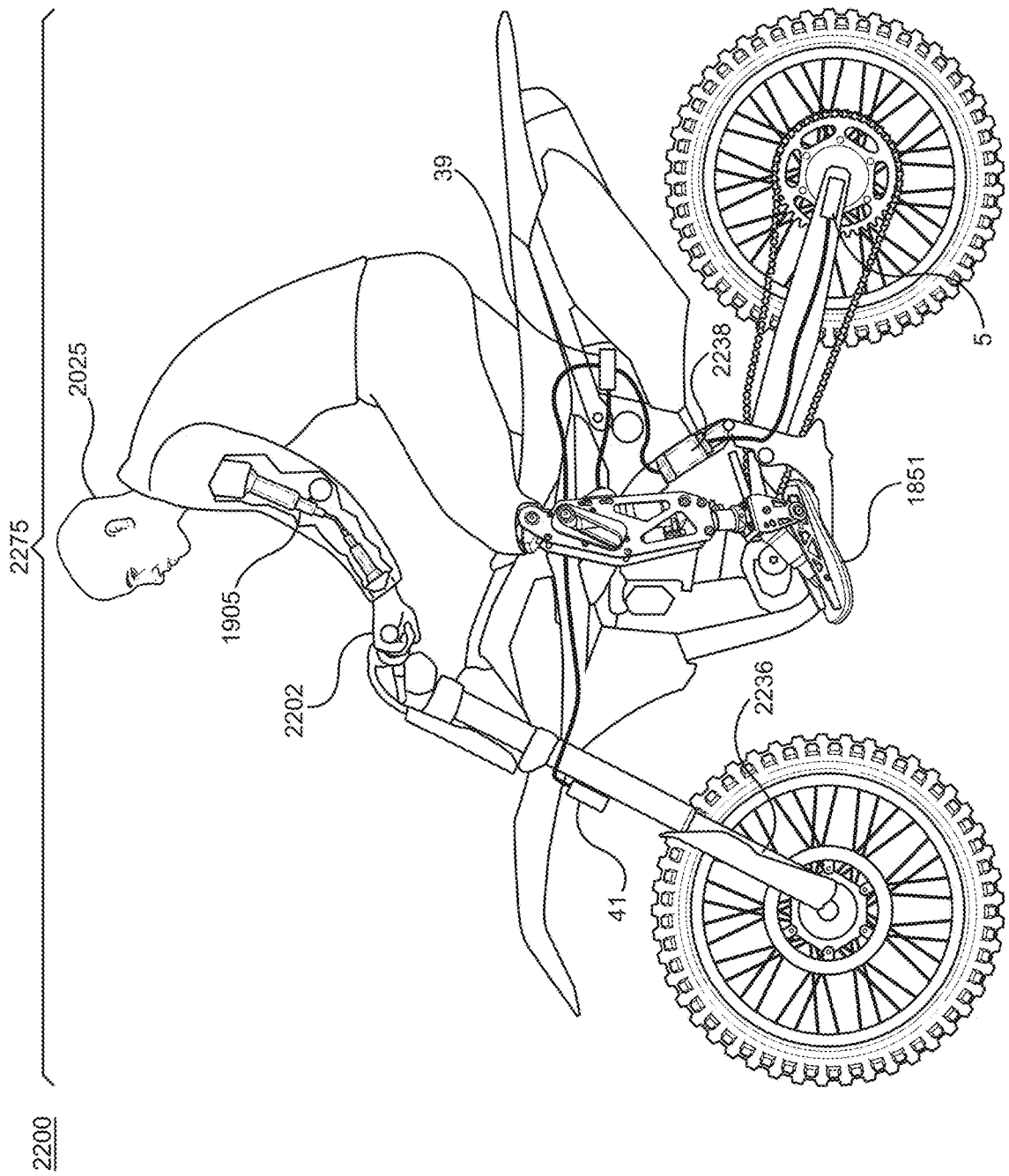
FIG. 22 is a perspective view of an active valve system on yet another vehicle with body wearable device integration, in accordance with an embodiment.

In one embodiment, orthotic 1905 includes a hinge joint 1938. In one embodiment, an active valve shock assembly is used for the hinge joint 1938. In one embodiment, instead of an active valve shock assembly hinge joint 1938 will use an active rotary damper, linear damper, or the like, to control the rotational rate and/or the resistance of the hinge joint 1938. In one embodiment, the active/controllable rotary damper has wireless communications capabilities such that it can be integrated with the active suspension system of a vehicle (as shown in FIGS. 20-22).

Referring now to FIG. 19B, a leg 1851 with an exoskeleton 1955 is shown in accordance with an embodiment. Although the exoskeleton 1955 is shown as an boot style in FIG. 19B, in another embodiment, the exoskeleton is used on a different limb, a plurality of limbs, as a partial body exoskeleton, a full exoskeleton, and the like.

In one embodiment, exoskeleton 1955 includes a hinge joint 1963 and an active valve shock assembly 1888. In one embodiment, the active valve shock assembly 1888 is used to supplement and/or increase the performance of one or more muscle of the lower leg below the knee joint 1867. However, this is provided for purposes of clarity. It should be appreciated that in one embodiment, the exoskeleton 1955 may have a plurality of shock assemblies (including one or more active valve shock assemblies) of similar or different sized depending upon the size and/or coverage provided by the exoskeleton 1955.

In one embodiment, the active valve shock assembly used in the body wearable device (e.g., prosthetic 1801/1851, orthotic 1905, and/or exoskeleton 1955) is similar in operation to the active valve shock assembly 38 disclosed herein. That is, the active valve shock assembly will be able to receive input from a controller 39 and adjust one or more damping characteristics of the active valve shock assembly during operation.

Body Wearable Device Operation

With reference now to FIG. 20, a schematic side view of the bicycle 2050 with focus on the active suspension system and the integration of the body wearable device and its components 2075 is shown in accordance with an embodiment. In one embodiment, the body wearable device, e.g., prosthetic arm 1801, is added to the schematic of the bicycle 50 of FIG. 2 to show how the active valve shock assembly 1838 (e.g., wrist and/or elbow) in the prosthetic arm 1801 can be wirelessly added to the active suspension system and the integration of the prosthetic and its components 2075. In one embodiment, the same protocols for entering and operating on the network (e.g., encryption, passwords, settings, setup, specifications, and the like) are used by the active valve shock assembly 1838 (or 1838w) of the prosthetic arm 1801 as were used by any of the other active valve shock assemblies (e.g., as shown in FIGS. 1-3 and described herein).

For example, in one embodiment, the controller 39 of the bicycle 2050 is used to provide the damping characteristic adjustments to the active valve shock assembly 1838 of the body wearable device, e.g., prosthetic arm 1801.

In one embodiment, bio-feedback (such as from a user's brainwaves, muscle flexing, tendon movements, associated with at least one bodily function of the user, and the like) will be obtained by a sensor monitoring the user of the body wearable device. In one embodiment, the bio-feedback data will be provided to the controller 39 and used (alone and/or in combination with other sensor data) to generate and provide the damping characteristic adjustments to the active valve shock assembly 1838 of the body wearable device. For example, the sensor (or other component) can monitor muscle contraction at the cuff of the body wearable device and changing the active valve shock assembly damping as needed. In another example, a load cell or similar transducer is used to measure the force between the arm and the body wearable device and the active valve shock assembly damping is changed accordingly. In one embodiment, the sensor will measure brain activity (e.g., brain waves, electromagnetic pulses, or the like) and provide that bio-feedback data to the controller 39.

For example, as a user is riding a mountain bike, they may encounter a steep downhill section with a number of obstacles, bumps, jumps, ruts, etc. As the user traverses the terrain, the controller 39 will receive information from the sensors 35 and provide damping adjustment information to the active valves of the active valve shock assembly(s) (e.g., 38, 1838, and/or 1838w). For example, if the user has a prosthetic arm 1801, the sensor 35 provides information indicative of a jump to the controller 39. As such, the active valve shock assembly 1838 in the elbow and/or wrist 1838w receives an input from controller 39 which automatically adjusts one or more damping characteristics to provide a reduction in damping such that the event input to the handlebars 36 is more easily "felt" by the user.

In one embodiment, as the bicycle 2050 is about to land (or is landing), the sensor 35 provides the landing information to the controller 39 which, in turn, provides another input to automatically adjust one or more damping characteristics (such as firming up) of the active valve shock assembly 1838 in the elbow and/or wrist 1838w to provide better shock performance for the landing. For example, in one embodiment, the firmer setting allows the prosthetic arm 1801 to remain in contact with the handlebars 36 and provide a firmness (similar to the tensing of the muscles in the arm) that reduces deflection of the handlebars 36 in a direction towards the prosthetic and, as a result, allows the user to maintain control of the bicycle 2050.

In one embodiment, after the bicycle 2050 has landed the jump, the controller 39 provides another input to again automatically adjust one or more damping characteristics (such as softening) to the active valve shock assembly 1838 in the elbow and/or wrist 1838w back to a "normal" setting that provides feedback from the prosthetic arm 1801 to the user while continuing to maintain enough firmness to ensure the handlebars 36 do not easily deflect in a direction toward the prosthetic arm 1801.

In so doing, the prosthetic arm 1801 with active valve shock assembly provides the user with significantly more control and "feel" for the bicycle 2050 than a prosthetic that does not have an active valve shock assembly and which is automatically adjusted as the vehicle transitions across an environment encountering different events. That is, a non-active shock assembly is set at the highest damping setting necessary for the user to jump and land and, as such, during the rest of the ride the user receives less "feel" from the "stiff" joint.

In contrast, if the non-active shock assembly was set at a lower damping setting such that the user receives feedback and "feel" from the vehicle, the non-active shock assembly is not able to provide the required damping necessary for the user to jump and land the vehicle. Instead, at the lower damping, a prosthetic without a non-active shock assembly will not be able to keep the handlebars from deflecting into a direction toward the prosthetic and, as a result, may cause the user to lose control of the bicycle.

Although the prosthetic arm 1801 is used in the above example, it should be appreciated that the discussion applies to each of the different body wearable device types. Thus, the use of the prosthetic arm 1801 as the body wearable device is provided as one embodiment and for purposes of brevity and clarity and is not intended to indicate the only implementation of embodiments of the present invention.

In one embodiment, the same interactions are used with the prosthetic leg 1851, orthotic 1905, and/or exoskeleton 1955. Thus, by adjusting the damping characteristics, the user is able to "feel" the vehicle and its movements while also being able to hit jumps, traverse bumpy (rocky, rutty, gravelly, muddy, etc.) terrain, and the like without losing the "feel" or encountering an adverse event.

Referring now to FIG. 21, a perspective view of a snowmobile 2100 with an active suspension system with body wearable device integration is shown in accordance with an embodiment. Although a snowmobile 2100 is used in the discussion of FIG. 21, similar to the discussion of FIG. 20, the active suspension system with body wearable device integration disclosed herein is also suited for use with other vehicles such as, but not limited to a bicycle, an electric bike (e-bike), a hybrid bike, a scooter, a motorcycle, an ATV, a personal water craft (PWC), a vehicle with three or more wheels (e.g., a UTV such as a side-by-side, a car, truck, etc.), an aircraft, and the like. In one embodiment, the active suspension system with body wearable device integration disclosed herein is also suited for use in one or more suspension inclusive device such as, but not limited to, an exoskeleton (e.g., an orthotic, joint support, partial and/or full exoskeleton), an orthotic, a seat frame, one or more additional prosthetics, one or more components of a prosthetic, a suspended floor, and the like.

In general, snowmobile 2100 includes a frame 2105, seat 2110, tail section 2120, handlebars 2102, front steering assembly 2125, rear suspension assembly 2130, and a track 2132 driven by the engine of the vehicle and supported by the rear suspension assembly 2130.

In one embodiment, front steering assembly 2125 includes front skis 2128 and front shock assemblies 2137. In one embodiment, rear suspension assembly 2130 includes a front track connection with front track shock assembly 2136, a rear track connection with a rear track shock assembly 2138.

In one embodiment, snowmobile 2100 includes one or more electronically actuated components, interactive components, and/or control features such as one or more of: a user interface, active and/or semi-active shock assemblies (e.g., front track shock assembly 2136, rear track shock assembly 2138, and front shock assemblies 2137), controller 39, one or more sensor(s) 2135, a display, a power source, smart components, and the like.

In one embodiment, the one or more sensor(s) 2135 are similar to sensors 5, 35, 41, and/or other sensors as described herein, and are used to monitor and/or measure things such as location, temperature, voltage, current, resistance, noise (such as when a motor is actuated, fluid flow through a flow path, engine knocks, pings, etc.), positions of one or more components of snowmobile 2100 (e.g., shock positions, ride height, pitch, yaw, roll, etc.), and the like. In one embodiment, the one or more sensor(s) 2135 are forward looking terrain, vibrations, bump, impact event, angular measurements, GPS, and the like.

Additional information for vehicle suspension systems, sensors, and their components as well as adjustment, modification, and/or replacement aspects including manually, semi-actively, semi-actively, and/or actively controlled aspects and wired or wireless control thereof is provided in U.S. Pat. Nos. 8,838,335; 9,353,818; 9,682,604; 9,797,467; 10,036,443; 10,415,662; the content of which are incorporated by reference herein, in their entirety.

In one embodiment, one or a plurality of component(s) of snowmobile 2100 are also smart component(s). In one embodiment, the smart component(s) will include connective features that allow them to communicate wired or wirelessly with one or more of the electronically actuated components, interactive components, control features, and/or the like.

In one embodiment, data (including real-time data) is collected or provided from the smart component(s), electronically actuated components, interactive components, body wearable device, e.g., prosthetic leg 1851, control features, and/or the like to the controller 39. Depending upon the connected component, the data may be location data, sensor data, telemetry data, and the like. In general, telemetry data can include data such as angle, orientation, velocity, acceleration, RPM, operating temperature, and the like.

In one embodiment, data (such as real-time damper settings, adjustments, and the like) is provided to the smart component(s), electronically actuated components, interactive components, body wearable device, control features, and/or the like, from a controller such as controller 39, mobile device 95, another device, a controller from another vehicle, and the like (as described herein). Depending upon the connected component, the data includes firmness settings, softness settings, rebound settings, compression settings, a tune, indicators to switch between tunes, settings, etc., and the like.

In one embodiment, the body wearable device, e.g., prosthetic leg 1851, is added to the schematic of the snowmobile 2100 to show how the active valve shock assembly 1888 and/or 1888*a* (e.g., calf and/or ankle) in the prosthetic leg 1851 can be wirelessly added to the active suspension system and the integration of the prosthetic and its components 2175. In one embodiment, the same protocols for entering and operating on the network (e.g., encryption, passwords, settings, setup, specifications, and the like) are used by the active valve shock assembly 1888 (or 1888*a*) of the prosthetic leg 1851 as were used by any of the other active valve shock assemblies (e.g., as shown and described herein).

For example, in one embodiment, the controller 39 of the snowmobile 2100 is used to provide the damping characteristic adjustments to the active valve shock assembly 1888 and/or 1888*a* of the prosthetic leg 1851.

In one embodiment, bio-feedback (such as from a user's brainwaves (e.g., head 2025), muscle flexing, tendon movements, and the like) and will be provided to the controller 39 to help generate and provide the damping characteristic adjustments to the active valve shock assembly 1888 and/or 1888*a* of the prosthetic leg 1851. For example, the body wearable device (or other component) can monitor muscle contraction and change the active valve shock assembly damping as needed. In another example, a load cell or similar transducer is used to measure the force between the leg and the body wearable device and the active valve shock assembly damping is changed accordingly.

For example, as a user is riding snowmobile 2100, they may encounter a one or more obstacles, bumps, jumps, ruts, etc. As the user traverses the terrain, the controller 39 will receive information from the sensor(s) 2135 and provide adjustments to the active valves in the active valve shock assembly(s) (e.g., 2136, 2137, 2138, 1988, 1888, and/or 1888a). For example, if the user has a body wearable device, the sensor 2135 provides information to the controller 39 indicative of an upcoming (or occurring) bump (or other event). In the case of a bump, for example, the active valve shock assembly 1888 and/or 1888a receives an input from controller 39 which automatically adjusts one or more damping characteristics to provide a change in damping such that the body wearable device, e.g., prosthetic leg 1851, is ready to absorb the impact and not be either to soft or to firm.

In one embodiment, after the snowmobile 2100 has passed the bump (or other event), the controller 39 provides another input to again automatically adjust one or more damping characteristics of the active valve shock assembly 1888 and/or 1888a to return the body wearable device, e.g., prosthetic leg 1851, to its normal (or pre-bump) settings.

In so doing, the body wearable device, e.g., prosthetic leg 1851, with active valve shock assembly provides the user with significantly more control and "feel" for the snowmobile 2100 than a body wearable device that does not have an active valve shock assembly. That is, a non-active shock assembly is set at the highest damping setting necessary for the user to traverse the largest expected event and, as such, during the rest of the ride the user receives less "feel" from the "stiff" joint.

In contrast, if the non-active shock assembly was set at a lower damping setting such that the user receives feedback and "feel" from the vehicle, the non-active shock assembly is not able to provide the best damping necessary to traverse the larger events. Instead, at the lower damping setting, when a large event is encountered by the body wearable device, e.g., prosthetic leg 1851, with a non-active shock assembly the user can easily lose control.

Although the prosthetic leg 1851 body wearable device is used in the above example, it should be appreciated that the discussion also applies to any one or a plurality of body wearable devices. Thus, the use of the prosthetic leg 1851 is provided as one embodiment and for purposes of clarity.

In one embodiment, instead of the controller 39 of the vehicle, the user's mobile device 95 (or another smart component) is used to provide the damping characteristic adjustments to the active valve shock assembly of the body wearable device(s).

Referring now to FIG. 22, a perspective view of a motorcycle 2200 with an active suspension system with body wearable device integration is shown in accordance with an embodiment. Although a motorcycle 2200 is used in the discussion of FIG. 22, similar to the discussion of FIGS. 20 and 21, the active suspension system with body wearable device integration disclosed herein is also suited for use with other vehicles such as, but not limited to a bicycle, an electric bike (e-bike), a hybrid bike, a scooter, a motorcycle, an ATV, a personal water craft (PWC), a vehicle with three or more wheels (e.g., a UTV such as a side-by-side, a car, truck, etc.), an aircraft, and the like. In one embodiment, the active suspension system with body wearable device integration disclosed herein is also suited for use in one or more suspension inclusive device such as, but not limited to, an exoskeleton (e.g., an orthotic, joint support, partial and/or full exoskeleton), an orthotic, a seat frame, one or more additional prosthetics, one or more components of a prosthetic, a suspended floor, and the like.

In one embodiment, motorcycle 2200 includes one or more electronically actuated components, interactive components, and/or control features such as one or more of: a user interface, active and/or semi-active shock assemblies (e.g., front fork shock assembly 2236 and/or rear shock assembly 2238), controller 39, one or more sensor(s) 5 and 41, a display, a power source, smart components, and the like.

In one embodiment, the one or more sensor(s) 5, 41, and/or other sensors as described herein, and are used to monitor and/or measure things such as location, temperature, voltage, current, resistance, noise (such as when a motor is actuated, fluid flow through a flow path, engine knocks, pings, etc.), positions of one or more components of motorcycle 2200 (e.g., shock positions, ride height, pitch, yaw, roll, etc.), and the like. In one embodiment, the one or more sensor(s) 5 and 41 are forward looking terrain, vibrations, bump, impact event, angular measurements, GPS, and the like.

Additional information for vehicle suspension systems, sensors, and their components as well as adjustment, modification, and/or replacement aspects including manually, semi-actively, semi-actively, and/or actively controlled aspects and wired or wireless control thereof is provided in U.S. Pat. Nos. 8,838,335; 9,353,818; 9,682,604; 9,797,467; 10,036,443; 10,415,662; the content of which are incorporated by reference herein, in their entirety.

In one embodiment, one or a plurality of component(s) of motorcycle 2200 are also smart component(s). In one embodiment, the smart component(s) will include connective features that allow them to communicate wired or wirelessly with one or more of the electronically actuated components, interactive components, control features, and/or the like.

In one embodiment, data (including real-time data) is collected or provided from the smart component(s), electronically actuated components, interactive components, body wearable devices (e.g., orthotic 1905, prosthetic 1851, etc.), control features, and/or the like to the controller 39. Depending upon the connected component, the data may be location data, sensor data, telemetry data, and the like. In general, telemetry data can include data such as angle, orientation, velocity, acceleration, RPM, operating temperature, and the like.

In one embodiment, a plurality of body wearable devices, e.g., prosthetic leg 1851 and orthotic 1905, are added to the schematic of the motorcycle 2200 to show how the active valve shock assemblies and/or rotary damper can be wirelessly added to the active suspension system and the integration of the body wearable devices and their components 2275. In one embodiment, the same protocols for entering and operating on the network (e.g., encryption, passwords, settings, setup, specifications, and the like) are used by the active body wearable devices as were used by any of the other active valve shock assemblies (e.g., as shown and described herein).

For example, in one embodiment, the controller 39 of the motorcycle 2200 is used to provide the damping characteristic adjustments to the active body wearable devices.

In one embodiment, bio-feedback (such as from a user's brainwaves (e.g., head 2025), muscle flexing, tendon movements, and the like) and will be provided to the controller 39 to help generate and provide the damping characteristic adjustments to the active body wearable devices. For example, the body wearable device (or other component) can monitor muscle contraction and change the damping (and/or rotary drag, rotational range and/or rate, etc.) as needed. In another example, a load cell or similar transducer is used to measure the force acting on the body and/or the body wearable device and the damping (and/or rotary drag, rotational range and/or rate, etc.) of the active body wearable devices is changed accordingly.

In one embodiment, the user's mobile device 95 will act as both the sensor and the controller (e.g., such as by using application 1124 and settings 1013) to provide the damping characteristic adjustments to the active valve shock assembly of the body wearable device (s).

In one embodiment, the application 1124 disclosed herein is used to develop tunes for a body wearable device similar to the tunes as described herein in FIGS. 12-16E. For example, in one embodiment, a user provides the model type, description, active valve shock assembly type, personal information and vehicle information and the application is able to develop one or more tunes applicable to the body wearable device (e.g., a body wearable device tune).

In one embodiment, once a user finishes a ride (or during the ride depending upon available processor power), the body wearable device tune (or tunes) is evaluated against actual performance. For example, to determine if there were locations where the body wearable device tune was set too stiffly or too softly, where it was performing well, etc. In one embodiment, the evaluation results in additions of information to a database for developing body wearable device tunes. In one embodiment, the evaluation results in changes to the existing body wearable device tune. In one embodiment, after an evaluation, the tune may be marked as a "good" body wearable device tune and added to the library of body wearable device tunes, shared with others, etc. In one embodiment, the sharing may be point-to-point (P2P), over a network, through a database, and the like (as described herein). In one embodiment, the body wearable device tune may be location based and automatically provided to a registered user when the user is at the location.

In one embodiment, one or more of the active valve shock assemblies of the body wearable device will receive adjustment signals and/or inputs from another vehicle (or mobile device) in the riding group (such as shown in FIG. 15) to provide the damping characteristic adjustments.

In one embodiment, one or more of the active valve shock assemblies of the body wearable device will be a self-contained unit that includes a sensor and a controller to generate and provide the damping characteristic adjustments to one or more of the active valve shock assemblies of the body wearable device.

In one embodiment, one or more of the active valve shock assemblies of the body wearable device will be a self-contained unit that includes a controller and bio-feedback (such as from a user's brainwaves, muscle flexing, tendon movements, and the like) and will use the bio-feedback provided to the controller to generate and provide the damping characteristic adjustments to one or more of the active valve shock assemblies of the body wearable device.

In one embodiment, one or more of the active valve shock assemblies of the body wearable device will be a self-contained unit that includes a sensor, a controller, and bio-feedback (such as from a user's brainwaves, muscle flexing, tendon movements, and the like) and will use the bio-feedback in conjunction with sensor data provided to the controller to generate and provide the damping characteristic adjustments to one or more of the active valve shock assemblies of the body wearable device.

For example, if the user provides a bio-feedback that indicates the damping characteristics of one or more of the active valve shock assemblies of the body wearable device should be firmer (e.g., braced for landing), the controller will receive the data and increase the firmness of one or more of the active valve shock assemblies of the body wearable device.

In one embodiment, the bio-feedback is similar to present technology that allows a user to control some actions of their body wearable device via brainwaves, muscle tensing (either at the limb that is coupled with the body wearable device and/or based on actions taken by the opposite limb or other body parts of the user). For example, a skydiver with a body wearable device for their leg (or portion, joint, muscle, etc.) wants a softer damping setting while freefalling to provide better "flying" performance (e.g., positive legs to provide forward drive or reduce backsliding, etc.). That is, when the body wearable device for the leg is pushing against air pressure during freefall the force needed to make small changes in leg geometry is quite light. In one embodiment, the bio-feedback may look to the user's body (e.g., at the limb that is coupled with the body wearable device and/or based on actions taken by the opposite limb and/or other body parts) and note the amount of user added pressures (e.g., the lightness of muscle use in a remaining leg, or the user's abdomen, brainwaves, etc.) as being light to provide good control while in freefall.

In contrast, when it is time to land, the skydiver wants a firmer damping setting to allow the leg to support the user's body weight, jog forward, absorb the landing energy, etc. Here, the bio-feedback may note the amount of user added pressures are increasing to provide stability and landing energy absorption as the user prepares to land.

In one embodiment, the vehicle may be a dumb vehicle (e.g., have no controller and/or sensors, and/or wireless communications, etc.) and the information from the user's mobile device 95 and/or self-contained unit will be used to drive the damping characteristic adjustments for one or more of the active valve shock assemblies of the body wearable device. In one embodiment, there may be no vehicle (as described in the above skydiving example).

Additional information regarding examples of a self-contained active valve shock assembly can be found in U.S. Patent Publication 2022/0242190A1 entitled "Energy Harvesting Switch" and 2022/0210650A1 entitled "Wireless Switch For An Active Component" which are incorporated by reference herein, in their entirety.

As stated herein, although a bicycle 2050 is used in one embodiment and a snowmobile 2100 is used in another embodiment, it should be appreciated that the vehicle may any one of a variety of vehicles such as, but not limited to, a bicycle, a motorized bicycle, a motorcycle, a watercraft (e.g., boat, jet ski, PWC, etc.), a snow machine, a single wheeled vehicle, a multi-wheeled vehicle, a side-by-side, an on- and/or off-road vehicle, or the like. In general, a motorized bike can include a bike with a combustion motor, an electric bike (e-bike), a hybrid electric and combustion bike, a hybrid motor and pedal powered bike, and the like.

For example, in a multiple wheeled vehicle or other vehicle that includes a cockpit for the user, one or more of the active valve shock assemblies of the body wearable device integration allows the user to maintain "feel" through the steering wheel, while also being able to maintain control of the vehicle during events such as bumps, corners, jumps, etc. Similarly, a body wearable device for a leg that is operating the gas pedal or brake will be able to provide the appropriate "feel".

In one embodiment, such as a motorcycle, PWC, snow machine, or the like, where the user is interacting with handlebars and foot pegs, one or more of the active valve shock assemblies of the body wearable device integration allows the user to maintain "feel" while using the body wearable device.

Thus, in one embodiment, the active valve shock assembly body wearable device integration will help the user feel the vehicle (e.g., feedback, performance, grip, slippage, friction, surface type, etc.) and thereby "become one" with the vehicle (e.g., the feeling that the vehicle is an extension of the user's body).

The foregoing Description of Embodiments is not intended to be exhaustive or to limit the embodiments to the precise form described. Instead, example embodiments in this Description of Embodiments have been presented in order to enable persons of skill in the art to make and use embodiments of the described subject matter. Moreover, various embodiments have been described in various combinations. In addition, there are embodiments where two or more embodiments are combined. Although some embodiments have been described in a language specific to structural features and/or methodological acts, it is to be understood that the subject matter defined in the appended claims is not necessarily limited to the specific features or acts described above. Rather, the specific features and acts described above are disclosed by way of illustration and as example forms of implementing the claims and their equivalents.

What we claim is:

1. A body wearable device comprising:
    a shock assembly having at least one active valve;
    a controller communicatively coupled with said at least one active valve of said shock assembly, said controller configured to communicate damping adjustment information to said at least one active valve of said shock assembly, said damping adjustment information used by said at least one active valve to modify a damping characteristic of said shock assembly; and
    at least one sensor to communicate sensor data to said controller wherein said controller generates said damping adjustment information based on said sensor data, wherein said at least one sensor is coupled with a vehicle and obtains data related to an operation of said vehicle, said controller further configured to store a plurality of settings for said shock assembly, such that said plurality of settings are available for selection during said operation of said vehicle.

2. The body wearable device of claim 1, wherein said controller is in wireless communication with said at least one sensor.

3. The body wearable device of claim 1, wherein said controller is in wired communication with said at least one sensor.

4. The body wearable device of claim 1, wherein said at least one sensor is coupled with said body wearable device and obtains data related to an operation of a vehicle to which a user of said body wearable device is utilizing.

5. The body wearable device of claim 1, wherein said at least one sensor is coupled with a user of said body wearable device and obtains data from at least one bodily function of said user.

6. A wireless active suspension system with body wearable device integration comprising:
    a prosthetic comprising a shock assembly with at least one active valve;
    a controller coupled with a vehicle, said controller in wireless communication with said at least one active valve of said shock assembly to wirelessly communicate damping adjustment information to said at least one active valve of said shock assembly, said damping adjustment information used by said at least one active valve to modify at least one damping characteristic of said shock assembly; and
    at least one sensor to communicate sensor data to said controller wherein said controller generates said damping adjustment information based on said sensor data, wherein said at least one sensor is coupled with said vehicle and obtains data related to an operation of said vehicle, said controller further configured to store a plurality of settings for said shock assembly, such that said plurality of settings are available for selection during said operation of said vehicle.

7. The wireless active suspension system of claim 6, wherein said controller is in wireless communication with said at least one sensor.

8. The wireless active suspension system of claim 6, wherein said controller is in wired communication with said at least one sensor.

9. The wireless active suspension system of claim 6, wherein said at least one sensor is coupled with said prosthetic and obtains data related to an operation of said vehicle which a user of said prosthetic is utilizing.

10. The wireless active suspension system of claim 6, wherein said at least one sensor is coupled with a user of said prosthetic and obtains bio-feedback data from at least one bodily function of said user.

11. An active suspension system with prosthetic integration comprising:
    a prosthetic comprising a shock assembly with at least one active valve;
    at least one sensor to generate sensor data as a vehicle traverses an environment; and
    a controller communicatively coupled with said prosthetic and said at least one sensor, said controller configured to:
        receive said sensor data from said at least one sensor;
        utilize said sensor data corresponding to said vehicle to determine an adjustment to said at least one active valve of said shock assembly;
        communicate said adjustment to said at least one active valve of said shock assembly, said adjustment to modify at least one damping characteristic of said shock assembly; and
        said controller further configured to store a plurality of settings for said shock assembly, such that said plurality of settings are available for selection as said vehicle traverses said environment.

12. The active suspension system of claim 11, wherein said controller is in wireless communication with said at least one active valve of said shock assembly.

13. The active suspension system of claim 11, wherein said controller is in wireless communication with said at least one active valve of said shock assembly and said at least one sensor.

14. The active suspension system of claim 11, wherein said controller is in wired communication with at least one of said at least one sensor and said at least one active valve of said shock assembly.

15. The active suspension system of claim 11, wherein said at least one sensor is coupled with said vehicle and obtains data related to an operation of said vehicle as said vehicle traverses said environment.

16. The active suspension system of claim 11, wherein said at least one sensor is coupled with said prosthetic and obtains data related to an operation of said vehicle to which a user of said prosthetic is utilizing as said vehicle traverses said environment.

17. The active suspension system of claim 11, further comprising:
a bio-feedback sensor coupled with a user of said prosthetic, said bio-feedback sensor to obtain bio-feedback data from said user; and
said controller communicatively coupled with said prosthetic, said at least one sensor, and said bio-feedback sensor, said controller configured to:
receive said sensor data from said at least one sensor and said bio-feedback data from said bio-feedback sensor; and
utilize said sensor data in conjunction with said bio-feedback data to determine said adjustment to said at least one active valve of said shock assembly.

18. A vehicle suspension system with orthotic integration comprising:
an orthotic comprising at least one remotely adjustable damper; and
a controller coupled with a vehicle, said controller in wireless communication with said at least one remotely adjustable damper to wirelessly communicate adjustment information to said at least one remotely adjustable damper of said orthotic, said adjustment information used by said at least one remotely adjustable damper to modify at least one performance characteristic of said orthotic, said controller further configured to store a plurality of settings for said at least one remotely adjustable damper, such that said plurality of settings are available for selection during use of said orthotic.

19. The vehicle suspension system with orthotic integration of claim 18, wherein said at least one remotely adjustable damper is a rotary damper.

20. The vehicle suspension system with orthotic integration of claim 18, further comprising:
at least one sensor to communicate a sensor data to said controller wherein said controller generates said damping adjustment information based on said sensor data.

21. The vehicle suspension system with orthotic integration of claim 20, wherein said controller is in wireless communication with said at least one sensor.

22. The vehicle suspension system with orthotic integration of claim 20, wherein said controller is in wired communication with said at least one sensor.

23. The vehicle suspension system with orthotic integration of claim 20, wherein said at least one sensor is coupled with said vehicle and obtains data related to an operation of said vehicle.

24. The vehicle suspension system with orthotic integration of claim 20, wherein said at least one sensor is coupled with said orthotic and obtains data related to an operation of said vehicle to which a user of said orthotic is utilizing.

25. The vehicle suspension system with orthotic integration of claim 20, wherein said at least one sensor is coupled with a user of said orthotic and obtains bio-feedback data from at least one bodily function of said user.

26. A vehicle suspension system with body wearable device integration comprising:
a body wearable device comprising at least one remotely adjustable damper; and
a controller coupled with a vehicle, said controller in wireless communication with said at least one remotely adjustable damper of said body wearable device to wirelessly communicate adjustment information to said at least one remotely adjustable damper, said adjustment information used by said at least one remotely adjustable damper to modify at least one performance characteristic of said body wearable device, said controller further configured to store a plurality of settings for said at least one remotely adjustable damper, such that said plurality of settings are available for selection during use of said body wearable device.

27. The active suspension system with body wearable device integration of claim 26, wherein said body wearable device is a prosthetic.

28. The active suspension system with body wearable device integration of claim 26, wherein said body wearable device is an orthotic.

29. The active suspension system with body wearable device integration of claim 28, wherein said at least one remotely adjustable damper is a rotary damper.

30. The active suspension system with body wearable device integration of claim 26, wherein said body wearable device is an exoskeleton.

31. The active suspension system with body wearable device integration of claim 26, further comprising:
a plurality of body wearable devices, wherein said plurality of body wearable devices are selected from a group consisting of: prosthetics, orthotics, and exoskeletons.

32. The active suspension system with body wearable device integration of claim 26, further comprising:
at least one sensor to communicate a sensor data to said controller wherein said controller generates said damping adjustment information based on said sensor data.

33. The active suspension system with body wearable device integration of claim 32, wherein said controller is in wireless communication with said at least one sensor.

34. The active suspension system with body wearable device integration of claim 32, wherein said controller is in wired communication with said at least one sensor.

35. The active suspension system with body wearable device integration of claim 32, wherein said at least one sensor is coupled with said vehicle and obtains data related to an operation of said vehicle.

36. The active suspension system with body wearable device integration of claim 32, wherein said at least one sensor is coupled with said body wearable device and obtains data related to an operation of said vehicle to which a user of said body wearable device is utilizing.

37. The active suspension system with body wearable device integration of claim 32, wherein said at least one sensor is coupled with a user of said body wearable device and obtains bio-feedback data from at least one bodily function of said user.

* * * * *